US012576137B2

(12) United States Patent
Lee et al.

(10) Patent No.: US 12,576,137 B2
(45) Date of Patent: Mar. 17, 2026

(54) COLLAGEN HYDROLYSATE COMPRISING GPCR LIGAND PEPTIDE

(71) Applicant: Industry-Academic Cooperation Foundation, Yonsei University, Seoul (KR)

(72) Inventors: Dong Woo Lee, Daegu (KR); Hyeon Su Jin, Seoul (KR); Ji Young Lee, Seoul (KR); Jae Eun Lee, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 671 days.

(21) Appl. No.: 18/058,451

(22) Filed: Nov. 23, 2022

(65) Prior Publication Data

US 2024/0139291 A1      May 2, 2024

(30) Foreign Application Priority Data

Nov. 25, 2021      (KR) ........................ 10-2021-0164612

(51) Int. Cl.
| | |
|---|---|
| *A61K 38/39* | (2006.01) |
| *A61P 17/02* | (2006.01) |
| *A61P 29/00* | (2006.01) |

(52) U.S. Cl.
CPC .............. *A61K 38/39* (2013.01); *A61P 17/02* (2018.01); *A61P 29/00* (2018.01)

(58) Field of Classification Search
None
See application file for complete search history.

(56) References Cited

PUBLICATIONS

Raveschot et al., "Production of Bioactive Peptides by *lactobacillus* Species: From Gene to Application", Frontiers in Microbiology 9: 2354 October (Year: 2018).*
Hwang et al., "Screening and Identification of Bioactive Peptides Derived from Collagen Using *lactobacillus* Species," The Graduate School, Yonsei University: A Master's Thesis, pp. 1-69, Aug. 2021.
Collagen alpha-2(I) chain isoform X2 [Pangasianodon hypophthalmus], Genbank accession No. XP_026785766.1 (May 13, 2020).

* cited by examiner

*Primary Examiner* — Anand U Desai
(74) *Attorney, Agent, or Firm* — Panitch Schwarze Belisario & Nadel LLP

(57)      ABSTRACT

The present invention relates to GPCR ligand collagen peptides produced through microbial fermentation, and in particular, to a method of preparing collagen peptides obtained by culturing a microorganism, peptides prepared by the method, and a composition including the peptide as an active ingredient; and a composition for improving intestinal function, relieving inflammation, and/or promoting wound healing, and a method of preparing the composition.

4 Claims, 17 Drawing Sheets

Specification includes a Sequence Listing.

[Fig.1]

[Fig.3A]
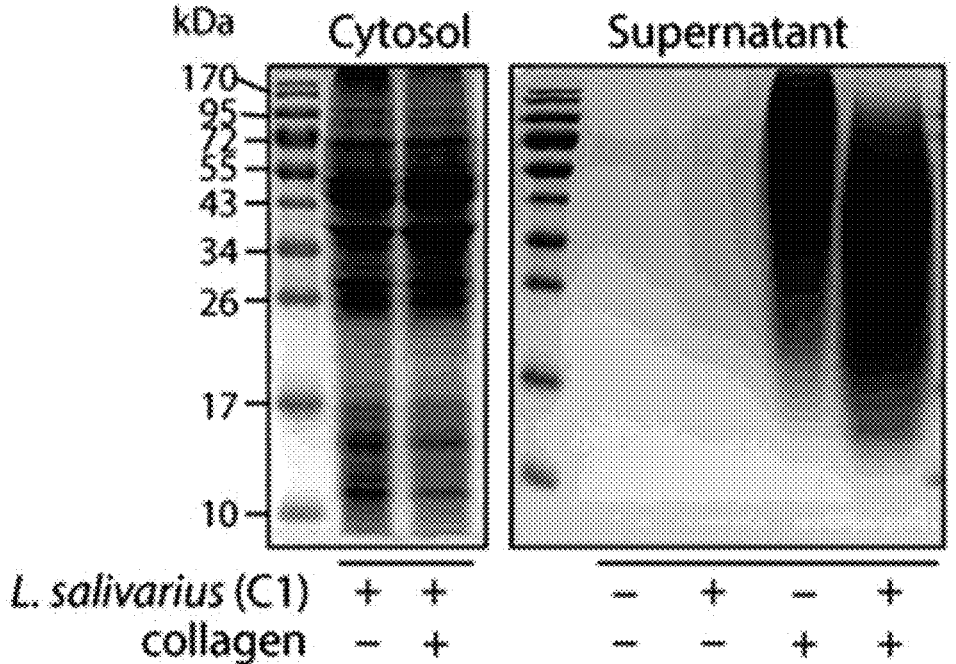
[Fig.3B]
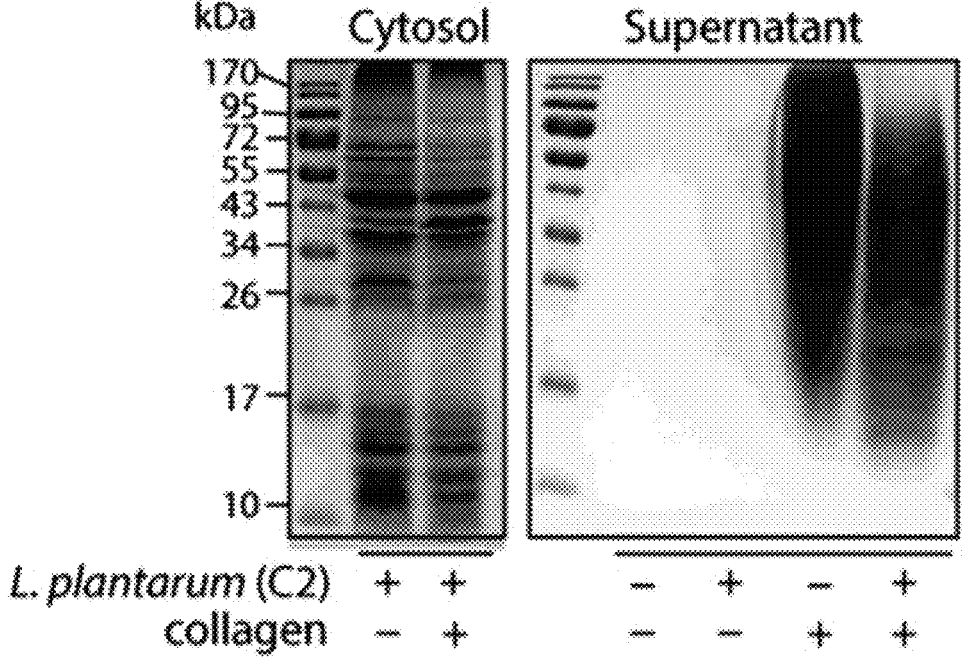

[Fig.3C]
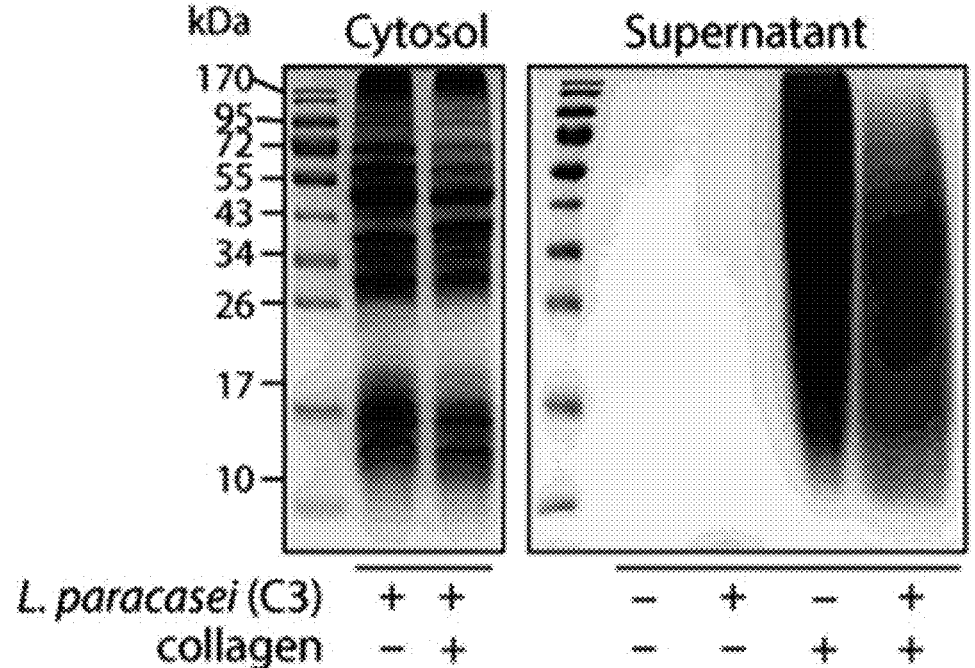
[Fig.3D]
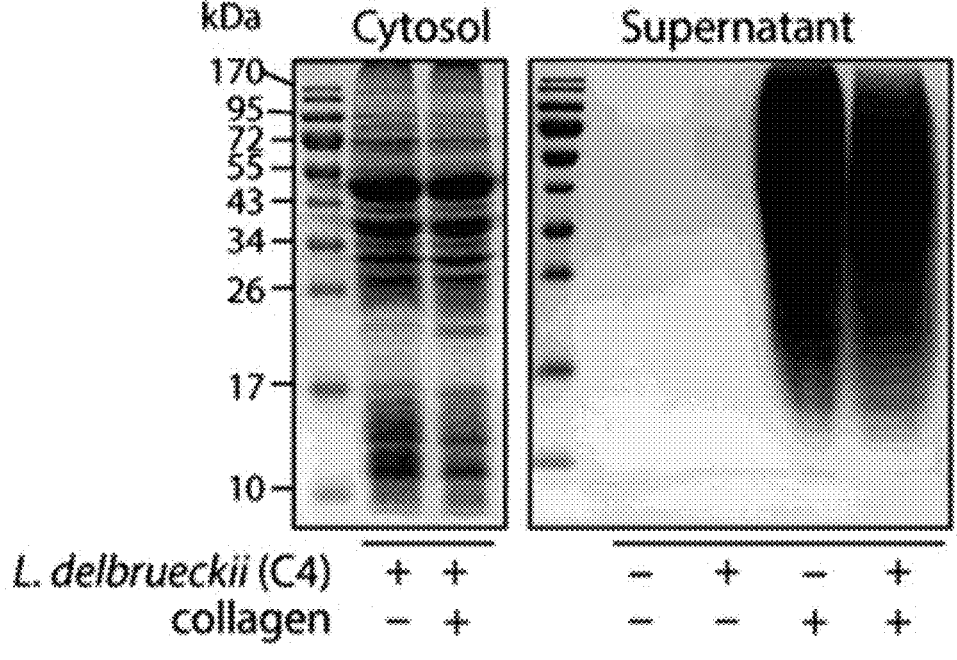

[Fig.4A]
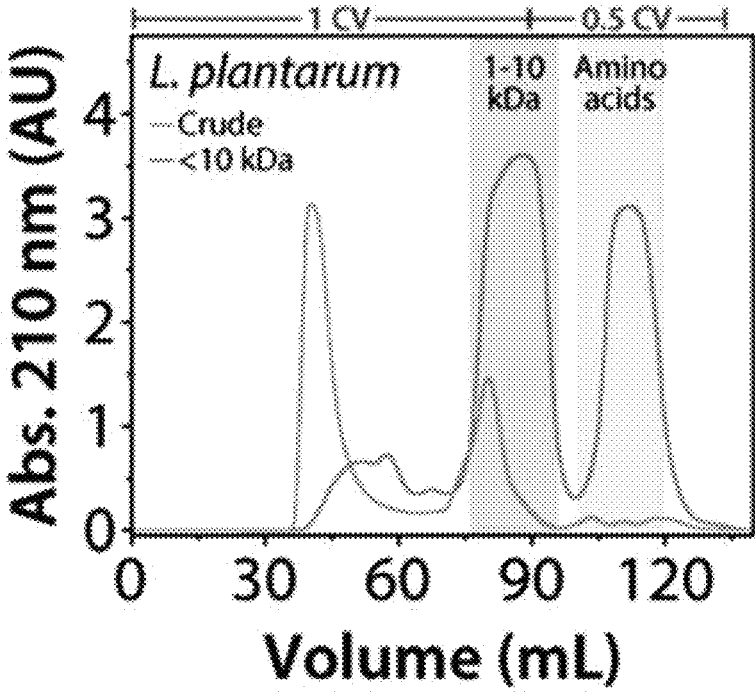
[Fig.4B]
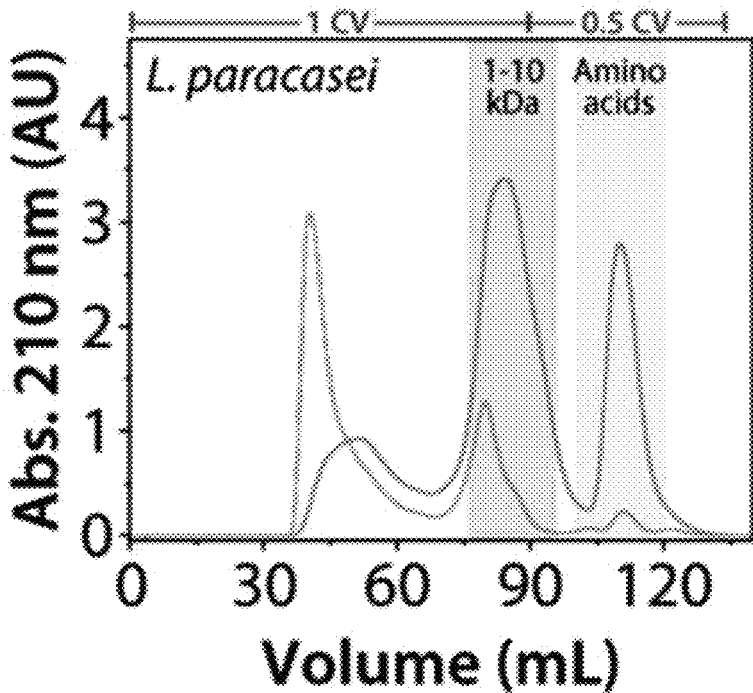

[Fig.4C]
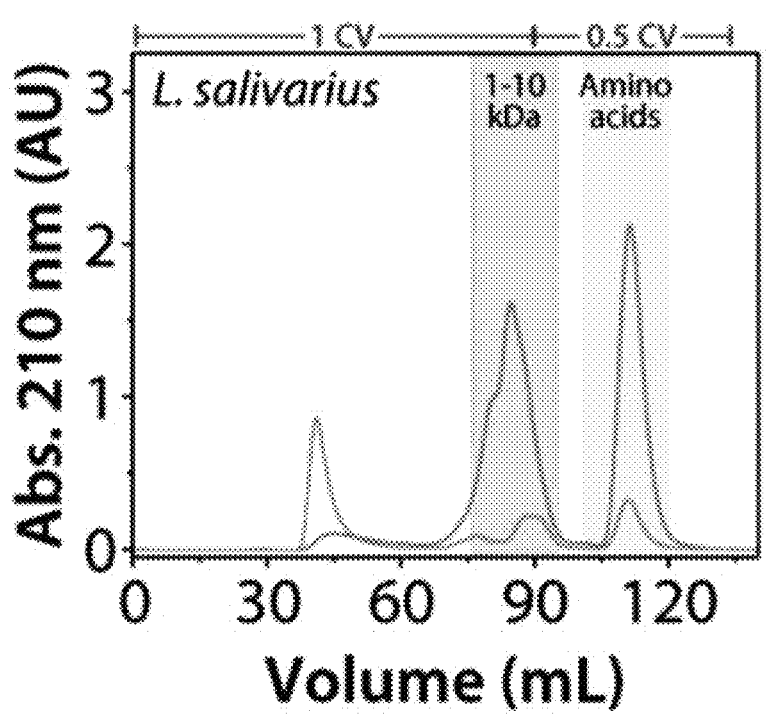

[Fig.5A]
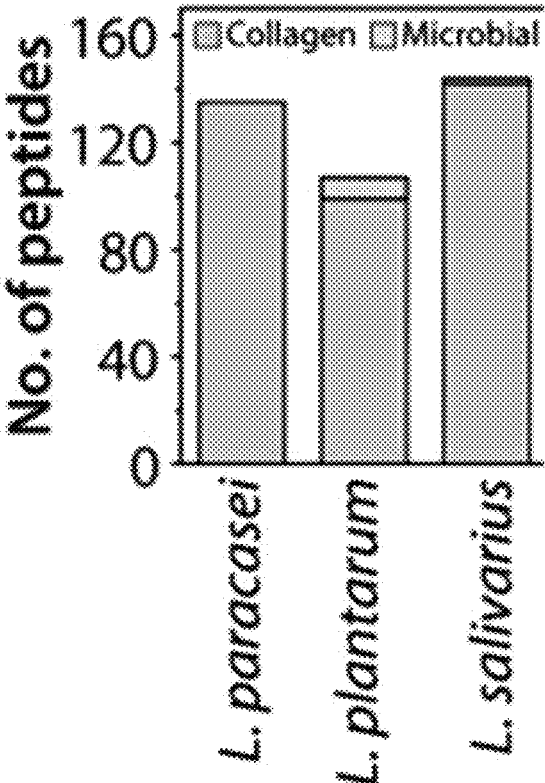
[Fig.5B]
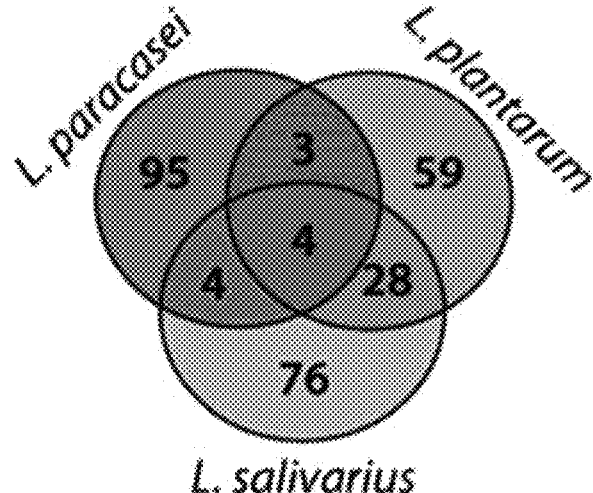

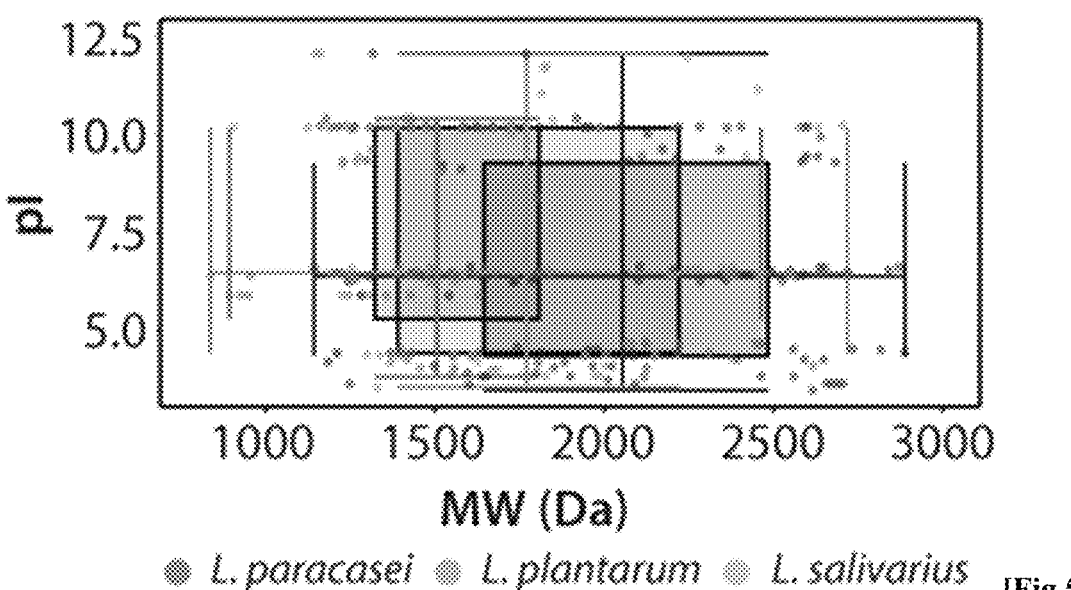
● *L. paracasei* ● *L. plantarum* ● *L. salivarius*
[Fig.5C]
*P. hypophthalmus* collagen alpha-2(I) chain isoform X2
SEQ ID NO: 175
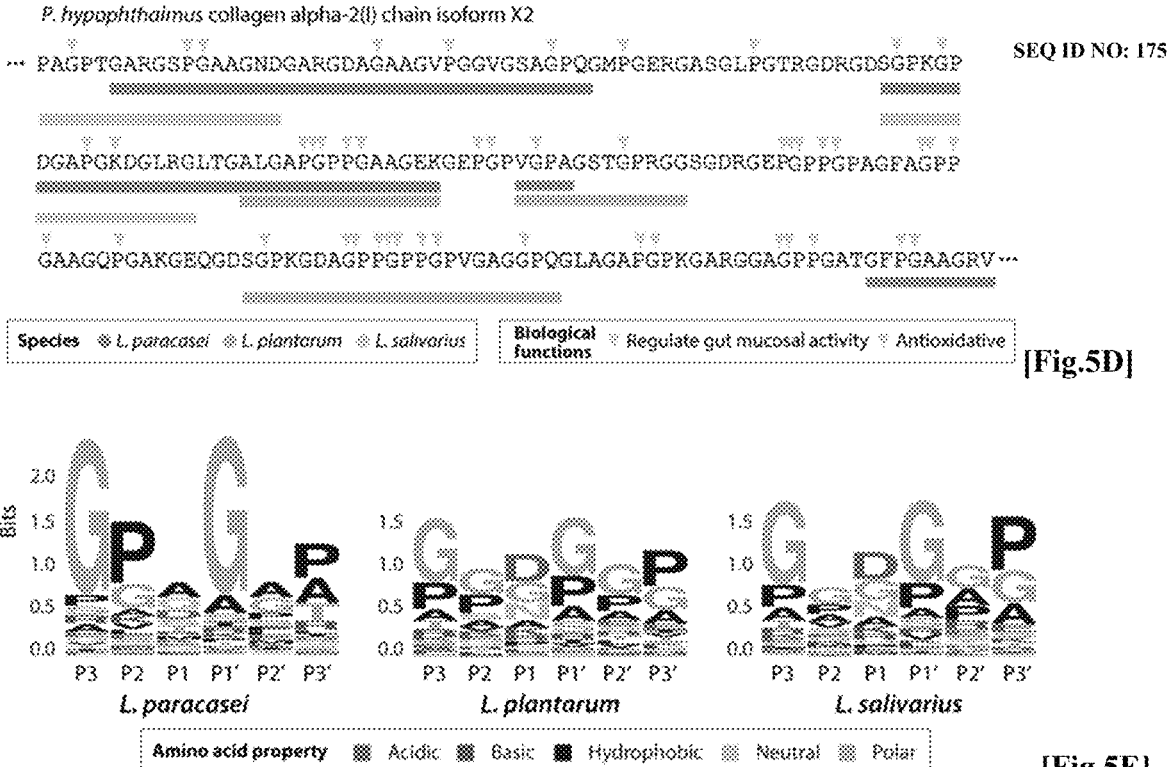
[Fig.5D]
*L. paracasei*          *L. plantarum*          *L. salivarius*
[Fig.5E]

[Fig.6A]
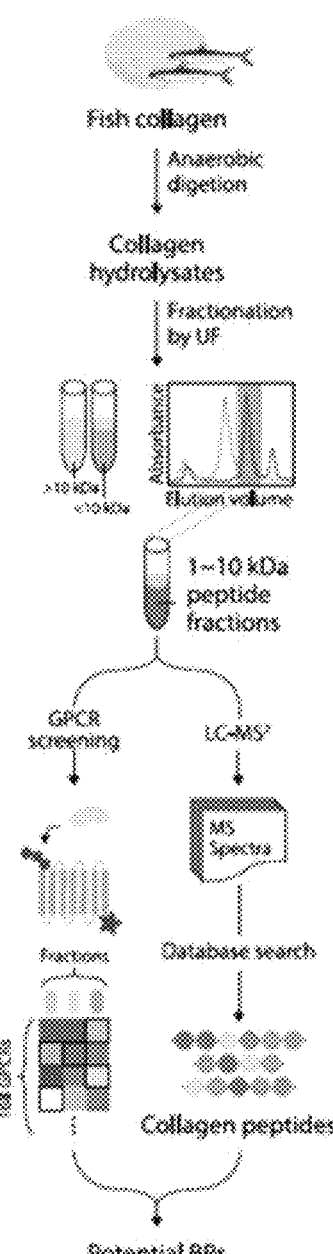

[Fig.6B]
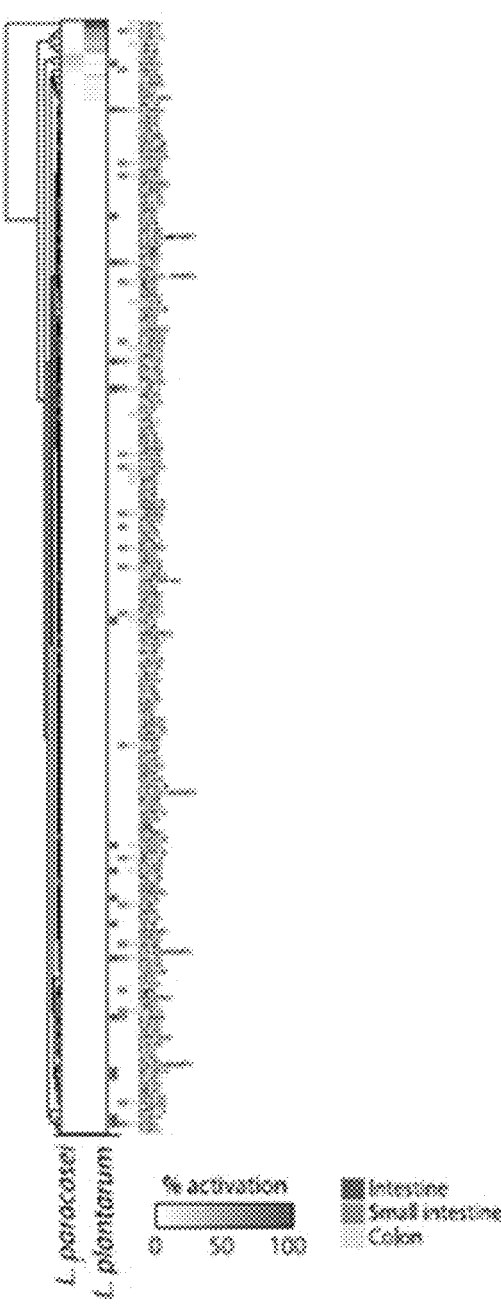

[Fig.6C]
168 GPCRs
↓
**Expressed\* in intestine**
\*Medium to high tissue expression levels
in colon or small intestine,
or high RNA expression levels in intestine
44 GPCRs
**> 10% activation
of GPCR**
5 GPCRs
(GPR35, HRH1, HRH2, P2RY1, P2RY6)
**Activated by collagen
derived from both probiotics**
GPR35

[Fig.6D]
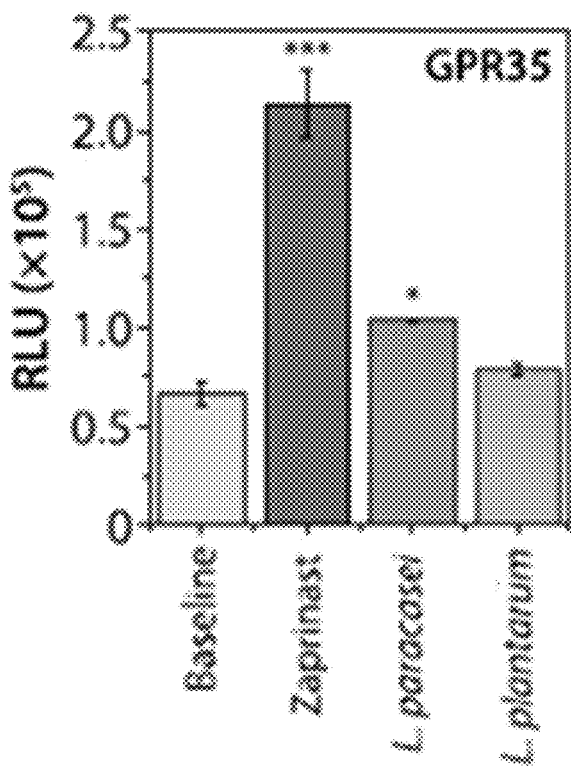

[Fig.7]
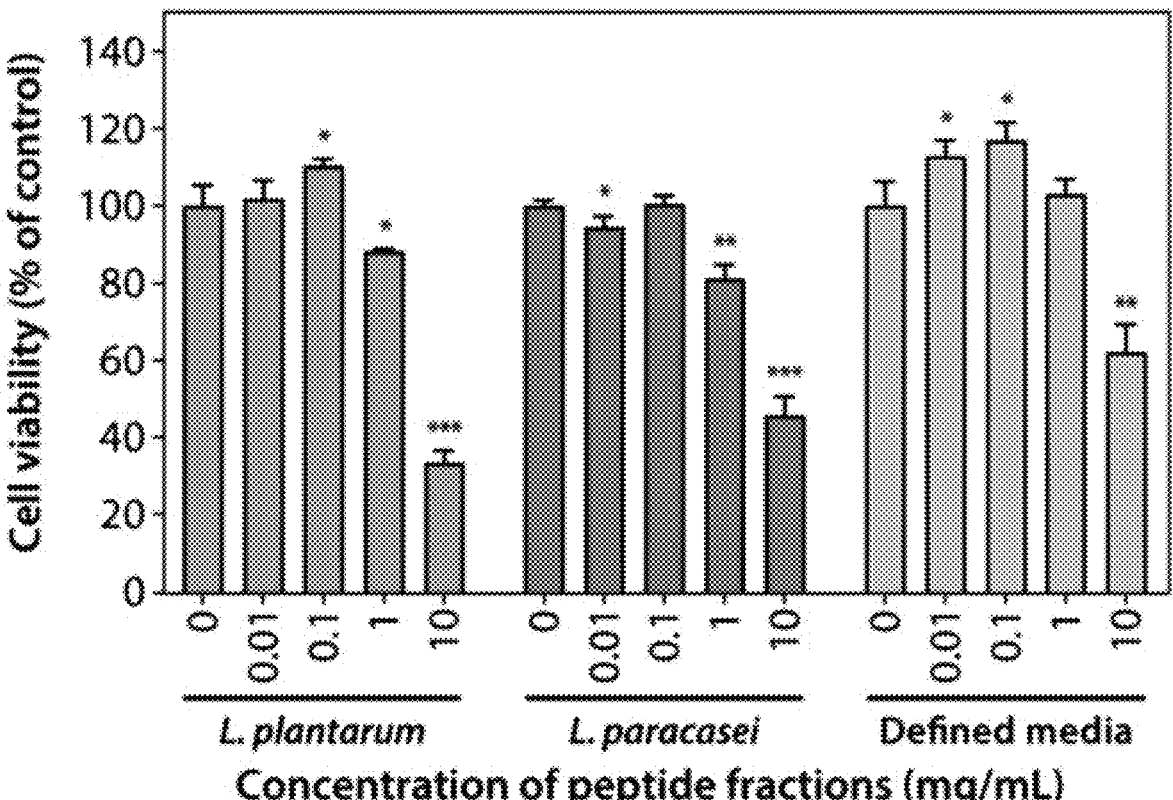
[FIG.8A]
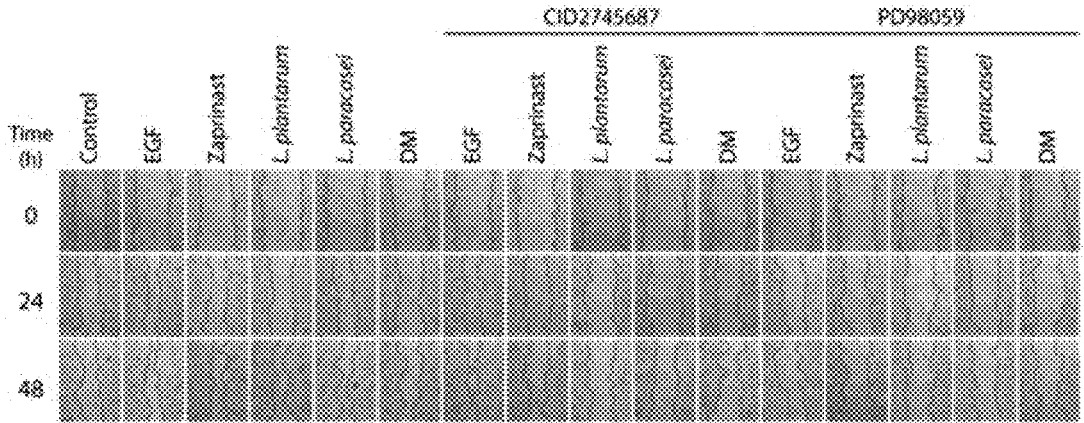

[Fig.8B]
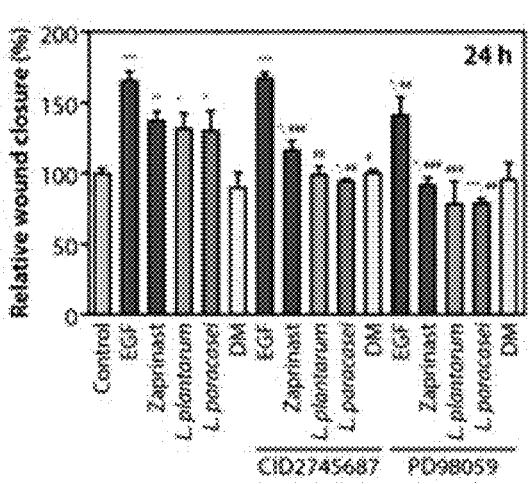 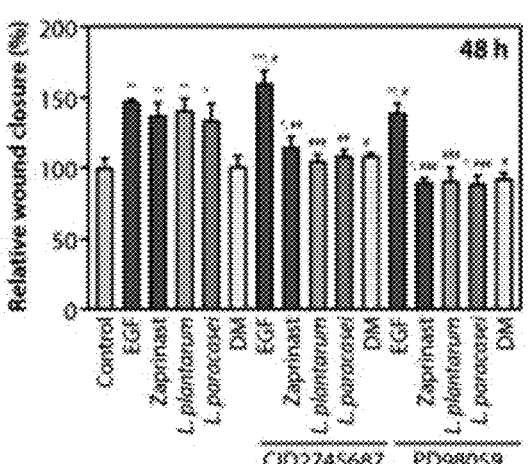
[Fig.8C]
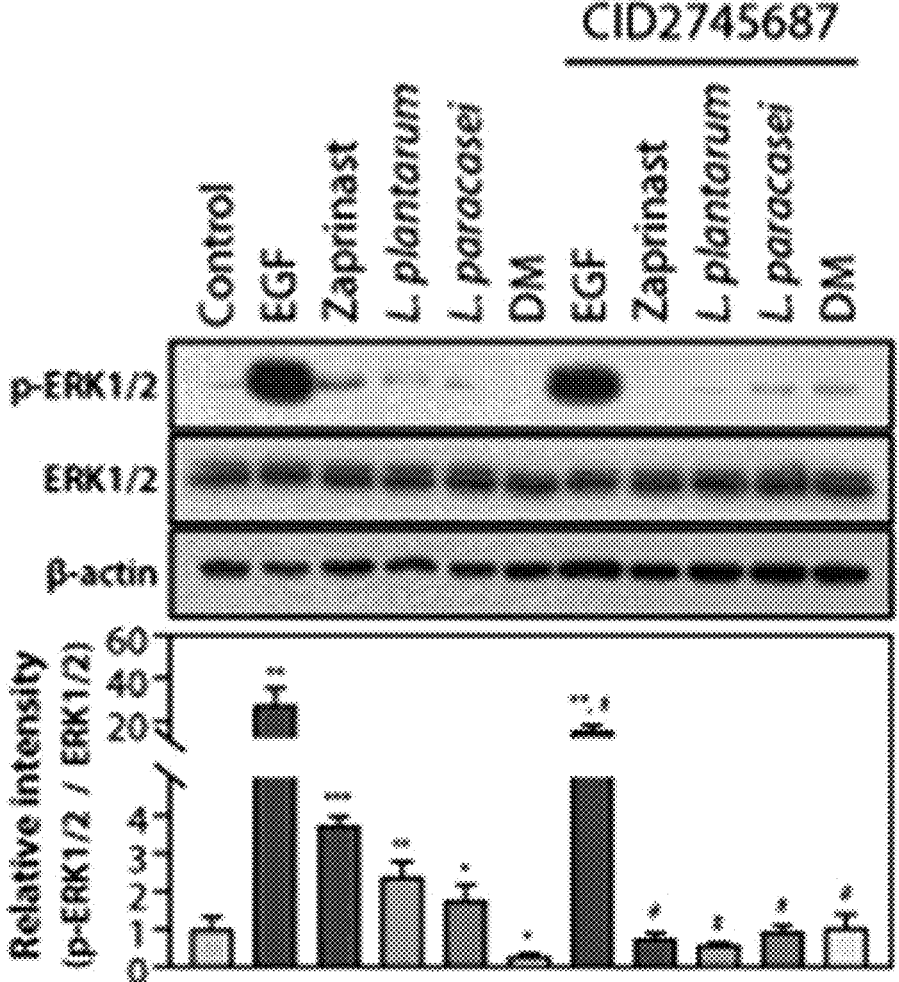

[Fig.9A]
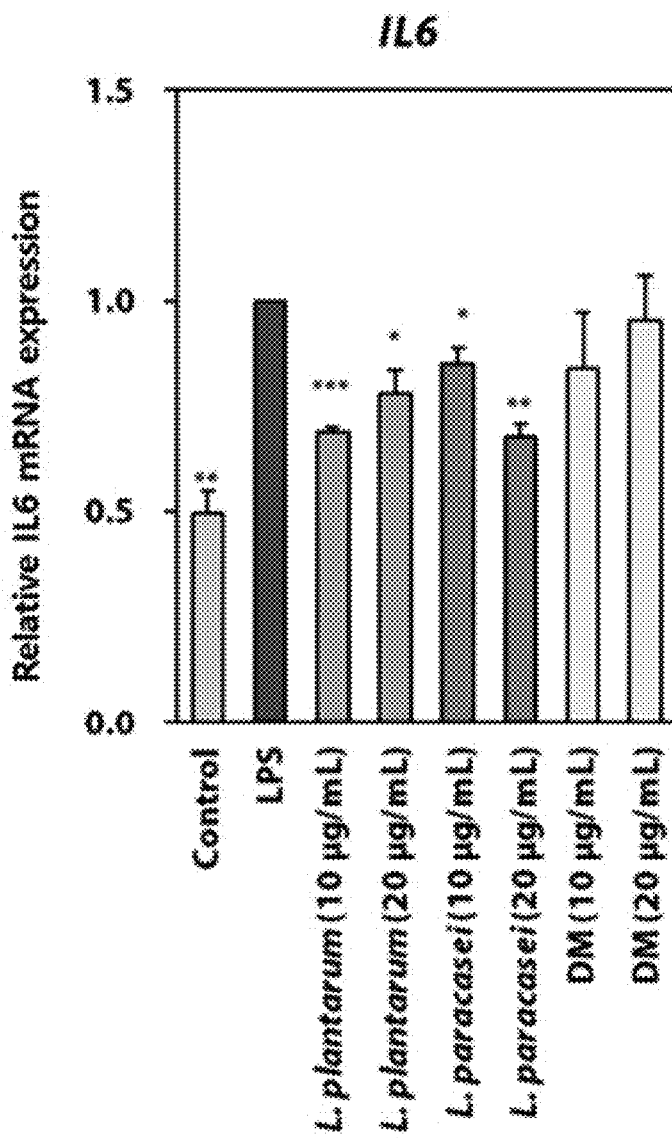

[Fig.9B]
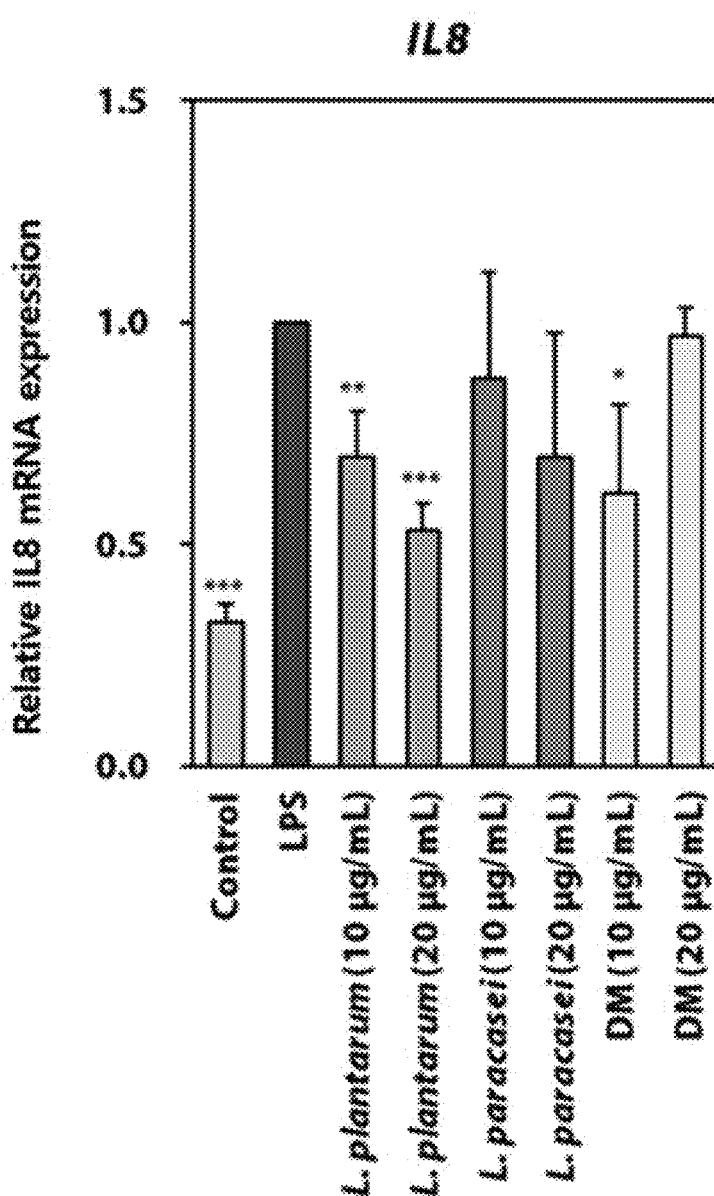

[Fig.9C]
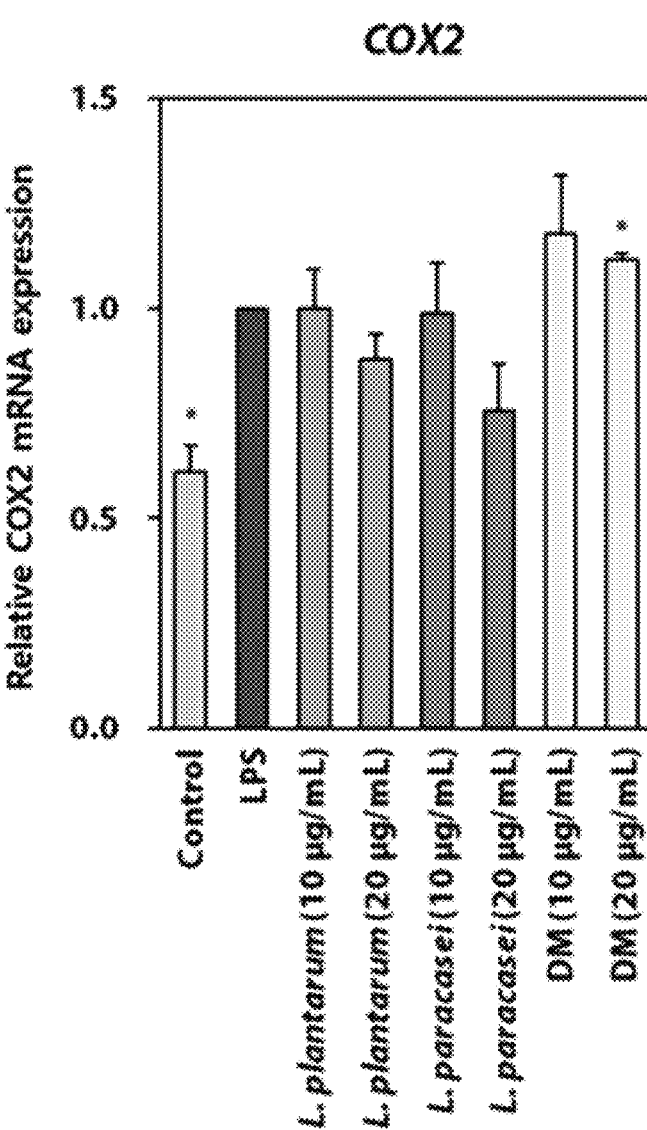

COLLAGEN HYDROLYSATE COMPRISING GPCR LIGAND PEPTIDE

CROSS-REFERENCE TO RELATED APPLICATIONS

This application claims priority under 35 U.S.C. § 119 (b) to Korean Application No. 10-2021-0164612, filed Nov. 25, 2021, the disclosure of which is incorporated herein by reference in its entirety.

REFERENCE TO SEQUENCE LISTING SUBMITTED ELECTRONICALLY

This application contains a Sequence Listing, which is submitted electronically via EFS-Web as a XML formatted sequence listing with a file name "688588-67US_Sequence Listing", creation date of Nov. 23, 2022, and having a size of 205,282 bytes. The Sequence Listing submitted via EFS-Web is part of the specification and is herein incorporated by reference in its entirety.

BACKGROUND

1. Field of the Invention

The present invention relates to GPCR ligand collagen peptides produced through microbial fermentation, and in particular, to a method of preparing collagen peptides obtained by microbial cultivation, a peptide prepared by the method, and a composition including the peptide as an active ingredient, and to a composition for improving intestinal function, relieving inflammation, and/or promoting wound healing, and a method of preparing the composition.

The present invention claims priority based on the application date of Nov. 25, 2021, application number 10-2021-0164612, the title "Collagen hydrolysate containing GPCR ligand peptide," and all contents disclosed in the literature of the patent application are included as part of the present invention.

2. Discussion of Related Art

Collagen is a protein found in most animals and, particularly, is a major protein constituting the flesh and connective tissue of mammals. Collagen is abundant enough to account for 25% to 35% of the protein that makes up the body. Collagen in the form of stretched fibers is mainly present in fibrous tissues such as tendons, ligaments, and skin and is also present in corneas, cartilage tissue, bones, blood vessels, the digestive tract, and spinal discs.

Collagen is a protein that accounts for the largest part quantitatively and functionally in the human body and refers to a main component of the extracellular matrix that forms the skeleton of all cells in the human body, more specifically, connective tissue. Human tissue containing a large amount of collagen includes skin, bone tissue such as bone and cartilage, tendons, ligaments, and the like. Aging of these tissues results in aging-related diseases such as skin wrinkles and sagging and osteoporosis, which is known to be caused by a decrease in the amount and function of collagen in the body due to a decrease in collagen synthesis in tissues.

The amount of collagen produced in the body decreases with age, and it is known that collagen production peaks in the 20s, drops to 70% in the 40s, and then rapidly decreases. Therefore, since collagen is not a substance produced in the body, it needs to be ingested through food.

Peptides are an ingredient that has recently attracted attention in various research areas such as cosmetics, foods, and pharmaceuticals. Peptides are polymers in which about 2 to 50 of the 20 essential amino acids are linked through amide bonds, and although peptide has a simpler size and structure than proteins, it is known to play an important role in in vivo metabolic processes due to its extensive interactions with proteins in vivo. Therefore, studies related to peptide materials are already in progress in various fields such as anti-cancer, anti-inflammatory, and anti-obesity fields, and most peptides used as various pharmaceutical preparations are chemically synthesized. Recently, studies on the physiological activity of hydrolysates obtained by hydrolyzing animal and plant proteins using various enzymes have been actively conducted. Studies have reported that various protein hydrolysates have antioxidant, antibacterial, antiserum (platelet aggregation inhibition), immune regulation, anti-cancer and anti-obesity effects, and these protein hydrolysates are used in various fields such as food, cosmetics, and food and drug materials.

SUMMARY OF THE INVENTION

The present inventors constructed a bioinformatics-based semi-rational strategy to screen for bioactive collagen peptides that bind to an intestinal G-protein coupled receptor (GPCR) using strains belonging to the *Lactobacilluseae* family. Through this, fractions exhibiting binding activity to GPCR were selected, and amino acid sequences of the bioactive peptides capable of regulating intestinal metabolic functions were identified.

Accordingly, the present invention is directed to providing food, cosmetics (inner beauty), and feed compositions for improving intestinal function, wherein the composition includes, as an active ingredient, collagen peptides obtained by cultivation with one or more microorganisms selected from *Lacticaseibacillus paracasei, Lactiplantibacillus plantarum*, and *Ligilactobacillus salivarius*; the collagen peptides are selected from collagen peptides having a molecular weight of less than 1 kDa, 1 to 10 kDa, and greater than 10 kDa, and each of the collagen peptides has GPR35 activity.

In addition, the present invention is also directed to providing food and cosmetics (inner beauty) for relieving inflammation and/or promoting wound healing, and a pharmaceutical composition for reducing inflammation and/or promoting wound healing, wherein the composition includes, as an active ingredient, collagen peptides obtained by cultivation with one or more microorganisms selected from *L. paracasei, L. plantarum*, and *L. salivarius*; the collagen peptides are selected from collagen peptides having a molecular weight of less than 1 kDa, 1 to 10 kDa, and greater than 10 kDa, and each of the collagen peptides has GPR35 activity.

In addition, the present invention is also directed to providing a method of preparing collagen peptides having GPR35 activity, including: (1) culturing one or more microorganisms selected from *L. paracasei, L. plantarum*, and *L. salivarius*, which have collagen degrading activity, in a collagen-containing medium to obtain a collagen hydrolysates, fractionating the collagen hydrolysate, and purifying the protein hydrolysate fractions into proteins and peptides; and (2) screening for physiological activities and analyzing the sequences of the purified peptides obtained in step (1) to obtain bioactive peptides derived from collagen.

In addition, the present invention is also directed to providing collagen peptides consisting of amino acid sequences selected from the group consisting of SEQ ID NOs: 1 to 174.

However, the technical problem to be achieved by the present invention is not limited to the above-mentioned problems, and other problems not mentioned will be clearly understood by those skilled in the art from the following description.

Means to Solve the Problem

Hereinafter, various embodiments described in this specification are described with reference to the drawings. In the following description, numerous specific details are set forth, such as specific forms, compositions and processes, and the like, in order to provide a thorough understanding of the present invention. However, certain embodiments may be practiced without one or more of these specific details or with other known methods and forms. In other instances, well-known processes and manufacturing techniques have not been described in specific detail in order not to unnecessarily obscure the present invention. Reference throughout this specification to "one embodiment" or "an embodiment" means that a particular feature, form, composition or characteristic described in connection with the embodiment is included in one or more embodiments of the present invention. Thus, "in one embodiment" or "an embodiment" throughout this specification do not necessarily refer to the same embodiment of the invention. Additionally, particular features, forms, compositions, or properties may be combined in one or more embodiments in any suitable way.

Unless specifically defined in the present invention, all scientific and technical terms used herein have the same meaning as commonly understood by a person skilled in the art to which the present invention belongs.

One embodiment of the present invention relates to a food and feed composition for improving intestinal function, wherein the composition includes, as an active ingredient, collagen peptides obtained by culturing one or more microorganisms selected from *L. paracasei, L. plantarum*, and *L. salivarius,*

In addition, one embodiment of the present invention relates to a pharmaceutical composition, a food and cosmetics composition for relieving inflammation and/or promoting wound healing, wherein the composition includes, as an active ingredient, collagen peptides obtained by culturing one or more microorganisms selected from *L. paracasei, L. plantarum*, and *L. salivarius,*

In the present invention, the collagen peptide may be selected from collagen peptides having a molecular weight of less than 1 kDa, 1 to 10 kDa, and greater than 10 kDa, and the collagen peptide may have GPR35 activity.

In the present invention, "collagen peptide" may be collagen peptide extracted from resources obtained from animals, plants, or marine life as raw materials, and the animal may be a pig or a cow, and preferably pork skin, bovine skin, pork bone, or beef bone may be used. The plant may be carrots, red ginseng, pine needles, sesame seeds, enoki mushrooms, oyster mushrooms, and the like, and the marine life may be any one or more selected from the group consisting of fish, fish scales, fish skins, mollusks, and crustaceans, and preferably may be fish skins.

The term "peptide" used throughout this specification refers to a linear molecule formed by linking amino acid residues to each other by a peptide bond (—CO—NH—). The peptide herein may be prepared according to chemical synthesis methods known in the art, particularly solid phase synthesis techniques (Merrifield, J. Amer. Chem. Soc. 85:2149-54 (1963); Stewart, et al., Solid Phase Peptide Synthesis, 2nd. ed., Pierce Chem. Co.: Rockford, 111 (1984)) or liquid phase synthesis techniques (US Registration U.S. Pat. No. 5,516,891), and an amino acid residue that makes up the peptides herein may be a natural or non-natural amino acid residue.

In the present invention, "GPR35" is an abbreviation for G protein-coupled receptor 35 and is a receptor for kynurenic acid, an intermediate in the tryptophan metabolic pathway. GPR35 mediates calcium mobilization and production of inositol phosphate. GPR35 and a nucleic acid encoding GPR35 are characterized by NCBI Entrez Gene ID 2859. Studies have shown that GPR35 is involved in the regulation of inflammation either by the presence of receptors on the surface of immune-specific cells or by activation of agonists leading to changes in an immune response. Thus, GPR35 and the nucleic acid encoding GPR35 are hypothesized to play a role in inflammatory disease pathology, making GPR35 an important therapeutic target for treating inflammatory diseases or conditions.

In the present invention, "pharmaceutical composition for relieving inflammation" includes, but is not limited to, one or more inflammatory diseases selected from arthritis, rhinitis, hepatitis, keratitis, gastritis, enteritis, nephritis, bronchitis, pleurisy, peritonitis, spondylitis, pancreatitis, urethritis, cystitis, burning inflammation, dermatitis, periodontitis, gingivitis, and degenerative neuro-inflammation.

The composition of the present invention may further include one or more known active ingredient having an effect of improving intestinal function, preventing or treating an inflammatory disease, along with collagen peptides obtained by culturing microorganisms.

The composition of the present invention may further include a suitable carrier, excipient, and diluent commonly used in the preparation of pharmaceutical compositions. In addition, the composition may be formulated and used in the form of oral formulations such as powders, granules, tablets, capsules, suspensions, emulsions, syrups, aerosols, and the like, external preparations, suppositories, and sterile injection solutions according to existing methods. Suitable formulations known in the art may be those disclosed in the literature (Remington's Pharmaceutical Science, recently, Mack Publishing Company, Easton PA).

Such carriers are commonly used in formulation and include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, and mineral oil. The pharmaceutical composition of the present disclosure may further include, in addition to the above components, lubricants, wetting agents, sweetening agents, flavoring agents, emulsifying agents, suspending agents, preservatives, and the like.

A suitable dosage of the pharmaceutical composition of the present disclosure may be variously prescribed according to factors such as formulation method, administration mode, a patient's age, weight, sex, pathological condition, food, administration time, administration route, excretion rate, and response sensitivity.

The pharmaceutical composition of the present invention can be administered orally or parenterally, and in the case of parenteral administration, the composition can be administered by topical application to the skin, intravenous injection, subcutaneous injection, intramuscular injection, intraperitoneal injection, transdermal administration, and the like.

The concentration of an active ingredient included in the composition of the present invention can be determined in consideration of the purpose of treatment, a patient's condition, the required period, and the like, and is not limited to a specific range of concentration.

The pharmaceutical composition of the present disclosure is prepared in a unit dosage form by formulation using a pharmaceutically acceptable carrier or excipient according to a method that can be easily carried out by a person of ordinary skill in the art to which the present disclosure pertains, or may be prepared by placing it in a multi-dose container. At this time, a formulation may be prepared as any one formulation selected from injections, creams, patches, sprays, ointments, plasters, lotions, liniments, pastas, and cataplasmas, and may further include a dispersing agent or a stabilizer.

The composition of the present invention can be added to functional foods for the purpose of improving intestinal function, preventing or improving an inflammatory disease along with collagen peptides obtained by culturing microorganisms. In the present invention, "functional food" refers to food mediating biological responses in disease prevention and treatment, biodefense, immunity, recovery after illness, and aging suppression, and should be harmless to the human body when taken for a long time.

When the composition of the present invention is used as a food additive, the composition may be added as it is or used together with other foods or food ingredients and may be appropriately used according to existing methods. The mixed amount of the active component can be suitably determined according to the purpose of use (prevention, health, or therapeutic treatment). In general, when preparing food or beverages, the composition of the present invention is added in an amount of 15% by weight or less, preferably 10% by weight or less, based on raw materials. However, long-term intake for health and hygiene or for health control may be below the above range, and the active ingredient may be used in an amount above the above range since there is no problem in terms of safety.

There is no particular limitation on the type of food that can include the composition of the present invention. Examples of foods to which the composition of the present invention can be added include meat, sausage, bread, chocolate, candies, snacks, confectioneries, pizza, ramen, other noodles, gums, ice cream, various soups, beverages, teas, drinks, alcohol drinks, vitamin complexes, and the like, and include all health foods in a conventional sense.

A health beverage composition of the present invention may include various flavoring agents or natural carbohydrates as additional components, like existing beverages. The natural carbohydrates may include monosaccharides such as glucose and fructose, disaccharides such as maltose and sucrose, natural sweeteners such as dextrin and cyclodextrin, and synthetic sweeteners such as saccharin and aspartame. The proportion of the natural carbohydrate is generally about 0.01 to 10 g, preferably about 0.01 to 0.1 g per 100 ml of the composition of the present invention.

In addition to the above, the composition of the present invention may include various nutrients, vitamins, electrolytes, flavors, colorants, pectic acid and salts thereof, alginic acid and salts thereof, organic acids, protective colloidal thickeners, pH adjusters, stabilizers, preservatives, glycerin, alcohol, carbonation agents used in carbonated beverages, and the like. In addition, the composition of the present invention may include fruit flesh for preparing natural fruit juices, fruit juice beverages, and vegetable beverages. These components may be used independently or in combination. The proportion of such additives is not critical but is generally selected in the range of 0.01 to 0.1 parts by weight per 100 parts by weight of the composition of the invention.

When the composition of the present invention is used as a feed additive, it may be used as a substitute for existing antibiotics to inhibit the growth of harmful intestinal bacteria, keep the intestinal flora stable to improve the health of livestock, improve livestock weight gain and meat quality, and increase milk production and immunity. At this time, it is preferable to include 1 to 20 parts by weight of the composition of the present invention based on 100 parts by weight of feed but is not limited thereto.

The feed additive, according to the present invention, may be prepared in the form of fermented feed, mixed feed, pellets and silage, and the like, but is not limited thereto. The fermented feed may be prepared by fermenting organic matter by adding various microorganisms or enzymes, and the mixed feed may be prepared by mixing various general feeds with the composition of the present invention. Feed in the form of pellets may be prepared by formulating the fermented feed or mixed feed using a pellet machine.

In the cosmetic composition according to one embodiment of the present invention, the cosmetic composition may be prepared in any one of the formulations selected from, but not limited to, solutions, suspensions, emulsions, pastes, gels, creams, lotions, powders, soaps, surfactant-containing cleansers, oils, powder foundations, emulsions, foundations, wax foundations, and sprays.

A cosmetic composition composed of each of these formulations may include various bases and additives necessary and appropriate for formulating the formulation, and the types and amounts of these components can be easily selected by those skilled in the art.

When a formulation of the cosmetic composition of the present invention is a paste, cream, or gel, a carrier component such as animal fiber, vegetable fiber, wax, paraffin, starch, tragacanth, cellulose derivatives, polyethylene glycol, silicone, bentonite, silica, talc, or zinc oxide can be used.

When the formulation of the cosmetic composition of the present invention is a powder or spray, lactose, talc, silica, aluminum hydroxide, calcium silicate, or polyamide powder may be used as a carrier component, and in particular, in the case of a spray, a propellant such as chlorofluorohydrocarbon, propane-butane, or dimethyl ether may be included.

When the formulation of the cosmetic composition of the present invention is a solution or emulsion, a solvent, solvating agent, or emulsifying agent is used as a carrier component, and these components may be water, ethanol, isopropanol, ethyl carbonate, ethyl acetate, benzyl alcohol, benzyl benzoate, propylene glycol, 1,3-butyl glycol oil, glycerol aliphatic esters, polyethylene glycol, or fatty acid esters of sorbitan.

When the formulation of the cosmetic composition of the present invention is a suspension, a liquid diluent such as water, ethanol, or propylene glycol, a suspending agent such as ethoxylated isostearyl alcohol, polyoxyethylene sorbitol ester, and polyoxyethylene sorbitan ester, microcrystalline cellulose, aluminum metahydroxide, bentonite, agar, tragacanth, or the like may be used as a carrier component.

When the formulation of the cosmetic composition of the present invention is a surfactant-containing cleanser, aliphatic alcohol sulfates, aliphatic alcohol ether sulfates, sulfosuccinic acid monoester, acethionate, imidazolinium derivatives, methyl taurate, sarcosinate, fatty acid amide ether sulfates, alkylamidobetaine, fatty alcohols, fatty acid glyceride, fatty acid diethanolamide, vegetable oil, lanolin derivatives, or ethoxylated glycerol fatty acid esters may be used as a carrier component.

The cosmetic composition of the present invention may further include excipients, including fluorescent substances, fungicides, hydrotropes, moisturizers, fragrances, fragrance carriers, proteins, solubilizers, sugar derivatives, sunscreens, vitamins, plant extracts, and the like.

In addition, another embodiment of the present invention provides a method of preparing collagen peptides having GPR35 activity, including: (1) culturing one or more microorganisms selected from *L. paracasei, L. plantarum*, and *L. salivarius*, which have collagen degrading activities in a collagen-containing medium to obtain a collagen hydrolysates, fractionating the collagen hydrolysates, and purifying the protein hydrolysate fractions into proteins and peptides; and (2) screening for physiological activities and analyzing the sequences of the purified peptides obtained in step (1) to obtain bioactive peptides derived from collagen.

Since a preparation method of the collagen peptide includes or uses the above-described composition as it is, the common content between the two is omitted.

The term "protein hydrolysate fractions" of the present invention means a product obtained by a fractionation method for separating a specific component or a specific group from a mixture including various components.

In the present invention, the protein hydrolysate fractions may be interpreted as a fraction obtained by applying the collagen peptide to various fractionation methods. The fraction of the extract can be obtained by applying the extract to various fractionation methods, and the fractionation method may include but is not limited to, a solvent fractionation method performed by treating various solvents, an ultrafiltration fractionation method performed by passing through an ultrafiltration membrane having a certain molecular weight cut-off value, and a chromatographic fractionation method that performs various types of chromatography (designed for separation according to size, charge, hydrophobicity or affinity), etc. In particular, the solvent used in the solvent fractionation method may include but is not limited to, a polar solvent or a non-polar solvent, and preferably the non-polar solvent. The solvent fractionation method may be performed by sequentially fractionating the extract using a solvent having a low non-polar level from a solvent having a high non-polar level, and for example, a method of sequentially fractionating the extract using nucleic acid or ethyl acetate may be used.

The fractionation in step (1) may be performed by ultrafiltration, and the pore size of an ultrafiltration membrane used for ultrafiltration in the present invention may be 10 kDa to 1 kDa. In addition, purification in step (1) may be performed by size-exclusion chromatography.

Screening for the physiological activity of the peptide in step (2) may be performed based on GPCR recruitment assay or analyzing peptide sequence in step (2) based on mass spectrometry.

In addition, another embodiment of the present invention provides collagen peptides consisting of an amino acid sequence selected from the group consisting of SEQ ID NOs: 1 to 174.

The collagen peptides may include, but are not limited to, one or more selected from the group consisting of amino acid sequences of SEQ ID NOs: 1 to 174 and modified amino acid sequences thereof.

Amino acid sequences of these collagen peptides are shown in Table 1 below.

TABLE 1

| SEQ ID NO | Amino acid sequence (NH$_2$--COOH) | Length | Molecular weight (kDa) |
|---|---|---|---|
| 1 | AIGA(Hyp)GAAGKD | 11 | 0.96 |
| 2 | VGPTGPAGPAG | 11 | 0.89 |
| 3 | GVAGPVG(Hyp)PGN | 11 | 0.95 |
| 4 | GLTGAAGDEGKR | 12 | 1.14 |
| 5 | PGPGPMGLMGPR | 12 | 1.18 |
| 6 | AGA(Hyp)GPAGATGA | 12 | 0.93 |
| 7 | (Hyp)G(Hyp)(Hyp)GPPGASGKE | 13 | 1.21 |
| 8 | PLG(Hyp)AGAAGRPGN | 13 | 1.16 |
| 9 | SGR(Hyp)GEAGLVGAR | 13 | 1.25 |
| 10 | PGPGPMGLMGPRG | 13 | 1.24 |
| 11 | GAIGA(Hyp)GAAGKDGD | 14 | 1.18 |
| 12 | GSPGS(Hyp)G(Hyp)DGKTGS | 14 | 1.24 |
| 13 | VVGGAGEKGEAGPA | 14 | 1.21 |
| 14 | GLSGPAGGKGERGN | 14 | 1.27 |
| 15 | GPAGASGPRGLTGD | 14 | 1.22 |
| 16 | PGPGPMGLMGPRGP | 14 | 1.33 |
| 17 | (Hyp)G(Hyp)(Hyp)GPPGASGKEG | 14 | 1.26 |
| 18 | IAG(Hyp)PGSTGPAGKD | 14 | 1.25 |
| 19 | SAG(Hyp)(Hyp)GF(Hyp)GA(Hyp)GPK | 14 | 1.31 |
| 20 | SGPLGPAGAAGR(Hyp)G | 14 | 1.19 |
| 21 | SKGMTGS(Hyp)GSPGPD | 14 | 1.30 |
| 22 | VMGAIGA(Hyp)GAAGKD | 14 | 1.24 |
| 23 | GETGPAGGRGSEGPQ | 15 | 1.37 |
| 24 | G(Hyp)AGQDGAAGPPGPA | 15 | 1.25 |
| 25 | GAAGPAGPRGPAGPA | 15 | 1.22 |
| 26 | GASGPAGPRGPVGVA | 15 | 1.26 |
| 27 | GIAG(Hyp)PGSTGPAGKD | 15 | 1.31 |
| 28 | GLTGAAGDEGKRGQT | 15 | 1.43 |
| 29 | GPAGARGA(Hyp)GPAGPR | 15 | 1.32 |
| 30 | AGPQGATGESGR(Hyp)GE | 15 | 1.40 |
| 31 | GEVGPQGGRGPEGPQ | 15 | 1.43 |
| 32 | GPQGEAGREGS(Hyp)GND | 15 | 1.46 |
| 33 | GPDGKTGSAGP(Hyp)GQD | 15 | 1.37 |
| 34 | SGPLGPAGAAGR(Hyp)GN | 15 | 1.31 |
| 35 | GPQGKEGPAGPSGQD | 15 | 1.39 |
| 36 | GPIGPRG(Hyp)SGPPGPD | 15 | 1.39 |

TABLE 1-continued

| SEQ ID NO | Amino acid sequence (NH₂--COOH) | Length | Molecular weight (kDa) |
|---|---|---|---|
| 37 | PGPGPMGLMGPRGPS | 15 | 1.42 |
| 38 | GG(Hyp)PGPTG(Hyp)RGQPGN | 15 | 1.39 |
| 39 | GPRGDVGPAGPQGEN | 15 | 1.42 |
| 40 | SGPKGPDGAPGKDGLR | 16 | 1.52 |
| 41 | AG(Hyp)PGPPG(Hyp)VGAGGPQ | 16 | 1.36 |
| 42 | (Hyp)GPAGAVGAQGPIGPR | 16 | 1.43 |
| 43 | TGPQGEAGREGS(Hyp)GND | 16 | 1.56 |
| 44 | ASG(Hyp)LGPAGAAGRPGN | 16 | 1.38 |
| 45 | PQGPAGASGPRGLTGD | 16 | 1.45 |
| 46 | PGPGPMGLMGPRGPSG | 16 | 1.48 |
| 47 | PGPAGAVGAQGPIGPR | 16 | 1.41 |
| 48 | GLIG(Hyp)PG(Hyp)SGERGAPG | 16 | 1.46 |
| 49 | AAG(Hyp)PGP(Hyp)GERGSTGSD | 17 | 1.55 |
| 50 | GAAGPPG(Hyp)VGPGGKEGQ | 17 | 1.46 |
| 51 | (Hyp)G(Hyp)PGPPGPAGIGEPF(Hyp) | 17 | 1.60 |
| 52 | SGPKGPDGAPGKDGLRG | 17 | 1.58 |
| 53 | GLIG(Hyp)PGITGL(Hyp)GARGE | 17 | 1.61 |
| 54 | SGPKGDAG(Hyp)(Hyp)GPPGPVG | 17 | 1.49 |
| 55 | GPQGPAGASGPRGLTGD | 17 | 1.51 |
| 56 | (Hyp)G(Hyp)(Hyp)GPPGASGKEGAKG | 17 | 1.52 |
| 57 | GASGPLG(Hyp)AGAAGRPGN | 17 | 1.43 |
| 58 | PGPAGAVGAQGPIGPRG | 17 | 1.47 |
| 59 | GPIGPRG(Hyp)SGPPGPDGN | 17 | 1.56 |
| 60 | GA(Hyp)GL(Hyp)G(Hyp)(Hyp)GPPGPAGIG | 18 | 1.54 |
| 61 | G(Hyp)AGQDGAAGPPGPAGSR | 18 | 1.55 |
| 62 | AGP(Hyp)GADGQ(Hyp)GAKGEAGD | 18 | 1.60 |
| 63 | AG(Hyp)(Hyp)GQDGR(Hyp)GPPGPVGA | 18 | 1.64 |
| 64 | GA(Hyp)GFQGL(Hyp)GPAGPVGET | 18 | 1.65 |
| 65 | GIRGLTG(Hyp)IGPPGPAGPQ | 18 | 1.67 |
| 66 | GLTGAAGDEGKRGQTGEQ | 18 | 1.74 |
| 67 | GLTGF(Hyp)GAAGRVGPPG(Hyp)A | 18 | 1.62 |

TABLE 1-continued

| SEQ ID NO | Amino acid sequence (NH₂--COOH) | Length | Molecular weight (kDa) |
|---|---|---|---|
| 68 | GEIGPAGPSGPAGPQGQR | 18 | 1.64 |
| 69 | IAGASGPLGPAGAAGR(Hyp)G | 18 | 1.50 |
| 70 | GSAGPQGKEGPAGPSGQD | 18 | 1.61 |
| 71 | GEAGPSGAVGPAGPAGAR | 18 | 1.49 |
| 72 | (Hyp)GPQGPAGASGPRGLTGD | 18 | 1.62 |
| 73 | AGASGPLGPAGAAGR(Hyp)GN | 18 | 1.51 |
| 74 | GA(Hyp)GPDGKAGPAGPAGDK | 18 | 1.55 |
| 75 | AGL(Hyp)GPAGPPGEPGPAG(Hyp)T | 19 | 1.64 |
| 76 | SGPAGPAGPSGPRGPAGPS | 19 | 1.59 |
| 77 | GPPGAAGEKGEPGPVG(Hyp)AG | 19 | 1.63 |
| 78 | PGPGPMGLMGPRGPSGPPG | 19 | 1.73 |
| 79 | IAGASGPLGPAGAAGR(Hyp)GN | 19 | 1.62 |
| 80 | ATGF(Hyp)GAAGRLGPPG(Hyp)AGN | 19 | 1.71 |
| 81 | G(Hyp)GPQGPAGASGPRGLTGD | 19 | 1.68 |
| 82 | PGPAGASGPAGPRGPVGVA | 19 | 1.58 |
| 83 | GFAG(Hyp)PGADGQ(Hyp)GAKGEAGD | 20 | 1.80 |
| 84 | GSAG(Hyp)PGQDGR(Hyp)GPPG(Hyp)VGA | 20 | 1.79 |
| 85 | SGPAGPAGPSGPRGPAGPSG | 20 | 1.64 |
| 86 | AVGAQGPIGPRGPSG(Hyp)PGPD | 20 | 1.81 |
| 87 | GIAGASG(Hyp)LGPAGAAGRPGN | 20 | 1.68 |
| 88 | AGA(Hyp)GPAGATGAPGPQG(Hyp)VG | 20 | 1.63 |
| 89 | GGPGPQG(Hyp)AGASGPRGLTGD | 20 | 1.73 |
| 90 | GARGDAGAAGV(Hyp)GGVGSAGPQ | 21 | 1.74 |
| 91 | GARGS(Hyp)GAAGNDGARGDAGAA | 21 | 1.78 |
| 92 | GKAGPAG(Hyp)AGQDGAAGPPGPA | 21 | 1.73 |
| 93 | GSPGAPG(Hyp)DGKAGPAG(Hyp)AGQD | 21 | 1.80 |
| 94 | GFTGPAGE(Hyp)GEPGPSGPMGPR | 21 | 1.98 |

TABLE 1-continued

| SEQ ID NO | Amino acid sequence (NH₂--COOH) | Length | Molecular weight (kDa) |
|---|---|---|---|
| 95 | GA(Hyp)GPPGAAGEKGEPG (Hyp)VGPA | 21 | 1.81 |
| 96 | GAVGPAG(Hyp)AGARGAPGP AGPR | 21 | 1.77 |
| 97 | GISGPSGLIG(Hyp)PGITGL (Hyp)GAR | 21 | 1.92 |
| 98 | GLMGPRGPSGPPGAPGPQGLQ | 21 | 1.94 |
| 99 | GLMGPRG(Hyp)SGPPGAPGP QGLQ | 21 | 1.96 |
| 100 | GSPGAPG(Hyp)DGKAGPAG (Hyp)AGDK | 21 | 1.80 |
| 101 | GSPGSPG(Hyp)DGKTGSAG (Hyp)(Hyp)GQD | 21 | 1.88 |
| 102 | GFTGPPGE(Hyp)GEAGASGP MGPR | 21 | 1.95 |
| 103 | PSGEPGPAGASGPAGPRGPVG | 21 | 1.78 |
| 104 | GE(Hyp)GMPGSKGMTGSPGS (Hyp)GPD | 21 | 1.94 |
| 105 | IGL(Hyp)GMTGPQGEAGREG SPGN | 21 | 2.01 |
| 106 | DGARGDAGAAGV(Hyp)GGVG SAGPQ | 22 | 1.85 |
| 107 | GA(Hyp)GL(Hyp)GPPGPPG PAGIGE(Hyp)F(Hyp) | 22 | 2.01 |
| 108 | SGMAGLPGPAGPPGE(Hyp)G PAGPT | 22 | 1.90 |
| 109 | SGPAGPAGPSGPRGPAGPSGP A | 22 | 1.81 |
| 110 | SGPAGPAGAAGPAGPRGPAGP A | 22 | 1.75 |
| 111 | SGG(Hyp)GEAGREGS(Hyp) GHDGA(Hyp)GRD | 22 | 2.08 |
| 112 | IGL(Hyp)GMTGPQGEAGREG SPGND | 22 | 2.12 |
| 113 | PRGGPGPQGPAGASG(Hyp)R GLTGD | 22 | 1.99 |
| 114 | GETG(Hyp)AGGRGSEGPQGA RGEPGN | 23 | 2.12 |
| 115 | NDGARGDAGAAGV(Hyp)GGV GSAGPQ | 23 | 1.97 |
| 116 | GFTGPPGE(Hyp)GEAGASGP MGPRGA | 23 | 2.08 |
| 117 | GISGPSGLIG(Hyp)PGITGL (Hyp)GARGE | 23 | 2.10 |
| 118 | GKTGSAG(Hyp)(Hyp)GQDG RPG(Hyp)PGPVGA | 23 | 2.07 |
| 119 | G(Hyp)(Hyp)G(Hyp) (Hyp)GPPGPPGPSGGGFDIG F | 23 | 2.09 |
| 120 | GPSGQDGRGGPPGPTG(Hyp) RGQPGN | 23 | 2.13 |

TABLE 1-continued

| SEQ ID NO | Amino acid sequence (NH₂--COOH) | Length | Molecular weight (kDa) |
|---|---|---|---|
| 121 | GA(Hyp)GR(Hyp)GEVGAAG PPG(Hyp)(Hyp)GERGST | 24 | 2.20 |
| 122 | GARGEPGNPGPGGAAG(Hyp) (Hyp)G(Hyp)PGSD | 24 | 2.09 |
| 123 | GNDGARGDAGAAGV(Hyp)GG VGSAGPQ | 24 | 2.02 |
| 124 | G(Hyp)AGQDGAAGPPGPAGS RGLPGVM | 24 | 2.10 |
| 125 | AVPGPMGPMGPRGPPGPPGLS GPQ | 24 | 2.22 |
| 126 | GKEGPAG(Hyp)SGQDGRGGP PGPTGPR | 24 | 2.21 |
| 127 | GMPGPSGPSGDSGPAGPAGPS GPR | 24 | 2.06 |
| 128 | GEIGPAG(Hyp)SGPAGPQGQ RGEPGTN | 24 | 2.22 |
| 129 | GL(Hyp)GSPGSAGPQGKEG (Hyp)AGPSGQD | 24 | 2.15 |
| 130 | TG(Hyp)AGPAGPLGSAGP (Hyp)GF(Hyp)GAPGPK | 25 | 2.17 |
| 131 | (Hyp)GPAGAVGAQGPIGPRG PSGPPGPD | 25 | 2.19 |
| 132 | (Hyp)GPAGAVGAQGPIGPRG (Hyp)SGPPGPD | 25 | 2.21 |
| 133 | GA(Hyp)GL(Hyp)GPPGPPG PAGIGE(Hyp)F(Hyp)IIPQ | 26 | 2.46 |
| 134 | ALAVPGPMGPMGPRGPPGPPG LSGPQ | 26 | 2.40 |
| 135 | GIRGLTG(Hyp)IGPPGPAGP QGDKGEPGA | 26 | 2.38 |
| 136 | GPPGAAGEKGEPGPVG(Hyp) AGSTGPRGG | 26 | 2.24 |
| 137 | GF(Hyp)GPRGG(Hyp)GPQG PAGASGPRGLTGD | 26 | 2.36 |
| 138 | GA(Hyp)GL(Hyp)GPPGPPG PAGIGE(Hyp)F(Hyp)IIPQ P | 27 | 2.56 |
| 139 | GA(Hyp)GR(Hyp)GEVGAAG PPG(Hyp)(Hyp)GERGSTGS D | 27 | 2.46 |
| 140 | GF(Hyp)GAAGRVGPPGPAGA AG(Hyp)(Hyp)GPVGPG | 27 | 2.28 |
| 141 | GL(Hyp)GPAGPPGEPGPAG (Hyp)TGPAGPRGPS | 27 | 2.35 |
| 142 | GLTG(Hyp)IGPPGPAGPQGD KGEPGAAGPL | 27 | 2.39 |
| 143 | GMPGPSGPSGDSGPAGPAGPS GPRGPA | 27 | 2.28 |
| 144 | GNTG(Hyp)AGPAGPLGSAG (Hyp)(Hyp)GFPGAPGPK | 27 | 2.34 |

TABLE 1-continued

| SEQ ID NO | Amino acid sequence (NH₂--COOH) | Length | Molecular weight (kDa) |
|---|---|---|---|
| 145 | GA(Hyp)GRPGEVGAAGPPG (Hyp)(Hyp)GERGSTGSD | 27 | 2.45 |
| 146 | AGLPGPAGPPGEPGPAG (Hyp)TGPAGPRGPS | 28 | 2.40 |
| 147 | AGL(Hyp)GPAGPPGEPGPAG (Hyp)TG(Hyp)AGPRGPS | 28 | 2.43 |
| 148 | AGL(Hyp)GPAGPPGEPGPAG (Hyp)TGPAGPRGPS | 28 | 2.42 |
| 149 | GA(Hyp)GL(Hyp)G(Hyp)P GPPGPAGIGE(Hyp)F(Hyp) IIPQPE | 28 | 2.71 |
| 150 | GA(Hyp)GL(Hyp)GPPGPPG PAGIGE(Hyp)FPIIPQPE | 28 | 2.67 |
| 151 | GA(Hyp)GL(Hyp)GPPGPPG PAGIGE(Hyp)F(Hyp)IIPQ PE | 28 | 2.69 |
| 152 | DGAAGAAG(Hyp)PGPTGPAG (Hyp)(Hyp)GF(Hyp)GGPG AK | 28 | 2.36 |
| 153 | G(Hyp)AG(Hyp)QGATGESG RPGE(Hyp)GLPGSRGVSG | 28 | 2.55 |
| 154 | GA(Hyp)GL(Hyp)GPPGPPG PAGIGE(Hyp)F(Hyp)IIPQ PEK | 29 | 2.82 |
| 155 | GA(Hyp)GFQGL(Hyp)G (Hyp)AGPVGETGKPGDRGI (Hyp)GD | 29 | 2.73 |
| 156 | GEIG(Hyp)AGPPGPPGPPG (Hyp)(Hyp)G(Hyp)SGGGF DIGF | 29 | 2.62 |
| 157 | GGAALAVPGPMGPMGPRGPPG PPGLSGPQ | 29 | 2.59 |
| 158 | GKEGPAGPSGQDGRGG(Hyp) (Hyp)GPTGPRGQPGN | 29 | 2.68 |
| 159 | LTG(Hyp)IGPPGPAGPQGDK GEPGAAGPLGPT | 29 | 2.59 |
| 160 | SAG(Hyp)(Hyp)GFPGPAGP KGEIG(Hyp)AGPSGPAGPQ | 29 | 2.57 |
| 161 | GA(Hyp)GL(Hyp)GPPGPPG PAGIGE(Hyp)F(Hyp)IIPQ PEKA | 30 | 2.89 |
| 162 | GF(Hyp)GAAGRVGPPGPAGA AG(Hyp)(Hyp)GPVGPGGKE | 30 | 2.60 |
| 163 | GFTGPAGEPGEPGPSG(Hyp) MG(Hyp)RGPIGPPGRN | 30 | 2.84 |
| 164 | GKAGPAG(Hyp)AGQDGAAGP PGPAGSRGLPGVM | 30 | 2.58 |
| 165 | GMAGLPGPAGPPGEPG(Hyp) AGPTGPAGPRGPS | 30 | 2.59 |
| 166 | GAAG(Hyp)PGKNGEDGESGK (Hyp)GR(Hyp)GERGPPGPQ | 30 | 2.87 |
| 167 | GAPGLRG(Hyp)(Hyp)GPDG NNGPAGPVGVVGGAGEK | 30 | 2.65 |

TABLE 1-continued

| SEQ ID NO | Amino acid sequence (NH₂--COOH) | Length | Molecular weight (kDa) |
|---|---|---|---|
| 168 | GAPGLRG(Hyp)PGPDGNNGP AGPVGVVGGAGEK | 30 | 2.64 |
| 169 | GF(Hyp)GAAGRVGPPGPAGI AG(Hyp)(Hyp)GSTGPAGKD | 30 | 2.63 |
| 170 | GIRGLTGPIGPPGPAG(Hyp) QGDKGEPGAAGPL | 30 | 2.72 |
| 171 | GLTGF(Hyp)GAAGRVGPPG (Hyp)AGIAG(Hyp)PGSTGP A | 30 | 2.60 |
| 172 | GLTG(Hyp)IGPPGPAGPQGD KGEPGAAGPLGPT | 30 | 2.65 |
| 173 | GMPGPSGPSGDSGPAGPAGPS GPRGPAGPS | 30 | 2.53 |
| 174 | RGE(Hyp)GAPG(Hyp)LGIA GASG(Hyp)LGPAGAAGRPGN | 30 | 2.64 |

(Hyp) in the amino acid sequence of Table 1 means hydroxyproline.

The peptides represented by SEQ ID NOs: 1 to 174 are amino acid sequences identified using liquid chromatography-tandem mass spectrometry (LC-MS/MS) for the collagen peptides, which promote wound healing and relieve inflammation, prepared by the preparation method of collagen peptides of the present invention. More specifically, the peptide sequences can be analyzed using a database built on the basis of a sequence of collagen as a target material and proteomic sequences of strains capable of degrading collagen, such as *L. paracasei*, *L. plantarum*, and *L. salivarius* strains, and using a non-specific digestion method, and the peptide can be synthesized using a conventional technique in the art based on the sequence obtained by identifying the peptide by performing the LC/MS-MS method on the database. Since the peptide has a molecular weight of 1 kDa to 10 kDa or less and activates GPR35 to promote wound healing and relieve inflammation, the peptide can be usefully used to improve intestinal function or prevent or improve inflammatory diseases.

The modified amino acid sequence may be maintained without changing the main activity or exhibit improved activity and may include those in which a portion of the amino acid sequence may be mutated due to natural or artificial mutation or one or more of the amino acids constituting the amino acid sequence substituted with other types of amino acids. Specifically, in the modified amino acid sequence, one or more of the amino acids constituting the amino acid sequences 1 to 9 may be substituted with one or more selected from the group consisting of gamma-aminobutyric acid, glutamine (Gln, Q), glutamic acid (Glu, E), glycine (Gly, G), lysine (Lys, K), leucine (Leu, L), methionine (Met, M), (Val, V), serine (Ser, S), selenomethionine, selenocysteine (Sec, U), cysteine (Cys, C), citrulline, arginine (Arg, R), asparagine (Asn, N), aspartic acid (Asp, D), alanine (Ala, A), ornithine, isoleucine (Ile, I), taurine, threonine (Thr, T), tryptophan (Trp, W), tyrosine (Tyr, Y), phenylalanine (Phe, F), proline (Pro, P), pyrrolysine (Pyr, O), histidine (His, H), and unnatural amino acids. Peptides, according to one embodiment of the present invention, may include a peptide exhibiting 80% or more, 85% or more, 90% or more, 91% or more, 92% or more, 93% or more, 94% or more, 95% or more, 96% or more, 97% or more, 98% or more, or 99% or more homology to the amino acid sequence, as well as SEQ ID NOs described above, as long as they have the same or corresponding biological activity as each peptide. When a sequence having homology to the above sequence is an amino acid sequence having biological activity substantially identical to or corresponding to that of the peptide of a SEQ ID NO described above, it is apparent that cases in which some sequences have deleted, modified, substituted or added amino acid sequences are also included in the scope of the present application.

As used throughout this specification, the term "homology" refers to the degree of identity with a given amino acid sequence or polynucleotide sequence and can be expressed as a percentage. As used herein, a homologous sequence having the same or similar activity as a given amino acid sequence or polynucleotide sequence is indicated by "% homology". For example, sequences can be compared and identified using standard software, specifically BLAST 2.0, which calculates parameters such as score, identity, similarity, etc., or by hybridization experiments performed under defined stringent conditions, and appropriate hybridization conditions, as defined, are within the skill of the art and can be determined by a method [for example, J. Sambrook et al., Molecular Cloning, A Laboratory Manual, 2nd Edition, Cold Spring Harbor Laboratory Press, Cold Spring Harbor, New York, 1989; F. M. Ausubel et al., Current Protocols in Molecular Biology, John Wiley & Sons, Inc., New York] well known to those skilled in the art.

As used throughout the specification of the present invention, the term "relieving inflammation" refers to an action of inhibiting or reducing inflammation, and the term "inflammation" is a defensive reaction that occurs in the body when living tissue is damaged and is a cause of inflammatory diseases. Therefore, the peptide for relieving inflammation of the present specification can be used for prevention, treatment, or improvement (relief of symptoms) of inflammatory diseases by exhibiting an activity of inhibiting or reducing inflammation.

BRIEF DESCRIPTION OF THE DRAWINGS

The above and other objects, features, and advantages of the present disclosure will become more apparent to those of ordinary skill in the art by describing in detail exemplary embodiments thereof with reference to the accompanying drawings, in which:

FIG. 3A is a diagram showing the SDS-PAGE analysis of collagen hydrolysates produced from anaerobic fermentation of *L. salivarius;*

FIG. 3B is a diagram showing the SDS-PAGE analysis of collagen hydrolysates produced from anaerobic fermentation of *L. plantarum;*

FIG. 3C is a diagram showing the SDS-PAGE analysis of collagen hydrolysates produced from anaerobic fermentation of *L. paracasei;*

FIG. 3D is a diagram showing the SDS-PAGE analysis of collagen hydrolysates produced from anaerobic fermentation of *L. delbrueckii;*

FIG. 4A is a diagram showing the size-exclusion chromatography profiles of crude and <10 kDa collagen hydrolysates produced by *L. plantarum* that showed collagen degrading ability;

FIG. 4B is a diagram showing the size-exclusion chromatography profiles of crude and <10 kDa collagen hydrolysates produced by *L. paracasei* that showed collagen degrading ability;

FIG. 4C is a diagram showing the size-exclusion chromatography profiles of crude and <10 kDa collagen hydrolysates produced by *L. salivarius* that showed collagen degrading ability;

FIG. 5A shows the mass spectrometric analysis of peptides produced by *Lactobacilluseae* species: *L. paracasei, L. plantarum* and *L. salivarius* produce a source of peptides identified in collagen hydrolysates;

FIG. 5B is the number of peptides identified in collagen hydrolysates produced by three species of *Lactobacilluse;*

FIG. 5C is the distribution of peptide molecular weights (MWs) and isoelectric points (pIs) identified in three species of *Lactobacilluseae;*

FIG. 5D is a diagram showing a differential distribution of peptides for representative collagen protein "collagen alpha-2 (I) chain isoform X2" (SEQ ID NO: 175, accession number XP_026771581);

FIG. 5E represents the sequence logo of the peptide cleavage pattern. Sequence logo representations of collagen cleavage sites were visualized by implementing the ggseqlogo package in R, which is provided free of charge in the Github repository;

FIG. 6A is a diagram showing collagen peptides as potential GPR35 agonistic ligands. It is an experimental scheme to identify potential bioactive peptides in collagen hydrolysates based on functional screening and peptide identification;

FIG. 6B is a heatmap of individual agonist assays for 168 G protein-coupled receptors (GPCRs);

FIG. 6C is a functional screening procedure for identifying potential GPCRs using collagen peptides as ligands;

FIG. 6D is a diagram showing GPR35 activation by *L. paracasei* and *L. plantarum* collagen peptides as measured in relative light units (RLU);

FIG. 7 is a diagram showing the cytotoxicity of collagen peptide fractions in Caco-2 cells;

FIG. 8A is a diagram showing the effect of collagen peptides on GPR35-induced wound healing. It shows a wound-healing effect of *L. plantarum* and *L. paracasei* collagen peptide fractions in Caco-2 cells;

FIG. 8B is a diagram showing the effect of collagen peptides on GPR35-induced wound healing. It shows a relative wound closure rate (%) of FIG. 8A;

FIG. 8C is a diagram showing the effect of collagen peptides on GPR35-induced wound healing. It shows the effect of collagen peptide fractions on an ERK1/2 signaling pathway in Caco-2 cells;

FIG. 9A is a diagram showing the degree of inhibition of inflammatory cytokine and gene expressions of enzymes by the collagen peptide fraction in intestinal epithelial cells. It shows the relative mRNA expression level of interleukin (IL)-6;

FIG. 9B is a diagram showing the degree of inhibition of inflammatory cytokine and gene expressions of enzymes by the collagen peptide fraction in intestinal epithelial cells. It shows the level of IL-8; and FIG. 9C is a diagram showing the degree of inhibition of inflammatory cytokine and gene expressions of enzymes by the collagen peptide fraction in intestinal epithelial cells. It shows the level of cyclooxygenase-2 (COX-2).

DETAILED DESCRIPTION OF EXEMPLARY EMBODIMENTS

Figure 1:
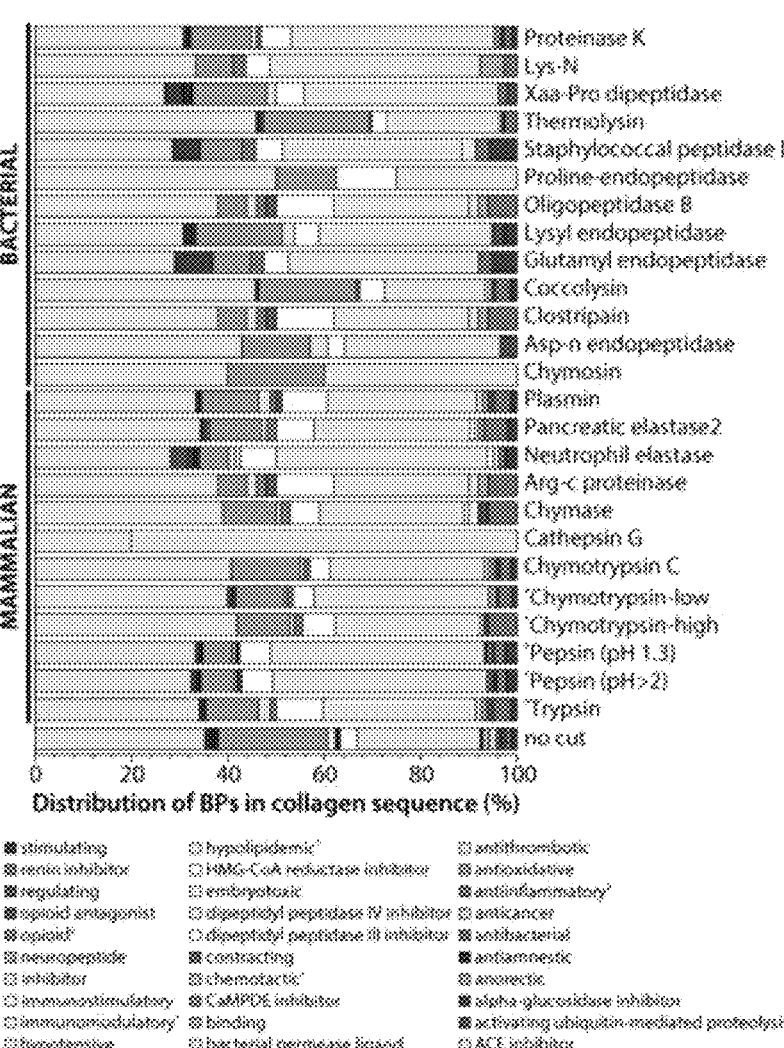
FIG. 1 is a diagram showing differential profiles of potential bioactive peptides released through in silico protein digestion by mammalian and bacterial proteases. The distribution of collagen-derived bioactive peptides released by 25 proteases is shown, and * is a human digestive enzyme. † represents the potential physiological activity that can be specifically found by a protease of bacterial origin, and ‡ represents the potential physiological activity that can be specifically found by a protease of mammalian origin.

Hereinafter, the present invention will be described in more detail through examples. These examples are only for illustrating the present invention, and it will be apparent to those of ordinary skill in the art that the scope of the present invention is not to be construed as being limited by these examples.

EXAMPLE

Experiment Preparation and Method
Bacterial Strains and Culture Conditions

10 *Lactobacilluseae* strains were obtained from the Korean Culture Center of Microorganisms (KCCM). The *Lactobacilluseae* strains were individually cultured in an anaerobic serum bottle sealed with a butyl-rubber stopper at 37° C. with a gas mixture of 10% $CO_2$, 10% $H_2$, and 80% $N_2$.

Lactic acid bacteria (LAB) were activated in Difco™ Lactobacilli MRS Broth and transferred to a defined pre-culture medium. In the late exponential phase of bacterial growth, bacteria from the pre-culture medium were transferred to a main culture medium and cultured for 48 hours. Optical density was measured at 600 nm (OD600) using a spectrophotometer (Biochrom Libra S70, UK), and bacterial growth was monitored by direct cell counting using a Neubauer chamber (depth, 0.1 mm×area, 0.0025 mm$^2$; Paul Marienfeld GmbH, Germany) with a phase-contrast microscope (Olympus BX43, Olympus LS, Japan).
Defined Medium Composition Characterization of bacterial growth of *Lactobacillus* species was performed on Defined Media (DM) adapted from Sanguir et al. *Lactiplantibacillus plantarum* KCTC 3108, *Lacticaseibacillus rhamnosus* KCTC 3237, *Lacticaseibacillus paracasei* KCTC 3510, *Lacticaseibacillus casei* KCTC 3109, and *Limosilactobacillus fermentum* KCTC 3112 were cultured in DM. *Ligilactobacillus salivarius* KCCM 40989 was cultured in DM with twice the amino acid concentration (DM2). *Limosilactobacillus reuteri* KCCM 40717 was cultured in DM supplemented with 0.1% yeast extract (DM3). *Lactobacillus delbrueckii* KCTC 3635 was cultured in DM supplemented with 0.5% yeast extract (DM4). *Lactobacillus acidophilus* KCCM 32820 and *Lactobacillus* gasseri KCTC 3163 were cultured in 1/5×MRS. The collagen degrading activities of the *Lactobacilluseae* species were measured using corresponding defined media supplemented with 0.5% collagen (DMC).
Purification of Collagen Peptide After incubation for 48 hours, bacterial cultures were centrifuged at 8,000×g for 20 minutes at 4° C. The volume of a cell-free supernatant was concentrated almost 20-fold by heat treatment in an oven at 70° C. for 18-22 hours. The concentrated supernatant was then centrifuged at 10,000×g for 1 hour at 4° C. to remove a precipitate. The resulting supernatant was filtered through a 0.2 μm membrane. Next, the filtrate was fractionated by ultrafiltration using a 10 kDa cutoff disk (Millipore, U.S.A.) to obtain high molecular weight (HMW, >10 kDa) and low molecular weight (LMW, <10 kDa) peptides, which were then lyophilized. The fractionated hydrolysate (50 mg) was dissolved in 20 mM Tris-HCl (pH 7.0). Fractions were then loaded onto a Superdex 30 prep grade column (90 mL) equilibrated with the same buffer in a Biologic Duo-Flow FPLC system (Bio-Rad, USA) at 1.5 mL/min. Based on a standard curve, fractions corresponding to 1-10 kDa were obtained and lyophilized.
GPCR β-Arrestin Assay GPCR binding activity was measured by Eurofins DiscoverX using the PathHunter® β-Arrestin Assay. A 1-10 kDa peptide fraction (1 mg/mL) was screened in a cell-based assay of 168 GPCRs using β-arrestin recruitment. Samples were tested for agonistic activation of GPCRs in cells derived from Chinese Hamster Ovary-K1, U2OS and Human Embryonic Kidney 293. After cells were inoculated and incubated at 37° C., responses were induced by treatment with samples or agents. A PathHunter detection reagent cocktail was added to generate signals, and luminescence values were measured. Data were expressed as a percentage of the control ligand. All experiments were performed in duplicate.
Peptide Identification Using LC-MS/MS Collagen peptides from three species of *Lactobacilluseae* were analyzed by reverse-phase HPLC-ESI-MS/MS using a Nano LC-2D Ultra system (Eksigent, Dublin, CA, USA) coupled to a nano-ESI LTQ-XL mass spectrometer (Thermo Fisher Scientific, Bremen, Germany). Peptide (3 μg) was loaded onto a trap column (ID 75 μm; New Objective IntegraFrit, Scientific Instrument Services, Inc., Ringoes, NJ, USA) and eluted with an analytical column (ID 75 μm, OD 375 μm; Molex Polymicro Technologies) at a flow rate of 0.4 μL/min. Both columns were packed in-house with ReproSil-Pur 200 C18-AQ 5 μm particles (Dr. Maisch GmbH, Germany). A mobile phase consisted of 0.1% FA (v/v) in water (solvent A) and 0.1% FA (v/v) in ACN (solvent B). Gradient parameters were 0-1 min (2%-5% solvent B), 1-62 min (5%-35% solvent B), 62-65 min (35%-60% solvent B), 65-67 min (60% solvent B), 67-70 min (60%-2% solvent B), and 70-90 min (2% solvent B), with a total run time of 90 min (or 60 min for a steeper gradient). MS analysis of the peptide eluate was performed on an LTQ-XL linear ion trap mass spectrometer (Thermo Fisher Scientific, U.S.A.) in a positive ion mode with a nano-ion spray voltage of 1.8 kV and an interface heater temperature of 200° C. The normalized collision energy was set at 35% for MS/MS analysis.

Peptides were analyzed using an UltiMate 3000 RSLC nano system (retention time RSD<0.2%) coupled to a Q-Exactive Orbitrap HF-X mass spectrometer (Thermo Fisher Scientific). Peptide (2 μg) was loaded onto a trap column (ID=75 μm×2 cm, packed with Acclaim PepMap 100 C18, 3 μm, 100 Å; Thermo Fisher Scientific), and eluted with an analytical column (ID=75 μm×50 cm, packed with PepMap RSLC C18, 2 μm, 100 Å; Thermo Fisher Scientific) at a flow rate of 0.27 μL/min. Mobile phase A for LC separation was 0.1% FA in deionized water, and mobile phase B was 0.1% FA in ACN. Chromatographic gradients were 0-5 min (5%-10% solvent B), 5-70 min (10%-35% solvent B), 70-80 min (35%-50% solvent B), 80-85 min (50%-80% solvent B), 85-90 min (80% solvent B), and 90-95 min (80%-5% solvent B). For tandem mass spectrometry, mass spectra were acquired using data-dependent acquisition with full mass scans (400-2000 m/z) followed by MS/MS scans. A spray voltage was 1.8 kV, and a heated capillary temperature was 250° C. The normalized collision energy was set at 27% for MS/MS analysis.

Data Analysis

An integrated tool from PeptideShaker was used. MSConvert (ProteoWizard) was used to first process the MS and MS/MS spectra and convert the raw data to peak lists (.mgf format). A processed spectrum was compared with a collagen sequence of *Pangasianodon hypophthalmus* (SEQ ID NO:175) and a proteomic sequence of three species of *Lactobacilluseae* (*L. paracasei* JCM 8130 [National Center for Biotechnology Information (NCBI) GenBank assembly accession GCA_000829035.1], *L. plantarum* DSM 20174 (GCA_014131735.1), or *L. salivarius* BCRC 12574 (GCA_002735985.1)) using a target decoy database search strategy. For MS-GF+ searches, the oxidation of methionine and proline was set to a variable modification. For LTQ-XL, an m/z tolerance for precursor and fragment was set to 4.0 Da and 1.0 Da, respectively. A list of peptides with a false discovery rate (FDR) of less than 0.01 (1%) was obtained. Physicochemical properties of the peptides were confirmed from MS spectral data (mass) or predicted using an in silico tool [IPC 2.0, Isoelectric Point (pI) Prediction] (http://ipc2.mimuw.edu.pl/). Sequence logo representation of a collagen cleavage site was visualized by implementing the ggseqlogo package in R, which is provided free of charge in the Github repository.

Cell Culture and MTT Assay

Caco-2 cells, a human colon epithelial cell line, were obtained from the American Type Culture Collection (ATCC, Manassas, Va.). Caco-2 cells were cultured at 37° C. in an atmosphere containing 5% $CO_2$ in Eagle's Minimum Essential Medium (EMEM) supplemented with 20% fetal bovine serum and penicillin/streptomycin. To evaluate cell viability, Caco-2 cells were incubated with *L. plantarum* and *L. paracasei* collagen peptide fractions (0, 0.01, 0.1, 1, or 10 mg/mL) or the same fraction of medium in which strains were not cultured. After 48 hours, 20 µL of 5 mg/mL thiazolyl blue tetrazolium bromide (MTT) was added to each well and incubated for 2 hours. Then, the culture medium was removed, and 200 µL of dimethyl sulfoxide was added to dissolve MTT formazan crystals for 30 minutes. Absorbance was measured at 570 nm using a microplate reader (Sunrise-Basic Tecan, Grodig, Austria). Cell viability was analyzed by a Student's t-test, and statistical significance was shown when $P<0.05$ compared to an untreated group (*, $P<0.05$; , $P<0.01$; *, $P<0.001$).

Analysis of Wound Healing Activities and Mechanism of Action

Caco-2 cells were pre-incubated with 0.1 µM CID 2745687 (Tocris Bioscience, Bristol, UK) or 10 µM PD98059 (Cell Signaling Technology, Danvers, MA) for 1 hour in EMEM. CID 2745687 and PD98059 were used to selectively inhibit GPR35 and mitogen-activated protein kinase (MEK1/2) involved in the ERK1/2 signaling pathway, respectively. The cells were then scratched to create a wound in a cell monolayer. Detached cells were washed with phosphate-buffered saline and then incubated for 48 hours in a serum-free medium including 20 µg/mL collagen peptide fraction, 20 ng/mL human epidermal growth factor (EGF; Sigma-Aldrich, St. Louis, MO), or 2 µM zaprinast (Tocris Bioscience). Wound images were observed under a microscope at 24-hour intervals from 0 hour. Wound width was quantified using Image Plus 3.0 ML software (Motic, Vancouver, Canada), and the relative wound closure rate was calculated as a relative difference in wound width and expressed as a percentage of control. The relative wound closure rate was analyzed by a Student's t-test, and the test shows * (when $P<0.05$),  (when $P<0.01$), and * (when $P<0.001$), compared to an untreated group; and #(when $P<0.05$), ##(when $P<0.01$), and ###(when $P<0.001$), compared to an inhibitor-treated group. ERK1/2 phosphorylation was evaluated to identify the signaling pathway downstream of GPR35. Cells were pre-treated for 1 hour with or without CID 2745687 (0.1 µM) and incubated for 5 minutes in the presence or absence of a collagen peptide fraction (20 µg/mL), the same fractions of DMC (20 µg/mL) or positive control (20 ng/mL EGF or 2 µM zaprinast). Western blot analysis was performed to evaluate ERK1/2 phosphorylation.

Inflammation-Related Gene Expression Level Analysis

The mRNA expression levels of IL-6, IL-8, and COX-2 in Caco-2 were evaluated by real-time PCR. More specifically, Caco-2 cells were co-treated with 1 µg/mL lipopolysaccharide (LPS), an inflammation-inducing substance, and collagen peptide fractions (10 or 20 µg/mL) produced by *L. plantarum* or *L. paracasei*, or a same fraction (10 or 20 µg/mL) of a strain-free medium, and then cultured for 12 hours under conditions of 37° C. and 5% $CO_2$. To measure mRNA expression levels, Caco-2 cells were harvested, mRNA was extracted and purified using an RNA extraction kit (RNeasy mini kit, QIAGEN, U.S.A.), and cDNA was synthesized using a cDNA synthesis kit (iScript™ cDNA Synthesis Kit, BIO-RAD, U.S.A.), and real-time PCR was performed using target primers for each gene. The expression levels of IL-6, IL-8, and COX-2 mRNA were normalized to an expression level of actin mRNA, a housekeeping gene, and expressed as relative expression levels to a group treated only with LPS. A relative expression level of the gene was analyzed by a Student's t-test, and statistical significance was shown when $P<0.05$ compared to an LPS treatment group (*, $P<0.05$; , $P<0.01$; *, $P<0.001$).

Example 1: In Silico Analysis of Potential Bioactive Peptides Derived from Collagen To investigate potential bioactive peptides included in collagen, 238 collagen FASTA sequences were extracted from the genome of *Pangasianodon hypophthalmus*. Using an online BIOPEP database, the bioactive peptides included in collagen sequences were extracted using a "potential biological activity profile" tool. A total of 1157 putative bioactive peptides were identified, and their functional roles ranged from ACE inhibitors to neuropeptides (FIG. 1). Additionally, collagen sequences were subjected to in silico proteolysis using the information on the substrate specificity of the P1 site of widely studied proteases. Protease cleavage information was obtained from Expasy Peptide Cutter and BIOPEP. There have been 30 types of functional bioactive peptides encoded in collagen sequences, ranging from ACE inhibitors to embryotoxic peptides. Upon digestion with 25 different proteases, bioactive peptides with 30 different physiological activities were released through mammalian and bacterial protease activities. In particular, there was a distinct difference between the BPs specifically released by bacterial proteases and mammalian proteases. For example, inflammation-relieving peptides are exclusively released using bacterial proteases, whereas immunomodulatory peptides are specifically produced only when digested with digestive enzymes. Additionally, human gastrointestinal enzymes were highlighted (*) to predict how collagen might be broken down within the digestive system. In silico protein digestion shows that human gastrointestinal enzymes such as trypsin, chymotrypsin, and pepsin produce BPs that cannot be produced by bacterial proteases.

Figure 2:
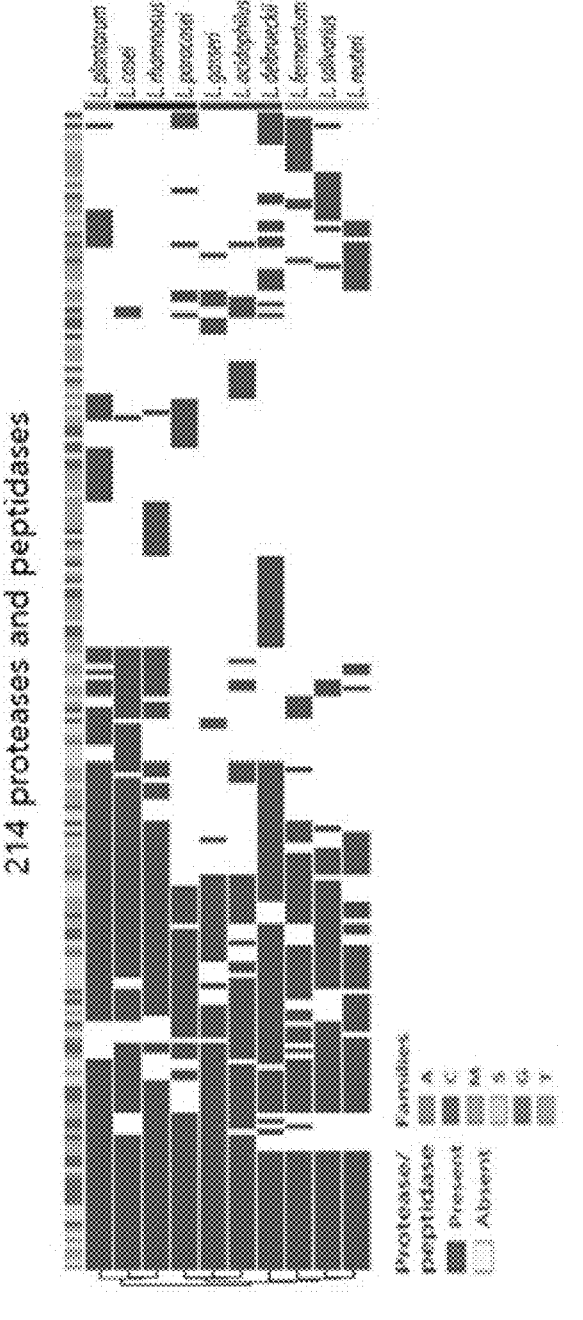
FIG. 2 is a diagram showing the hierarchical cluster analysis of proteolytic enzymes for 10 species of *Lactobacilloceae;*

Example 2: Proteolytic Enzyme Profile Analysis of *Lactobacilluseae* Strain for BP Production Proteolytic enzyme profiles of each *Lactobacilluseae* species were collected and clustered using the MEROPS database, and R package (FIG. 2). Clustering of proteases/peptidases was performed based on the presence or absence of proteolytic enzymes. The specific protease and peptidase profiles of the *Lactobacilluseae* species indicate that different *Lactobacilluseae* species can produce a variety of collagen BPs. Without testing all 10 *Lactobacilluseae* species, 4 representative strains were selected for generating bioactive peptide profiles based on substrate utilization patterns described below.

Example 3: Fractionation and Purification of Bioactive Collagen Peptide

To analyze the composition of collagen hydrolysates from a culture fluid of *L. paracasei*, *L. plantarum*, and *L. salivarius*, culture supernatants were concentrated, fractionated into HMW (>10 kDa) and LMW (<10 kDa) collagen protein/peptide fractions through step-by-step ultrafiltration, and lyophilized. Each fraction was loaded directly onto a Superdex 30 preparative grade column for size-exclusion chromatography. Chromatographic peaks were monitored by analyzing peptides at 210 nm (FIG. 4). *L. paracasei*, *L. plantarum*, and *L. salivarius* culture supernatants showed greater peak area within 1-10 kDa range in the LMW (<10 kDa) peptide fraction compared to crude (pre-ultrafiltration) samples. Through this, ultrafiltration confirmed a fraction according to the molecular weight of the collagen hydrolysate.

Example 4: LC-MS/MS Analysis of Collagen Peptide (CP) Profile from *Lactobacillusceae* Species Peptide sequences were analyzed using LC-MS/MS to investigate whether different patterns of collagen hydrolysis and matrix utilization result in distinct peptide profiles. While most of the peptides were derived from collagen, *L. plantarum* and *L. salivarius* collagen hydrolysates included trace amounts of microbial peptides (FIG. 5A). The three collagen hydrolysates showed distinct peptide sequences. 85% or more of the peptides were species-specific, indicating that various collagen peptides can be produced from the anaerobic digestion of collagen in a probiotics-dependent manner (FIG. 5B). Interestingly, the collagen hydrolysates of *L. plantarum* and *L. salivarius* shared more peptides compared to *L. paracasei*. In addition, while the three hydrolysates included peptides with similar p/s, their molecular weights were distributed differently (FIG. 5C). An average molecular weight of hydrolysates produced by *L. plantarum* was lower than that of collagen hydrolysates produced by *L. paracasei*. In contrast, the peptides of the collagen hydrolysates of *L. salivarius* were spread over a wide range of molecular weights. These distinct patterns in peptide sequences and their physicochemical properties revealed the diversity of peptide profiles generated during anaerobic digestion by these three species.

The portfolio of peptides produced by *Lactobacilluseae* species represents an expansion of the diversity of proteolytic systems and the availability of peptides. Mapping of collagen peptides to a representative collagen protein, "collagen alpha-2 (I) chain isoform X2" (accession number XP_026771581), revealed that peptide distributions of each hydrolysate were complementary to each other in cleaving collagen proteins (FIG. 5D). In addition, cleavage patterns of bacterial proteases were inferred by analyzing residues in the C-terminal and N-terminal directions. 70% or more of peptides produced by *L. paracasei* presented glycine (G) at the P1' and P3 sites (FIG. 5E). In contrast, aspartate (D) and glycine (G), as well as glycine (G) and proline (P) were found at the P1 and P1' sites for *L. plantarum* and *L. salivarius*, respectively. Overall, *L. paracasei* and *L. plantarum* (or *L. salivarius*) produced distinct peptide profiles, probably due to different protease/peptidase repertoires. On the other hand, *L. plantarum* and *L. salivarius* had more in common with regard to cleavage patterns.

TABLE 2

| | *L. plantarum* | | |
|---|---|---|---|
| Number | Amino acid sequence (NH$_2$--COOH) | Length | Molecular weight (kDa) |
| 1 | GA(Hyp)GRPGEVGAAGPPG(Hyp)(Hyp)GERGSTGSD | 27 | 2.45 |
| 2 | SGG(Hyp)GEAGREGS(Hyp)GHDGA(Hyp)GRD | 22 | 2.08 |
| 3 | GPPGAAGEKGEPGPVG(Hyp)AGSTGPRGG | 26 | 2.24 |
| 4 | GPPGAAGEKGEPGPVG(Hyp)AG | 19 | 1.63 |
| 5 | G(Hyp)AG(Hyp)QGATGESGRPGE(Hyp)GLPGSRGVSG | 28 | 2.55 |
| 6 | GKAGPAG(Hyp)AGQDGAAGPPGPAGSRGLPGVM | 30 | 2.58 |
| 7 | GETG(Hyp)AGGRGSEGPQGARGEPGN | 23 | 2.12 |
| 8 | AGPQGATGESGR(Hyp)GE | 15 | 1.40 |
| 9 | GA(Hyp)GR(Hyp)GEVGAAGPPG(Hyp)(Hyp)GERGSTGSD | 27 | 2.46 |
| 10 | SGPKGDAG(Hyp)(Hyp)GPPGPVG | 17 | 1.49 |
| 11 | AG(Hyp)PGPPG(Hyp)VGAGGPQ | 16 | 1.36 |
| 12 | AAG(Hyp)PGP(Hyp)GERGSTGSD | 17 | 1.55 |
| 13 | IGL(Hyp)GMTGPQGEAGREGSPGND | 22 | 2.12 |
| 14 | GEIGPAGPSGPAGPQGQR | 18 | 1.64 |
| 15 | PLG(Hyp)AGAAGRPGN | 13 | 1.16 |
| 16 | SGR(Hyp)GEAGLVGAR | 13 | 1.25 |
| 17 | GPQGPAGASGPRGLTGD | 17 | 1.51 |
| 18 | GEVGPQGGRGPEGPQ | 15 | 1.43 |
| 19 | GPQGEAGREGS(Hyp)GND | 15 | 1.46 |
| 20 | (Hyp)GPAGAVGAQGPIGPRGPSGPPGPD | 25 | 2.19 |
| 21 | PGPGPMGLMGPRGPSGPPG | 19 | 1.73 |
| 22 | IAGASGPLGPAGAAGR(Hyp)G | 18 | 1.50 |
| 23 | SGPAGPAGPSGPRGPAGPSG | 20 | 1.64 |

TABLE 2-continued

_L. plantarum_

| Number | Amino acid sequence (NH₂--COOH) | Length | Molecular weight (kDa) |
|---|---|---|---|
| 24 | ATASLFAIGATAQA | 14 | 1.30 |
| 25 | GLSGPAGGKGERGN | 14 | 1.27 |
| 26 | IAGASGPLGPAGAAGR(Hyp)GN | 19 | 1.62 |
| 27 | (Hyp)GPAGAVGAQGPIGPR | 16 | 1.43 |
| 28 | RGE(Hyp)GAPG(Hyp)LGIAGASG (Hyp)LGPAGAAGRPGN | 30 | 2.64 |
| 29 | AVGLLLATGQAANA | 14 | 1.28 |
| 30 | GPAGASGPRGLTGD | 14 | 1.22 |
| 31 | PGPGPMGLMGPRG | 13 | 1.24 |
| 32 | TGPQGEAGREGS(Hyp)GND | 16 | 1.56 |
| 33 | GPDGKTGSAGP(Hyp)GQD | 15 | 1.37 |
| 34 | SGPLGPAGAAGR(Hyp)GN | 15 | 1.31 |
| 35 | PGPGPMGLMGPR | 12 | 1.18 |
| 36 | PGPGPMGLMGPRGP | 14 | 1.33 |
| 37 | ASG(Hyp)LGPAGAAGRPGN | 16 | 1.38 |
| 38 | PQGPAGASGPRGLTGD | 16 | 1.45 |
| 39 | (Hyp)GPAGAVGAQGPIGPRG(Hyp)SG PPGPD | 25 | 2.21 |
| 40 | PGPGPMGLMGPRGPSG | 16 | 1.48 |
| 41 | ATGF(Hyp)GAAGRLGPPG(Hyp)AGN | 19 | 1.71 |
| 42 | G(Hyp)GPQGPAGASGPRGLTGD | 19 | 1.68 |
| 43 | AGMLVTSQAVANA | 13 | 1.24 |
| 44 | GPQGKEGPAGPSGQD | 15 | 1.39 |
| 45 | PGPAGAVGAQGPIGPR | 16 | 1.41 |
| 46 | (Hyp)G(Hyp)(Hyp)GPPGASGKEGAK G | 17 | 1.52 |
| 47 | (Hyp)G(Hyp)(Hyp)GPPGASGKEG | 14 | 1.26 |
| 48 | GEIGPAG(Hyp)SGPAGPQGQRGEPGTN | 24 | 2.22 |
| 49 | GF(Hyp)GPRGG(Hyp)GPQGPAGASGP RGLTGD | 26 | 2.36 |
| 50 | IAG(Hyp)PGSTGPAGKD | 14 | 1.25 |
| 51 | GPIGPRG(Hyp)SGPPGPD | 15 | 1.39 |
| 52 | SAG(Hyp)(Hyp)GF(Hyp)GA(Hyp)G PK | 14 | 1.31 |
| 53 | GSAGPQGKEGPAGPSGQD | 18 | 1.61 |
| 54 | (Hyp)G(Hyp)(Hyp)GPPGASGKE | 13 | 1.21 |
| 55 | PSGEPGPAGASGPAGPRGPVG | 21 | 1.78 |
| 56 | ALAGMLVTSQAVANA | 15 | 1.43 |
| 57 | AIGA(Hyp)GAAGKD | 11 | 0.96 |

TABLE 2-continued

_L. plantarum_

| Number | Amino acid sequence (NH₂--COOH) | Length | Molecular weight (kDa) |
|---|---|---|---|
| 58 | GE(Hyp)GMPGSKGMTGSPGS(Hyp)GP D | 21 | 1.94 |
| 59 | VVGGAGEKGEAGPA | 14 | 1.21 |
| 60 | GEAGPSGAVGPAGPAGAR | 18 | 1.49 |
| 61 | PGPAGASGPAGPRGPVGVA | 19 | 1.58 |
| 62 | IGL(Hyp)GMTGPQGEAGREGSPGN | 21 | 2.01 |
| 63 | GIRGLTG(Hyp)IGPPGPAGPQ | 18 | 1.67 |
| 64 | VGPTGPAGPAG | 11 | 0.89 |
| 65 | PGPGPMGLMGPRGPS | 15 | 1.42 |
| 66 | PRGGPGPQGPAGASG(Hyp)RGLTGD | 22 | 1.99 |
| 67 | GVAGPVG(Hyp)PGN | 11 | 0.95 |
| 68 | (Hyp)GPQGPAGASGPRGLTGD | 18 | 1.62 |
| 69 | GL(Hyp)GSPGSAGPQGKEG(Hyp)AGP SGQD | 24 | 2.15 |
| 70 | GLIG(Hyp)PG(Hyp)SGERGAPG | 16 | 1.46 |
| 71 | STALLPMLSSKA | 12 | 1.23 |
| 72 | GG(Hyp)PGPTG(Hyp)RGQPGN | 15 | 1.39 |
| 73 | SGPLGPAGAAGR(Hyp)G | 14 | 1.19 |
| 74 | AGASGPLGPAGAAGR(Hyp)GN | 18 | 1.51 |
| 75 | SKGMTGS(Hyp)GSPGPD | 14 | 1.30 |
| 76 | GASGPLG(Hyp)AGAAGRPGN | 17 | 1.43 |
| 77 | VMGAIGA(Hyp)GAAGKD | 14 | 1.24 |
| 78 | YNGPYKMTGWTGTNLS | 16 | 1.80 |
| 79 | AVGAQGPIGPRGPSG(Hyp)PGPD | 20 | 1.81 |
| 80 | GA(Hyp)GPDGKAGPAGPAGDK | 18 | 1.55 |
| 81 | GPRGDVGPAGPQGEN | 15 | 1.42 |
| 82 | GIAGASG(Hyp)LGPAGAAGRPGN | 20 | 1.68 |
| 83 | PGPAGAVGAQGPIGPRG | 17 | 1.47 |
| 84 | AGA(Hyp)GPAGATGA | 12 | 0.93 |
| 85 | AGA(Hyp)GPAGATGAPGPQG(Hyp)VG | 20 | 1.63 |
| 86 | GGPGPQG(Hyp)AGASGPRGLTGD | 20 | 1.73 |
| 87 | GPIGPRG(Hyp)SGPPGPDGN | 17 | 1.56 |
| 88 | ELPTMDISKSTDVV | 14 | 1.55 |
| 89 | ATTGAIALGATAAKA | 15 | 1.30 |
| 90 | AVGAPGKDGDVGAPG(Hyp)SG(Hyp)A GPAGDKGEQG | 30 | 2.62 |

TABLE 2-continued

| | | | |
|---|---|---|---|
| | *L. plantarum* | | |
| Number | Amino acid sequence (NH2--COOH) | Length | Molecular weight (kDa) |
| 91 | AVGAPGKDGDVGAPG(Hyp)SG(Hyp)A GPAGD | 25 | 2.12 |

TABLE 2-continued

| | | | |
|---|---|---|---|
| | *L. plantarum* | | |
| Number | Amino acid sequence (NH2--COOH) | Length | Molecular weight (kDa) |
| 92 | GEVGPQGGRG(Hyp)EGPQGARGEPG | 22 | 2.07 |
| 93 | GEAGPSGAVG(Hyp)AGPAGARGAPGPA G(Hyp)RGEK | 30 | 2.60 |
| 94 | SGPAGPAGPSGPRGPAGPSGPAGKD | 25 | 2.11 |

TABLE 3

| | | | |
|---|---|---|---|
| | *L. paracasei* | | |
| Number | Amino acid sequence (NH2--COOH) | Length | Molecular weight (kDa) |
| 1 | AAG(Hyp)PGP(Hyp)GERGSTGSD | 17 | 1.55 |
| 2 | AGL(Hyp)GPAGPPGEPGPAG(Hyp)T | 19 | 1.64 |
| 3 | AGLPGPAGPPGEPGPAG(Hyp)TGPAGPRGPS | 28 | 2.40 |
| 4 | AGL(Hyp)GPAGPPGEPGPAG(Hyp)TG(Hyp)AGPRGPS | 28 | 2.43 |
| 5 | AGL(Hyp)GPAGPPGEPGPAG(Hyp)TGPAGPRGPS | 28 | 2.42 |
| 6 | DGARGDAGAAGV(Hyp)GGVGSAGPQ | 22 | 1.85 |
| 7 | GAAGPPG(Hyp)VGPGGKEGQ | 17 | 1.46 |
| 8 | GA(Hyp)GL(Hyp)G(Hyp)(Hyp)GPPGPAGIG | 18 | 1.54 |
| 9 | GA(Hyp)GL(Hyp)GPPGPPGPAGIGE(Hyp)F(Hyp) | 22 | 2.01 |
| 10 | GA(Hyp)GL(Hyp)GPPGPPGPAGIGE(Hyp)F(Hyp)IIPQ | 26 | 2.46 |
| 11 | GA(Hyp)GL(Hyp)GPPGPPGPAGIGE(Hyp)F(Hyp)IIPQP | 27 | 2.56 |
| 12 | GA(Hyp)GL(Hyp)G(Hyp)PGPPGPAGIGE(Hyp)F(Hyp)IIPQPE | 28 | 2.71 |
| 13 | GA(Hyp)GL(Hyp)GPPGPPGPAGIGE(Hyp)FPIIPQPE | 28 | 2.67 |
| 14 | GA(Hyp)GL(Hyp)GPPGPPGPAGIGE(Hyp)F(Hyp)IIPQPE | 28 | 2.69 |
| 15 | GA(Hyp)GL(Hyp)GPPGPPGPAGIGE(Hyp)F(Hyp)IIPQPEK | 29 | 2.82 |
| 16 | GA(Hyp)GL(Hyp)GPPGPPGPAGIGE(Hyp)F(Hyp)IIPQPEKA | 30 | 2.89 |
| 17 | GA(Hyp)GR(Hyp)GEVGAAGPPG(Hyp)(Hyp)GERGST | 24 | 2.20 |
| 18 | GA(Hyp)GR(Hyp)GEVGAAGPPG(Hyp)(Hyp)GERGSTGSD | 27 | 2.46 |
| 19 | GARGDAGAAGV(Hyp)GGVGSAGPQ | 21 | 1.74 |
| 20 | GARGEPGNPGPGGAAG(Hyp)(Hyp)G(Hyp)PGSD | 24 | 2.09 |
| 21 | GARGS(Hyp)GAAGNDGARGDAGAA | 21 | 1.78 |
| 22 | GETGPAGGRGSEGPQ | 15 | 1.37 |
| 23 | GETG(Hyp)AGGRGSEGPQGARGEPGN | 23 | 2.12 |
| 24 | GF(Hyp)GAAGRVGPPGPAGAAG(Hyp)(Hyp)GPVGPG | 27 | 2.28 |
| 25 | GF(Hyp)GAAGRVGPPGPAGAAG(Hyp)(Hyp)GPVGPGGKE | 30 | 2.60 |
| 26 | GFTGPAGEPGEPGPSG(Hyp)MG(Hyp)RGPIGPPGRN | 30 | 2.84 |
| 27 | GKAGPAG(Hyp)AGQDGAAGPPGPA | 21 | 1.73 |
| 28 | GKAGPAG(Hyp)AGQDGAAGPPGPAGSRGLPGVM | 30 | 2.58 |

TABLE 3-continued

| | | | Molecular weight |
|---|---|---|---|
| Number | Amino acid sequence (NH$_2$--COOH) | Length | (kDa) |
| 29 | GL (Hyp) GPAGPPGEPGPAG (Hyp) TGPAGPRGPS | 27 | 2.35 |
| 30 | GMAGLPGPAGPPGEPG (Hyp) AGPTGPAGPRGPS | 30 | 2.59 |
| 31 | GNDGARGDAGAAGV (Hyp) GGVGSAGPQ | 24 | 2.02 |
| 32 | G (Hyp) AGQDGAAGPPGPA | 15 | 1.25 |
| 33 | G (Hyp) AGQDGAAGPPGPAGSR | 18 | 1.55 |
| 34 | G (Hyp) AGQDGAAGPPGPAGSRGLPGVM | 24 | 2.10 |
| 35 | GSPGAPG (Hyp) DGKAGPAG (Hyp) AGQD | 21 | 1.80 |
| 36 | NDGARGDAGAAGV (Hyp) GGVGSAGPQ | 23 | 1.97 |
| 37 | (Hyp) G (Hyp) PGPPGPAGIGEPF (Hyp) | 17 | 1.60 |
| 38 | SGMAGLPGPAGPPGE (Hyp) GPAGPT | 22 | 1.90 |
| 39 | SGPKGPDGAPGKDGLR | 16 | 1.52 |
| 40 | SGPKGPDGAPGKDGLRG | 17 | 1.58 |
| 41 | GFTGPAGE (Hyp) GEPGPSGPMGPR | 21 | 1.98 |
| 42 | GA (Hyp) GPPGAAGEKGEPG (Hyp) VGPA | 21 | 1.81 |
| 43 | AGP (Hyp) GADGQ (Hyp) GAKGEAGD | 18 | 1.60 |
| 44 | AG (Hyp) (Hyp) GQDGR (Hyp) GPPGPVGA | 18 | 1.64 |
| 45 | ALAVPGPMGPMGPRGPPGPPGLSGPQ | 26 | 2.40 |
| 46 | AVPGPMGPMGPRGPPGPPGLSGPQ | 24 | 2.22 |
| 47 | DGAAGAAG (Hyp) PGPTGPAG (Hyp) (Hyp) GF (Hyp) GGPGAK | 28 | 2.36 |
| 48 | GAAGPAGPRGPAGPA | 15 | 1.22 |
| 49 | GAAG (Hyp) PGKNGEDGESGK (Hyp) GR (Hyp) GERGPPGPQ | 30 | 2.87 |
| 50 | GAIGA (Hyp) GAAGKDGD | 14 | 1.18 |
| 51 | GA (Hyp) GFQGL (Hyp) GPAGPVGET | 18 | 1.65 |
| 52 | GA (Hyp) GFQGL (Hyp) G (Hyp) AGPVGETGKPGDRGI (Hyp) GD | 29 | 2.73 |
| 53 | GAPGLRG (Hyp) (Hyp) GPDGNNGPAGPVGVVGGAGEK | 30 | 2.65 |
| 54 | GAPGLRG (Hyp) PGPDGNNGPAGPVGVVGGAGEK | 30 | 2.64 |
| 55 | GASGPAGPRGPVGVA | 15 | 1.26 |
| 56 | GAVGPAG (Hyp) AGARGAPGPAGPR | 21 | 1.77 |
| 57 | GEIG (Hyp) AGPPGPPGPPG (Hyp) (Hyp) G (Hyp) SGGGFDIGF | 29 | 2.62 |
| 58 | GFAG (Hyp) PGADGQ (Hyp) GAKGEAGD | 20 | 1.80 |
| 59 | GF (Hyp) GAAGRVGPPGPAGIAG (Hyp) (Hyp) GSTGPAGKD | 30 | 2.63 |
| 60 | GFTGPPGE (Hyp) GEAGASGPMGPRGA | 23 | 2.08 |
| 61 | GGAALAVPGPMGPMGPRGPPGPPGLSGPQ | 29 | 2.59 |
| 62 | GIAG (Hyp) PGSTGPAGKD | 15 | 1.31 |
| 63 | GIRGLTG (Hyp) IGPPGPAGPQ | 18 | 1.67 |
| 64 | GIRGLTG (Hyp) IGPPGPAGPQGDKGEPGA | 26 | 2.38 |
| 65 | GIRGLTGPIGPPGPAG (Hyp) QGDKGEPGAAGPL | 30 | 2.72 |

TABLE 3-continued

*L. paracasei*

| Number | Amino acid sequence (NH₂--COOH) | Length | Molecular weight (kDa) |
|---|---|---|---|
| 66 | GISGPSGLIG(Hyp)PGITGL(Hyp)GAR | 21 | 1.92 |
| 67 | GISGPSGLIG(Hyp)PGITGL(Hyp)GARGE | 23 | 2.10 |
| 68 | GKEGPAG(Hyp)SGQDGRGGPPGPTGPR | 24 | 2.21 |
| 69 | GKEGPAGPSGQDGRGG(Hyp)(Hyp)GPTGPRGQPGN | 29 | 2.68 |
| 70 | GKTGSAG(Hyp)(Hyp)GQDGRPG(Hyp)PGPVGA | 23 | 2.07 |
| 71 | GLIG(Hyp)PGITGL(Hyp)GARGE | 17 | 1.61 |
| 72 | GLMGPRGPSGPPGAPGPQGLQ | 21 | 1.94 |
| 73 | GLMGPRG(Hyp)SGPPGAPGPQGLQ | 21 | 1.96 |
| 74 | GLTGAAGDEGKR | 12 | 1.14 |
| 75 | GLTGAAGDEGKRGQT | 15 | 1.43 |
| 76 | GLTGAAGDEGKRGQTGEQ | 18 | 1.74 |
| 77 | GLTGF(Hyp)GAAGRVGPPG(Hyp)A | 18 | 1.62 |
| 78 | GLTGF(Hyp)GAAGRVGPPG(Hyp)AGIAG(Hyp)PGSTGPA | 30 | 2.60 |
| 79 | GLTG(Hyp)IGPPGPAGPQGDKGEPGAAGPL | 27 | 2.39 |
| 80 | GLTG(Hyp)IGPPGPAGPQGDKGEPGAAGPLGPT | 30 | 2.65 |
| 81 | GMPGPSGPSGDSGPAGPAGPSGPRGPA | 27 | 2.28 |
| 82 | GMPGPSGPSGDSGPAGPAGPSGPRGPAGPS | 30 | 2.53 |
| 83 | GNTG(Hyp)AGPAGPLGSAG(Hyp)(Hyp)GFPGAPGPK | 27 | 2.34 |
| 84 | GPAGARGA(Hyp)GPAGPR | 15 | 1.32 |
| 85 | G(Hyp)(Hyp)G(Hyp)(Hyp)GPPGPPGPSGGGFDIGF | 23 | 2.09 |
| 86 | GPSGQDGRGGPPGPTG(Hyp)RGQPGN | 23 | 2.13 |
| 87 | GSAG(Hyp)PGQDGR(Hyp)GPPG(Hyp)VGA | 20 | 1.79 |
| 88 | GSPGAPG(Hyp)DGKAGPAG(Hyp)AGDK | 21 | 1.80 |
| 89 | GSPGS(Hyp)G(Hyp)DGKTGS | 14 | 1.24 |
| 90 | GSPGSPG(Hyp)DGKTGSAG(Hyp)(Hyp)GQD | 21 | 1.88 |
| 91 | LTG(Hyp)IGPPGPAGPQGDKGEPGAAGPLGPT | 29 | 2.59 |
| 92 | (Hyp)G(Hyp)(Hyp)GPPGASGKE | 13 | 1.21 |
| 93 | SAG(Hyp)(Hyp)GFPGAPGPKGEIG(Hyp)AGPSGPAGPQ | 29 | 2.57 |
| 94 | SGPAGPAGPSGPRGPAGPS | 19 | 1.59 |
| 95 | TG(Hyp)AGPAGPLGSAGP(Hyp)GF(Hyp)GAPGPK | 25 | 2.17 |
| 96 | VVGGAGEKGEAGPA | 14 | 1.21 |
| 97 | SGPAGPAGPSGPRGPAGPSGPA | 22 | 1.81 |
| 98 | GMPGPSGPSGDSGPAGPAGPSGPR | 24 | 2.06 |
| 99 | GFTGPPGE(Hyp)GEAGASGPMGPR | 21 | 1.95 |
| 100 | SGPAGPAGAAGPAGPRGPAGPA | 22 | 1.75 |
| 101 | AGAAGV(Hyp)GGVGSAGPQ | 16 | 1.28 |
| 102 | AVGA(Hyp)GKDGDVGAPG(Hyp)S | 17 | 1.50 |

TABLE 3-continued

| | L. paracasei | | |
|---|---|---|---|
| Number | Amino acid sequence (NH₂--COOH) | Length | Molecular weight (kDa) |
| 103 | GA(Hyp)GLPGPPGPPGPAGIGE(Hyp)FPIIPQPE | 28 | 2.66 |
| 104 | G(Hyp)AG(Hyp)QGATGESGRPGE(Hyp)GLPGSRGVS | 27 | 2.49 |
| 105 | GAIGA(Hyp)GAAGKDGDVGA(Hyp)GAPGPAG(Hyp)AGER | 30 | 2.56 |
| 106 | PGPMGPMGPRGPPGPPGLSGPQ | 22 | 2.05 |

TABLE 4

| | L. salivarius | | |
|---|---|---|---|
| Number | Amino acid sequence (NH₂--COOH) | Length | Molecular weight (kDa) |
| 1 | AAG(Hyp)PGP(Hyp)GERGSTGSD | 17 | 1.55 |
| 2 | AVGAPGKDGDVGA(Hyp)G(Hyp)SGPAGPAG | 24 | 2.00 |
| 3 | AVGAPGKDGDVGA(Hyp)G(Hyp)SGPAGPAGD | 25 | 2.12 |
| 4 | ETG(Hyp)AGGRGSEGPQGARGEPGN | 22 | 2.07 |
| 5 | GAAG(Hyp)PG(Hyp)AGSRGLPGVMGFPGPKGAD | 27 | 2.42 |
| 6 | GAAGPPG(Hyp)AGSRGLPGVM | 18 | 1.58 |
| 7 | GAAGPPG(Hyp)(Hyp)GERGSTGSD | 18 | 1.61 |
| 8 | GA(Hyp)GL(Hyp)GPPGPPGPAGIGE(Hyp)F(Hyp)IIPQPE | 28 | 2.69 |
| 9 | GA(Hyp)GR(Hyp)GEVGAAGPPG(Hyp)(Hyp)GERGSTG | 25 | 2.26 |
| 10 | GA(Hyp)GR(Hyp)GEVGAAGPPG(Hyp)(Hyp)GERGSTGSD | 27 | 2.46 |
| 11 | GA(Hyp)GRPGEVGAAGPPG(Hyp)(Hyp)GERGSTGSD | 27 | 2.45 |
| 12 | GDTG(Hyp)AG(Hyp)KGE(Hyp)GSPGEN | 18 | 1.68 |
| 13 | GDTGPAG(Hyp)KGE(Hyp)GSPGEN | 18 | 1.67 |
| 14 | GETG(Hyp)AGGRGSEGPQGARGEPGN | 23 | 2.12 |
| 15 | GETGPAGGRGSEGPQ | 15 | 1.37 |
| 16 | G(Hyp)AGGRGSEGPQGARGEPGN | 20 | 1.84 |
| 17 | G(Hyp)AG(Hyp)QGATGESGRPGE(Hyp)GLPGSRGVSG | 28 | 2.55 |
| 18 | G(Hyp)(Hyp)GPPGERGSTGSD | 15 | 1.41 |
| 19 | GPAG(Hyp)QGATGESGRPG | 16 | 1.42 |
| 20 | GPAGPQGATGESGR | 14 | 1.25 |
| 21 | GQDGAAG(Hyp)PGPAGSRGLPGVMGF(Hyp)GPKGAD | 30 | 2.72 |
| 22 | GR(Hyp)GEVGAAG(Hyp)(Hyp)GPPGERGSTGSD | 24 | 2.22 |
| 23 | GS(Hyp)GAKGS(Hyp)GPAGIT | 15 | 1.30 |
| 24 | (Hyp)AGGRGSEGPQGARGEPGN | 19 | 1.78 |
| 25 | (Hyp)GPGGAAG(Hyp)PGPPGSD | 16 | 1.33 |
| 26 | PAG(Hyp)TGARGSPGAAGND | 17 | 1.48 |
| 27 | SGPKGPDGAPGKDGLRG | 17 | 1.58 |

TABLE 4-continued

| | *L. salivarius* | | |
|---|---|---|---|
| Number | Amino acid sequence (NH$_2$--COOH) | Length | Molecular weight (kDa) |
| 28 | TKGETGPAGGRGSEG(Hyp)QGARGEPGN | 25 | 2.35 |
| 29 | AAGLLAVGTIAANA | 14 | 1.22 |
| 30 | AGAPGPAGATGAPGPQG(Hyp)VGVTG(Hyp)KGARG | 29 | 2.45 |
| 31 | AGPSGAVG(Hyp)AGPAGARGAPGPA | 22 | 1.77 |
| 32 | AQGPIGPRGPSGPPG(Hyp)D | 17 | 1.58 |
| 33 | ARGLPGS(Hyp)GSAGPQGKEG(Hyp)AGPSGQD | 26 | 2.38 |
| 34 | ASG(Hyp)LGPAGAAGRPG | 15 | 1.26 |
| 35 | ASG(Hyp)LGPAGAAGRPGN | 16 | 1.38 |
| 36 | ETGPAGRTGEIGAA | 14 | 1.30 |
| 37 | GAIGA(Hyp)GAAGKDGD | 14 | 1.18 |
| 38 | GA(Hyp)GERGG(Hyp)GVAGPKGATGE(Hyp)GRN | 24 | 2.21 |
| 39 | GA(Hyp)GPDGKAGPAGPAGDK | 18 | 1.55 |
| 40 | GASGPLG(Hyp)AGAAGRPGN | 17 | 1.43 |
| 41 | GEDGESGK(Hyp)GRPGERG(Hyp)(Hyp)GPQ | 21 | 2.12 |
| 42 | GE(Hyp)GMPGSKGMTGSPGS(Hyp)GPD | 21 | 1.94 |
| 43 | GEPGAPG(Hyp)LGIAGASG(Hyp)LGPA | 21 | 1.79 |
| 44 | GEPGAPG(Hyp)LGIAGASG(Hyp)LGPAGAA | 24 | 1.99 |
| 45 | GEPGAPG(Hyp)LGIAGASG(Hyp)LGPAGAAGRPGN | 29 | 2.47 |
| 46 | GEPGAPG(Hyp)LGIAGASGPLGPA | 21 | 1.77 |
| 47 | GEPGAPG(Hyp)LGIAGASGPLGPAGAA | 24 | 1.97 |
| 48 | GEPGAPG(Hyp)LGIAGASGPLGPAGAAGRPGN | 29 | 2.45 |
| 49 | GEPGAPG(Hyp)LGIAGASGPLGPAG | 22 | 1.83 |
| 50 | GEPGAPGPLGIAGASGPLGPA | 21 | 1.75 |
| 51 | GEVGPQGGRG(Hyp)EGPQGARGEPG | 22 | 2.07 |
| 52 | GF(Hyp)GPRGG(Hyp)GPQGPAGASGPRGLTGD | 26 | 2.36 |
| 53 | GG(Hyp)PGPTG(Hyp)RGQPGN | 15 | 1.39 |
| 54 | GGPGPQG(Hyp)AGASGPRGLTGD | 20 | 1.73 |
| 55 | GIRGPAG(Hyp)PG | 10 | 0.91 |
| 56 | GK(Hyp)GRPGERG(Hyp)(Hyp)GPQGAR | 18 | 1.83 |
| 57 | GL(Hyp)GSPGSAGPQGKEG(Hyp)AGPSGQD | 24 | 2.15 |
| 58 | GNAGRDGARGAPGPSG(Hyp)(Hyp)GPAGANGD | 26 | 2.27 |
| 59 | G(Hyp)(Hyp)GPPGPSGEPGPAGASG(Hyp)AGPRGPVG | 28 | 2.39 |
| 60 | G(Hyp)(Hyp)GPPGPSGEPGPAGASG(Hyp)AGPRGPVGVA | 30 | 2.56 |
| 61 | G(Hyp)(Hyp)GPPGPSGEPGPAGASGPAGPRGPVG | 28 | 2.38 |
| 62 | G(Hyp)(Hyp)GPPGPSGEPGPAGASGPAGPRGPVGVA | 30 | 2.55 |
| 63 | G(Hyp)PGPPGPSGEPGPAGASGPAGPRGPVG | 28 | 2.36 |
| 64 | GPAGPRGPAGPAGARGD | 17 | 1.47 |

TABLE 4-continued

| | | | Molecular weight (kDa) |
|---|---|---|---|
| Number | Amino acid sequence (NH₂--COOH) | Length | |

*L. salivarius*

| Number | Amino acid sequence (NH$_2$--COOH) | Length | Molecular weight (kDa) |
|---|---|---|---|
| 65 | GPIGPRG(Hyp)SGPPGPD | 15 | 1.39 |
| 66 | GPRGPSG(Hyp)PGAPGPQ | 15 | 1.36 |
| 67 | GQ(Hyp)GAKGEAGDTGAKGDAGA(Hyp)GPAGAT | 27 | 2.31 |
| 68 | GR(Hyp)GPPG(Hyp)VGAR | 12 | 1.16 |
| 69 | GRPGPPG(Hyp)VGAR | 12 | 1.15 |
| 70 | GRPGQ(Hyp)GDRGASG(Hyp)QGARG | 19 | 1.82 |
| 71 | GSAGPKGA(Hyp)GERGGPGVAG(Hyp)K | 21 | 1.85 |
| 72 | GSAGPKGA(Hyp)GERGGPGVAG(Hyp)KGATGE(Hyp)GRN | 30 | 2.70 |
| 73 | GSAGPQGKEGPAGPSGQD | 18 | 1.61 |
| 74 | GS(Hyp)G(Hyp)DGKTGSAGPPGQD | 18 | 1.63 |
| 75 | GT(Hyp)GF(Hyp)GPRGGPGPQG(Hyp)AGASGPRG | 25 | 2.25 |
| 76 | GT(Hyp)GF(Hyp)GPRGGPGPQG(Hyp)AGASGPRGLTGD | 29 | 2.63 |
| 77 | IGL(Hyp)GMTGPQGEAGREGSPGND | 22 | 2.12 |
| 78 | INKDEGYYMEEYKDSNNIH | 19 | 2.37 |
| 79 | (Hyp)AGPAGARGAPGPAG(Hyp)RGEK | 20 | 1.81 |
| 80 | (Hyp)G(Hyp)(Hyp)GPPGASGKE | 13 | 1.21 |
| 81 | (Hyp)G(Hyp)(Hyp)GPPGASGKEGAKG | 17 | 1.52 |
| 82 | (Hyp)G(Hyp)(Hyp)GPPGASGKEG | 14 | 1.26 |
| 83 | (Hyp)G(Hyp)PGPPGASGKE | 13 | 1.19 |
| 84 | (Hyp)G(Hyp)PGPPGASGKEGAKG | 17 | 1.50 |
| 85 | (Hyp)G(Hyp)PGPPGASGKEG | 14 | 1.25 |
| 86 | (Hyp)GPAGAVGAQGPIGPRG(Hyp)SGPPGPD | 25 | 2.21 |
| 87 | (Hyp)GPAGAVGAQGPIGPRGPSGPPGPD | 25 | 2.19 |
| 88 | (Hyp)GPVGVKGDSGVK | 13 | 1.22 |
| 89 | (Hyp)GPVGVKGDSGVKGE(Hyp)G | 17 | 1.58 |
| 90 | (Hyp)GSRGIAGIPGLPGPTGHMGPQGI(Hyp) | 25 | 2.37 |
| 91 | PAGPRGPVGVAGSAGKD | 17 | 1.50 |
| 92 | PGPGPMGLMGPR | 12 | 1.18 |
| 93 | PGPGPMGLMGPRGPSGPPG | 19 | 1.73 |
| 94 | PGPVGVKGD | 9 | 0.84 |
| 95 | PGPVGVKGDSGVKGE | 15 | 1.39 |
| 96 | PLG(Hyp)AGAAGRPGN | 13 | 1.16 |
| 97 | PQGKEGPAGPSGQD | 14 | 1.34 |
| 98 | PRGGPGPQGPAGASG(Hyp)RGLTGD | 22 | 1.99 |
| 99 | PRGPAGPSGPAGKD | 14 | 1.28 |
| 100 | PSGDSGPAGPAGPSGPRGPAGPSGPAGKD | 29 | 2.47 |
| 101 | RGE(Hyp)GAPG(Hyp)LGIAGASG(Hyp)LGPAGAAGRPGN | 30 | 2.64 |

TABLE 4-continued

L. salivarius

| Number | Amino acid sequence (NH$_2$--COOH) | Length | Molecular weight (kDa) |
|---|---|---|---|
| 102 | SAGPQGKEGPAGPSGQD | 17 | 1.55 |
| 103 | SGPAGPAGAAGPAGPRGPAGPAGARGD | 27 | 2.21 |
| 104 | SGPAGPAGPSGPRGPAGPSGPAGKD | 25 | 2.11 |
| 105 | SGPLGPAGAAGR(Hyp)G | 14 | 1.19 |
| 106 | SGPLGPAGAAGR(Hyp)GN | 15 | 1.31 |
| 107 | SGR(Hyp)GEAGLVGAR | 13 | 1.25 |
| 108 | SGSAGPAGPAGARG | 14 | 1.12 |
| 109 | SGSAGPAGPAGARGS(Hyp)GERG | 20 | 1.72 |
| 110 | TGPQGEAGREGS(Hyp)GND | 16 | 1.56 |
| 111 | T(Hyp)GF(Hyp)GPRGGPGPQG(Hyp)AGASGPRGLTGD | 28 | 2.58 |
| 112 | VGA(Hyp)GAPG(Hyp)AGPAGERGEQGPAG | 23 | 2.00 |

Example 5: Screening of Collagen Peptide Showing Agonistic Activity for GPCRs Since *L. salivarius* showed a very similar protein cleavage pattern to *L. plantarum, L. plantarum*, and *L. paracasei* were selected for functional screening using the β-arrestin recruitment assay for GPCRs. LMW (<10 kDa) collagen hydrolysates of two strains were purified to obtain 1-10 kDa peptide fractions (FIG. 6A). To determine optimal concentrations for cell-based functional screening, the cytotoxicity of the peptide fractions was tested in Caco-2 cells. A collagen peptide fraction at a concentration of up to 1 mg/mL maintained 80% viability in Caco-2 cells after treatment for up to 48 hours (FIG. 7).

The agonistic activities of peptide fractions for 168 GPCRs were investigated (FIG. 6B). Overall, collagen hydrolysates produced by *L. plantarum* showed 20% or more agonistic activity for puringergic GPCRs (P2RY1, P2RY6, and P2RY12) and histamine receptors (HRH1 and HRH4) compared to control agonistic activity.

Collagen hydrolysates produced by *L. paracasei* highly activated FFAR1 and GPR35 receptors and activated the HRH receptors by 10% or more. Of all the GPCRs screened, 44 GPCRs showed moderate to high tissue expression or high RNA expression in the human intestines based on the Human Protein Atlas. In particular, five GPCRs (GPR35, HRH1, HRH2, P2RY1, and P2RY6) were significantly activated by 10% or more compared to control agonistic activity (FIG. 6C). Surprisingly, GPR35, a class A rhodopsin-like GPCR, was activated by the 1-10 kDa peptide fractions of both *L. paracasei* and *L. plantarum* and showed 25.5% and 8.6% activity compared to control agonist zaprinast, respectively. (FIG. 6D). GPR35 contributes to intestinal homeostasis against colitis, bacterial infections, and colon cancer. These results highlight the potential of collagen peptides produced by *L. paracasei* and *L. plantarum* to promote intestinal health by communicating with host cells via GPCRs.

Example 6: Wound Healing Analysis of Collagen Peptide Using Colonocytes

Based on their phenotypes in the intestinal epithelium, *L. plantarum* and *L. paracasei* collagen peptide fractions were investigated for their ability to act as GPCR agonists. To investigate wound healing capacity, wounded Caco-2 cells, and human colon epithelial cells were treated with each collagen peptide fraction. EGF, a well-known wound therapeutic agent, and zaprinast, an agonist of GPR35, were used as positive controls. *L. plantarum* and *L. paracasei* peptide fractions significantly promoted wound closure in Caco-2 cells at a level similar to that of zaprinast compared to a negative control group. In order to confirm GPR35-mediated wound healing activity, cells were pre-cultured with CID 2745687 and PD98059 to inhibit GPR35 and ERK1/2 signaling pathways, respectively. As a result, the wound-healing activities of *L. plantarum* and *L. paracasei* peptide fractions and zaprinast were abolished by GPR35 inhibition, but the effect of EGF was not inhibited (FIGS. 8A and 8B). Despite the relatively insignificant GPR35-binding activity (FIG. 6D), the collagen peptide fractions from both strains showed distinct wound healing activities (FIGS. 8A and 8B), indicating that this activity may be ascribed to other receptors and/or signaling pathways associated with intestinal epithelial cells. In addition, zaprinast, *L. plantarum*, and *L. paracasei* collagen peptide fractions increased ERK1/2 phosphorylation in Caco-2 cells by 3.76±0.2-fold, 2.39±0.4-fold, and 1.76±0.41-fold, respectively (FIG. 8C). These effects were reversed when treated with CID 2745687, which downregulates the ERK1/2 signaling pathway by inhibiting GPR35. Taken together, these results indicate that *L. plantarum* and *L. paracasei* collagen peptide fractions promote wound healing through the GPR35-mediated ERK1/2 signaling pathway in Caco-2 cells.

Example 7: Analysis of Inflammation-Relieving Effects of Collagen Peptides in Colon Epithelial Cell In order to evaluate the inflammation-relieving effects of collagen peptide fractions, the mRNA expression levels of pro-inflammatory cytokines (IL-6 and IL-8) responsible for the formation of prostanoids (COX-2) were measured in human colon epithelial cells, Caco-2. When LPS, which induces inflammation, was treated alone, the mRNA expression levels of IL-6, IL-8, and COX-2 were significantly increased. However, when collagen peptide fractions (10 or 20 μg/mL) produced by L. plantarum were co-treated with LPS, the mRNA expression levels of IL-6 and IL-8 were significantly decreased compared to the group treated only with LPS, and the mRNA expression level of COX-2 was also decreased but was not statistically significant. The collagen peptide fractions produced by L. paracasei also significantly decreased the mRNA expression level of IL-6. On the other hand, when treating the fraction in which a bacterial strain was not cultured (negative control), a decrease in IL-8 was confirmed in the 10 μg/mL treatment group, but the gene expression of IL-6 and COX-2 was not inhibited. This indicates that the collagen peptide fractions produced by L. plantarum and L. paracasei can relieve inflammation in intestinal epithelial cells (FIG. 9).

Effects of the Invention

Since collagen peptides obtained by culturing one or more microorganisms selected from L. paracasei, L. plantarum, and L. salivarius have GPR35 activity, the collagen peptides are suitable for use as food, pharmaceutical or cosmetic compositions and feed additives for improving intestinal functions, relieving inflammation and/or promoting wound healing because of the excellent wound healing and inflammation relieving effects of the peptides.

What is claimed is:

1. A food composition for improving intestinal function, relieving inflammation and/or promoting wound healing comprising, as an active ingredient, collagen peptides obtained by culturing one or more microorganisms selected from the group consisting of *Lacticaseibacillus paracasei*, *Lactiplantibacillus plantarum*, and *Ligilactobacillus salivarius*, wherein the collagen peptides are selected from the group consisting of collagen peptides having a molecular weight of less than 1 kDa and 1 to 10 kDa, wherein the collagen peptides have an isoelectric point in a range between 6 and 8 and an electric charge in a range between 0.0 and 0.3, and wherein each of the collagen peptides has GPR35 activity.

2. The food composition of claim 1, wherein the composition is prepared in a formulation selected from the group consisting of powders, granules, pills, tablets, capsules, candies, syrups, and beverages.

3. A cosmetic composition for relieving inflammation and/or promoting wound healing, comprising, as an active ingredient, collagen peptides obtained by culturing one or more microorganisms selected from the group consisting of *L. paracasei*, *L. plantarum*, and *L. salivarius*, wherein the collagen peptides are selected from the group consisting of collagen peptides having a molecular weight of less than 1 kDa and 1 to 10 kDa, wherein the collagen peptides have an isoelectric point in a range between 6 and 8 and an electric charge in a range between 0.0 and 0.3, and wherein each of the collagen peptides has GPR35 activity.

4. The cosmetic composition of claim 3, wherein the cosmetic composition is prepared in any one of formulations a formulation selected from the group consisting of solutions, suspensions, emulsions, pastes, gels, creams, lotions, powders, soaps, surfactant-containing cleansers, oils, powder foundations, emulsions, foundations, wax foundations, and sprays.

* * * * *

```
                         SEQUENCE LISTING

Sequence total quantity: 174
SEQ ID NO: 1            moltype = AA   length = 11
FEATURE                 Location/Qualifiers
source                  1..11
                        mol_type = protein
                        organism = unidentified
SITE                    1..11
                        note = P at position 5 is hydroxyproline.
SEQUENCE: 1
AIGAPGAAGK D                                                      11

SEQ ID NO: 2            moltype = AA   length = 11
FEATURE                 Location/Qualifiers
source                  1..11
                        mol_type = protein
                        organism = unidentified
SEQUENCE: 2
VGPTGPAGPA G                                                      11

SEQ ID NO: 3            moltype = AA   length = 11
FEATURE                 Location/Qualifiers
source                  1..11
                        mol_type = protein
                        organism = unidentified
SITE                    1..11
                        note = P at position 8 is hydroxyproline.
SEQUENCE: 3
GVAGPVGPPG N                                                      11

SEQ ID NO: 4            moltype = AA   length = 12
FEATURE                 Location/Qualifiers
source                  1..12
                        mol_type = protein
                        organism = unidentified
SEQUENCE: 4
GLTGAAGDEG KR                                                     12

SEQ ID NO: 5            moltype = AA   length = 12
FEATURE                 Location/Qualifiers
source                  1..12
                        mol_type = protein
                        organism = unidentified
SEQUENCE: 5
PGPGPMGLMG PR                                                     12

SEQ ID NO: 6            moltype = AA   length = 12
FEATURE                 Location/Qualifiers
source                  1..12
                        mol_type = protein
                        organism = unidentified
SITE                    1..12
                        note = P at position 4 is hydroxyproline.
SEQUENCE: 6
AGAPGPAGAT GA                                                     12

SEQ ID NO: 7            moltype = AA   length = 13
FEATURE                 Location/Qualifiers
```

-continued

```
source                   1..13
                         mol_type = protein
                         organism = unidentified
SITE                     1..13
                         note = P at position 1, 3 and 4 are hydroxyproline.
SEQUENCE: 7
PGPPGPPGAS GKE                                                    13

SEQ ID NO: 8             moltype = AA  length = 13
FEATURE                  Location/Qualifiers
source                   1..13
                         mol_type = protein
                         note = P at  is Hydroxyproline
                         organism = unidentified
SITE                     1..13
                         note = P at position 4 is hydroxyproline.
SEQUENCE: 8
PLGPAGAAGR PGN                                                    13

SEQ ID NO: 9             moltype = AA  length = 13
FEATURE                  Location/Qualifiers
source                   1..13
                         mol_type = protein
                         organism = unidentified
SITE                     1..13
                         note = P at position 4 is hydroxyproline.
SEQUENCE: 9
SGRPGEAGLV GAR                                                    13

SEQ ID NO: 10            moltype = AA  length = 13
FEATURE                  Location/Qualifiers
source                   1..13
                         mol_type = protein
                         organism = unidentified
SEQUENCE: 10
PGPGPMGLMG PRG                                                    13

SEQ ID NO: 11            moltype = AA  length = 14
FEATURE                  Location/Qualifiers
source                   1..14
                         mol_type = protein
                         organism = unidentified
SITE                     1..14
                         note = P at position 6 is hydroxyproline.
SEQUENCE: 11
GAIGAPGAAG KDGD                                                   14

SEQ ID NO: 12            moltype = AA  length = 14
FEATURE                  Location/Qualifiers
source                   1..14
                         mol_type = protein
                         organism = unidentified
SITE                     1..14
                         note = P at position 6 and 8 are hydroxyproline.
SEQUENCE: 12
GSPGSPGPDG KTGS                                                   14

SEQ ID NO: 13            moltype = AA  length = 14
FEATURE                  Location/Qualifiers
source                   1..14
                         mol_type = protein
                         organism = unidentified
SEQUENCE: 13
VVGGAGEKGE AGPA                                                   14

SEQ ID NO: 14            moltype = AA  length = 14
FEATURE                  Location/Qualifiers
source                   1..14
                         mol_type = protein
                         organism = unidentified
SEQUENCE: 14
GLSGPAGGKG ERGN                                                   14

SEQ ID NO: 15            moltype = AA  length = 14
FEATURE                  Location/Qualifiers
source                   1..14
                         mol_type = protein
                         organism = unidentified
SEQUENCE: 15
```

-continued

```
GPAGASGPRG LTGD                                                          14

SEQ ID NO: 16          moltype = AA  length = 14
FEATURE                Location/Qualifiers
source                 1..14
                       mol_type = protein
                       organism = unidentified
SEQUENCE: 16
PGPGPMGLMG PRGP                                                          14

SEQ ID NO: 17          moltype = AA  length = 14
FEATURE                Location/Qualifiers
source                 1..14
                       mol_type = protein
                       organism = unidentified
SITE                   1..14
                       note = P at position 1, 3 and 4 are hydroxyproline.
SEQUENCE: 17
PGPPGPPGAS GKEG                                                          14

SEQ ID NO: 18          moltype = AA  length = 14
FEATURE                Location/Qualifiers
source                 1..14
                       mol_type = protein
                       organism = unidentified
SITE                   1..14
                       note = P at position 4 is hydroxyproline.
SEQUENCE: 18
IAGPPGSTGP AGKD                                                          14

SEQ ID NO: 19          moltype = AA  length = 14
FEATURE                Location/Qualifiers
source                 1..14
                       mol_type = protein
                       organism = unidentified
SITE                   1..14
                       note = P at position 4, 5, 8 and 11 are hydroxyproline.
SEQUENCE: 19
SAGPPGFPGA PGPK                                                          14

SEQ ID NO: 20          moltype = AA  length = 14
FEATURE                Location/Qualifiers
source                 1..14
                       mol_type = protein
                       organism = unidentified
SITE                   1..14
                       note = P at position 13 is hydroxyproline.
SEQUENCE: 20
SGPLGPAGAA GRPG                                                          14

SEQ ID NO: 21          moltype = AA  length = 14
FEATURE                Location/Qualifiers
source                 1..14
                       mol_type = protein
                       organism = unidentified
SITE                   1..14
                       note = P at position 8 is hydroxyproline.
SEQUENCE: 21
SKGMTGSPGS PGPD                                                          14

SEQ ID NO: 22          moltype = AA  length = 14
FEATURE                Location/Qualifiers
source                 1..14
                       mol_type = protein
                       organism = unidentified
SITE                   1..14
                       note = P at position 8 is hydroxyproline.
SEQUENCE: 22
VMGAIGAPGA AGKD                                                          14

SEQ ID NO: 23          moltype = AA  length = 15
FEATURE                Location/Qualifiers
source                 1..15
                       mol_type = protein
                       organism = unidentified
SEQUENCE: 23
GETGPAGGRG SEGPQ                                                         15

SEQ ID NO: 24          moltype = AA  length = 15
```

-continued

```
FEATURE            Location/Qualifiers
source             1..15
                   mol_type = protein
                   organism = unidentified
SITE               1..15
                   note = P at position 2 is hydroxyproline.
SEQUENCE: 24
GPAGQDGAAG PPGPA                                          15

SEQ ID NO: 25      moltype = AA  length = 15
FEATURE            Location/Qualifiers
source             1..15
                   mol_type = protein
                   organism = unidentified
SEQUENCE: 25
GAAGPAGPRG PAGPA                                          15

SEQ ID NO: 26      moltype = AA  length = 15
FEATURE            Location/Qualifiers
source             1..15
                   mol_type = protein
                   organism = unidentified
SEQUENCE: 26
GASGPAGPRG PVGVA                                          15

SEQ ID NO: 27      moltype = AA  length = 15
FEATURE            Location/Qualifiers
source             1..15
                   mol_type = protein
                   organism = unidentified
SITE               1..15
                   note = P at position 5 is hydroxyproline.
SEQUENCE: 27
GIAGPPGSTG PAGKD                                          15

SEQ ID NO: 28      moltype = AA  length = 15
FEATURE            Location/Qualifiers
source             1..15
                   mol_type = protein
                   organism = unidentified
SEQUENCE: 28
GLTGAAGDEG KRGQT                                          15

SEQ ID NO: 29      moltype = AA  length = 15
FEATURE            Location/Qualifiers
source             1..15
                   mol_type = protein
                   organism = unidentified
SITE               1..15
                   note = P at position 9 is hydroxyproline.
SEQUENCE: 29
GPAGARGAPG PAGPR                                          15

SEQ ID NO: 30      moltype = AA  length = 15
FEATURE            Location/Qualifiers
source             1..15
                   mol_type = protein
                   organism = unidentified
SITE               1..15
                   note = P at position 13 is hydroxyproline.
SEQUENCE: 30
AGPQGATGES GRPGE                                          15

SEQ ID NO: 31      moltype = AA  length = 15
FEATURE            Location/Qualifiers
source             1..15
                   mol_type = protein
                   organism = unidentified
SEQUENCE: 31
GEVGPQGGRG PEGPQ                                          15

SEQ ID NO: 32      moltype = AA  length = 15
FEATURE            Location/Qualifiers
source             1..15
                   mol_type = protein
                   organism = unidentified
SITE               1..15
                   note = P at position 12 is hydroxyproline.
SEQUENCE: 32
```

-continued

```
GPQGEAGREG SPGND                                                 15

SEQ ID NO: 33           moltype = AA  length = 15
FEATURE                 Location/Qualifiers
source                  1..15
                        mol_type = protein
                        organism = unidentified
SITE                    1..15
                        note = P at position 12 is hydroxyproline.
SEQUENCE: 33
GPDGKTGSAG PPGQD                                                 15

SEQ ID NO: 34           moltype = AA  length = 15
FEATURE                 Location/Qualifiers
source                  1..15
                        mol_type = protein
                        organism = unidentified
SITE                    1..15
                        note = P at position 13 is hydroxyproline.
SEQUENCE: 34
SGPLGPAGAA GRPGN                                                 15

SEQ ID NO: 35           moltype = AA  length = 15
FEATURE                 Location/Qualifiers
source                  1..15
                        mol_type = protein
                        organism = unidentified
SEQUENCE: 35
GPQGKEGPAG PSGQD                                                 15

SEQ ID NO: 36           moltype = AA  length = 15
FEATURE                 Location/Qualifiers
source                  1..15
                        mol_type = protein
                        organism = unidentified
SITE                    1..15
                        note = P at position 8 is hydroxyproline.
SEQUENCE: 36
GPIGPRGPSG PPGPD                                                 15

SEQ ID NO: 37           moltype = AA  length = 15
FEATURE                 Location/Qualifiers
source                  1..15
                        mol_type = protein
                        organism = unidentified
SEQUENCE: 37
PGPGPMGLMG PRGPS                                                 15

SEQ ID NO: 38           moltype = AA  length = 15
FEATURE                 Location/Qualifiers
source                  1..15
                        mol_type = protein
                        organism = unidentified
SITE                    1..15
                        note = P at position 3 and 9 are hydroxyproline.
SEQUENCE: 38
GGPPGPTGPR GQPGN                                                 15

SEQ ID NO: 39           moltype = AA  length = 15
FEATURE                 Location/Qualifiers
source                  1..15
                        mol_type = protein
                        organism = unidentified
SEQUENCE: 39
GPRGDVGPAG PQGEN                                                 15

SEQ ID NO: 40           moltype = AA  length = 16
FEATURE                 Location/Qualifiers
source                  1..16
                        mol_type = protein
                        organism = unidentified
SEQUENCE: 40
SGPKGPDGAP GKDGLR                                                16

SEQ ID NO: 41           moltype = AA  length = 16
FEATURE                 Location/Qualifiers
source                  1..16
                        mol_type = protein
                        organism = unidentified
```

-continued

```
SITE                     1..16
                         note = P at position 3 and 9 are hydroxyproline.
SEQUENCE: 41
AGPPGPPGPV GAGGPQ                                                       16

SEQ ID NO: 42            moltype = AA  length = 16
FEATURE                  Location/Qualifiers
source                   1..16
                         mol_type = protein
                         organism = unidentified
SITE                     1..16
                         note = P at position 1 is hydroxyproline.
SEQUENCE: 42
PGPAGAVGAQ GPIGPR                                                       16

SEQ ID NO: 43            moltype = AA  length = 16
FEATURE                  Location/Qualifiers
source                   1..16
                         mol_type = protein
                         organism = unidentified
SITE                     1..16
                         note = P at position 13 is hydroxyproline.
SEQUENCE: 43
TGPQGEAGRE GSPGND                                                       16

SEQ ID NO: 44            moltype = AA  length = 16
FEATURE                  Location/Qualifiers
source                   1..16
                         mol_type = protein
                         organism = unidentified
SITE                     1..16
                         note = P at position 4 is hydroxyproline.
SEQUENCE: 44
ASGPLGPAGA AGRPGN                                                       16

SEQ ID NO: 45            moltype = AA  length = 16
FEATURE                  Location/Qualifiers
source                   1..16
                         mol_type = protein
                         organism = unidentified
SEQUENCE: 45
PQGPAGASGP RGLTGD                                                       16

SEQ ID NO: 46            moltype = AA  length = 16
FEATURE                  Location/Qualifiers
source                   1..16
                         mol_type = protein
                         organism = unidentified
SEQUENCE: 46
PGPGPMGLMG PRGPSG                                                       16

SEQ ID NO: 47            moltype = AA  length = 16
FEATURE                  Location/Qualifiers
source                   1..16
                         mol_type = protein
                         organism = unidentified
SEQUENCE: 47
PGPAGAVGAQ GPIGPR                                                       16

SEQ ID NO: 48            moltype = AA  length = 16
FEATURE                  Location/Qualifiers
source                   1..16
                         mol_type = protein
                         organism = unidentified
SITE                     1..16
                         note = P at position 5 and 8 are hydroxyproline.
SEQUENCE: 48
GLIGPPGPSG ERGAPG                                                       16

SEQ ID NO: 49            moltype = AA  length = 17
FEATURE                  Location/Qualifiers
source                   1..17
                         mol_type = protein
                         organism = unidentified
SITE                     1..17
                         note = P at position 4 and 8 are hydroxyproline.
SEQUENCE: 49
AAGPPGPPGE RGSTGSD                                                      17
```

```
SEQ ID NO: 50            moltype = AA  length = 17
FEATURE                  Location/Qualifiers
source                   1..17
                         mol_type = protein
                         organism = unidentified
SITE                     1..17
                         note = P at position 8 is hydroxyproline.
SEQUENCE: 50
GAAGPPGPVG PGGKEGQ                                                    17

SEQ ID NO: 51            moltype = AA  length = 17
FEATURE                  Location/Qualifiers
source                   1..17
                         mol_type = protein
                         organism = unidentified
SITE                     1..17
                         note = P at position 1, 3 and 17 are hydroxyproline.
SEQUENCE: 51
PGPPGPPGPA GIGEPFP                                                    17

SEQ ID NO: 52            moltype = AA  length = 17
FEATURE                  Location/Qualifiers
source                   1..17
                         mol_type = protein
                         organism = unidentified
SEQUENCE: 52
SGPKGPDGAP GKDGLRG                                                    17

SEQ ID NO: 53            moltype = AA  length = 17
FEATURE                  Location/Qualifiers
source                   1..17
                         mol_type = protein
                         organism = unidentified
SITE                     1..17
                         note = P at position 5 and 12 are hydroxyproline.
SEQUENCE: 53
GLIGPPGITG LPGARGE                                                    17

SEQ ID NO: 54            moltype = AA  length = 17
FEATURE                  Location/Qualifiers
source                   1..17
                         mol_type = protein
                         organism = unidentified
SITE                     1..17
                         note = P at position 9 and 10 are hydroxyproline.
SEQUENCE: 54
SGPKGDAGPP GPPGPVG                                                    17

SEQ ID NO: 55            moltype = AA  length = 17
FEATURE                  Location/Qualifiers
source                   1..17
                         mol_type = protein
                         organism = unidentified
SEQUENCE: 55
GPQGPAGASG PRGLTGD                                                    17

SEQ ID NO: 56            moltype = AA  length = 17
FEATURE                  Location/Qualifiers
source                   1..17
                         mol_type = protein
                         organism = unidentified
SITE                     1..17
                         note = P at position 1, 3 and 4 are hydroxyproline.
SEQUENCE: 56
PGPPGPPGAS GKEGAKG                                                    17

SEQ ID NO: 57            moltype = AA  length = 17
FEATURE                  Location/Qualifiers
source                   1..17
                         mol_type = protein
                         organism = unidentified
SITE                     1..17
                         note = P at position 8 is hydroxyproline.
SEQUENCE: 57
GASGPLGPAG AAGRPGN                                                    17

SEQ ID NO: 58            moltype = AA  length = 17
FEATURE                  Location/Qualifiers
source                   1..17
```

```
                            mol_type = protein
                            organism = unidentified
SEQUENCE: 58
PGPAGAVGAQ GPIGPRG                                               17

SEQ ID NO: 59              moltype = AA  length = 17
FEATURE                    Location/Qualifiers
source                     1..17
                           mol_type = protein
                           organism = unidentified
SITE                       1..17
                           note = P at position 8 is hydroxyproline.
SEQUENCE: 59
GPIGPRGPSG PPGPDGN                                               17

SEQ ID NO: 60              moltype = AA  length = 18
FEATURE                    Location/Qualifiers
source                     1..18
                           mol_type = protein
                           organism = unidentified
SITE                       1..18
                           note = P at position 3, 6, 8 and 9 are hydroxyproline.
SEQUENCE: 60
GAPGLPGPPG PPGPAGIG                                              18

SEQ ID NO: 61              moltype = AA  length = 18
FEATURE                    Location/Qualifiers
source                     1..18
                           mol_type = protein
                           organism = unidentified
SITE                       1..18
                           note = P at position 2 is hydroxyproline.
SEQUENCE: 61
GPAGQDGAAG PPGPAGSR                                              18

SEQ ID NO: 62              moltype = AA  length = 18
FEATURE                    Location/Qualifiers
source                     1..18
                           mol_type = protein
                           organism = unidentified
SITE                       1..18
                           note = P at position 4 and 10 are hydroxyproline.
SEQUENCE: 62
AGPPGADGQP GAKGEAGD                                              18

SEQ ID NO: 63              moltype = AA  length = 18
FEATURE                    Location/Qualifiers
source                     1..18
                           mol_type = protein
                           organism = unidentified
SITE                       1..18
                           note = P at position 3, 4 and 10 are hydroxyproline.
SEQUENCE: 63
AGPPGQDGRP GPPGPVGA                                              18

SEQ ID NO: 64              moltype = AA  length = 18
FEATURE                    Location/Qualifiers
source                     1..18
                           mol_type = protein
                           organism = unidentified
SITE                       1..18
                           note = P at position 3 and 9 are hydroxyproline.
SEQUENCE: 64
GAPGFQGLPG PAGPVGET                                              18

SEQ ID NO: 65              moltype = AA  length = 18
FEATURE                    Location/Qualifiers
source                     1..18
                           mol_type = protein
                           organism = unidentified
SITE                       1..18
                           note = P at position 8 is hydroxyproline.
SEQUENCE: 65
GIRGLTGPIG PPGPAGPQ                                              18

SEQ ID NO: 66              moltype = AA  length = 18
FEATURE                    Location/Qualifiers
source                     1..18
                           mol_type = protein
```

-continued

```
                            organism = unidentified
SEQUENCE: 66
GLTGAAGDEG KRGQTGEQ                                                    18

SEQ ID NO: 67        moltype = AA  length = 18
FEATURE              Location/Qualifiers
source               1..18
                     mol_type = protein
                     organism = unidentified
SITE                 1..18
                     note = P at position 6 and 17 are hydroxyproline.
SEQUENCE: 67
GLTGFPGAAG RVGPPGPA                                                    18

SEQ ID NO: 68        moltype = AA  length = 18
FEATURE              Location/Qualifiers
source               1..18
                     mol_type = protein
                     organism = unidentified
SEQUENCE: 68
GEIGPAGPSG PAGPQGQR                                                    18

SEQ ID NO: 69        moltype = AA  length = 18
FEATURE              Location/Qualifiers
source               1..18
                     mol_type = protein
                     organism = unidentified
SITE                 1..18
                     note = P at position 17 is hydroxyproline.
SEQUENCE: 69
IAGASGPLGP AGAAGRPG                                                    18

SEQ ID NO: 70        moltype = AA  length = 18
FEATURE              Location/Qualifiers
source               1..18
                     mol_type = protein
                     organism = unidentified
SEQUENCE: 70
GSAGPQGKEG PAGPSGQD                                                    18

SEQ ID NO: 71        moltype = AA  length = 18
FEATURE              Location/Qualifiers
source               1..18
                     mol_type = protein
                     organism = unidentified
SEQUENCE: 71
GEAGPSGAVG PAGPAGAR                                                    18

SEQ ID NO: 72        moltype = AA  length = 18
FEATURE              Location/Qualifiers
source               1..18
                     mol_type = protein
                     organism = unidentified
SITE                 1..18
                     note = P at position 1 is hydroxyproline.
SEQUENCE: 72
PGPQGPAGAS GPRGLTGD                                                    18

SEQ ID NO: 73        moltype = AA  length = 18
FEATURE              Location/Qualifiers
source               1..18
                     mol_type = protein
                     organism = unidentified
SITE                 1..18
                     note = P at position 16 is hydroxyproline.
SEQUENCE: 73
AGASGPLGPA GAAGRPGN                                                    18

SEQ ID NO: 74        moltype = AA  length = 18
FEATURE              Location/Qualifiers
source               1..18
                     mol_type = protein
                     organism = unidentified
SITE                 1..18
                     note = P at position 3 is hydroxyproline.
SEQUENCE: 74
GAPGPDGKAG PAGPAGDK                                                    18

SEQ ID NO: 75        moltype = AA  length = 19
```

```
FEATURE              Location/Qualifiers
source               1..19
                     mol_type = protein
                     organism = unidentified
SITE                 1..19
                     note = P at position 4 and 18 are hydroxyproline.
SEQUENCE: 75
AGLPGPAGPP GEPGPAGPT                                            19

SEQ ID NO: 76        moltype = AA  length = 19
FEATURE              Location/Qualifiers
source               1..19
                     mol_type = protein
                     organism = unidentified
SEQUENCE: 76
SGPAGPAGPS GPRGPAGPS                                            19

SEQ ID NO: 77        moltype = AA  length = 19
FEATURE              Location/Qualifiers
source               1..19
                     mol_type = protein
                     organism = unidentified
SITE                 1..19
                     note = P at position 17 is hydroxyproline.
SEQUENCE: 77
GPPGAAGEKG EPGPVGPAG                                            19

SEQ ID NO: 78        moltype = AA  length = 19
FEATURE              Location/Qualifiers
source               1..19
                     mol_type = protein
                     organism = unidentified
SEQUENCE: 78
PGPGPMGLMG PRGPSGPPG                                            19

SEQ ID NO: 79        moltype = AA  length = 19
FEATURE              Location/Qualifiers
source               1..19
                     mol_type = protein
                     organism = unidentified
SITE                 1..19
                     note = P at position 17 is hydroxyproline.
SEQUENCE: 79
IAGASGPLGP AGAAGRPGN                                            19

SEQ ID NO: 80        moltype = AA  length = 19
FEATURE              Location/Qualifiers
source               1..19
                     mol_type = protein
                     organism = unidentified
SITE                 1..19
                     note = P at position 5 and 16 are hydroxyproline.
SEQUENCE: 80
ATGFPGAAGR LGPPGPAGN                                            19

SEQ ID NO: 81        moltype = AA  length = 19
FEATURE              Location/Qualifiers
source               1..19
                     mol_type = protein
                     organism = unidentified
SITE                 1..19
                     note = P at position 2 is hydroxyproline.
SEQUENCE: 81
GPGPQGPAGA SGPRGLTGD                                            19

SEQ ID NO: 82        moltype = AA  length = 19
FEATURE              Location/Qualifiers
source               1..19
                     mol_type = protein
                     organism = unidentified
SEQUENCE: 82
PGPAGASGPA GPRGPVGVA                                            19

SEQ ID NO: 83        moltype = AA  length = 20
FEATURE              Location/Qualifiers
source               1..20
                     mol_type = protein
                     organism = unidentified
SITE                 1..20
```

-continued

```
                            note = P at position 5 and 12 are hydroxyproline.
SEQUENCE: 83
GFAGPPGADG QPGAKGEAGD                                              20

SEQ ID NO: 84              moltype = AA   length = 20
FEATURE                    Location/Qualifiers
source                     1..20
                           mol_type = protein
                           organism = unidentified
SITE                       1..20
                           note = P at position 5, 12 and 17 are hydroxyproline.
SEQUENCE: 84
GSAGPPGQDG RPGPPGPVGA                                              20

SEQ ID NO: 85              moltype = AA   length = 20
FEATURE                    Location/Qualifiers
source                     1..20
                           mol_type = protein
                           organism = unidentified
SEQUENCE: 85
SGPAGPAGPS GPRGPAGPSG                                              20

SEQ ID NO: 86              moltype = AA   length = 20
FEATURE                    Location/Qualifiers
source                     1..20
                           mol_type = protein
                           organism = unidentified
SITE                       1..20
                           note = P at position 16 is hydroxyproline.
SEQUENCE: 86
AVGAQGPIGP RGPSGPPGPD                                              20

SEQ ID NO: 87              moltype = AA   length = 20
FEATURE                    Location/Qualifiers
source                     1..20
                           mol_type = protein
                           organism = unidentified
SITE                       1..20
                           note = P at position 8 is hydroxyproline.
SEQUENCE: 87
GIAGASGPLG PAGAAGRPGN                                              20

SEQ ID NO: 88              moltype = AA   length = 20
FEATURE                    Location/Qualifiers
source                     1..20
                           mol_type = protein
                           organism = unidentified
SITE                       1..20
                           note = P at position 4 and 18 are hydroxyproline.
SEQUENCE: 88
AGAPGPAGAT GAPGPQGPVG                                              20

SEQ ID NO: 89              moltype = AA   length = 20
FEATURE                    Location/Qualifiers
source                     1..20
                           mol_type = protein
                           organism = unidentified
SITE                       1..20
                           note = P at position 8 is hydroxyproline.
SEQUENCE: 89
GGPGPQGPAG ASGPRGLTGD                                              20

SEQ ID NO: 90              moltype = AA   length = 21
FEATURE                    Location/Qualifiers
source                     1..21
                           mol_type = protein
                           organism = unidentified
SITE                       1..21
                           note = P at position 12 is hydroxyproline.
SEQUENCE: 90
GARGDAGAAG VPGGVGSAGP Q                                            21

SEQ ID NO: 91              moltype = AA   length = 21
FEATURE                    Location/Qualifiers
source                     1..21
                           mol_type = protein
                           organism = unidentified
SITE                       1..21
                           note = P at position 6 is hydroxyproline.
```

-continued

```
SEQUENCE: 91
GARGSPGAAG NDGARGDAGA A                                              21

SEQ ID NO: 92           moltype = AA  length = 21
FEATURE                 Location/Qualifiers
source                  1..21
                        mol_type = protein
                        organism = unidentified
SITE                    1..21
                        note = P at position 8 is hydroxyproline.
SEQUENCE: 92
GKAGPAGPAG QDGAAGPPGP A                                              21

SEQ ID NO: 93           moltype = AA  length = 21
FEATURE                 Location/Qualifiers
source                  1..21
                        mol_type = protein
                        organism = unidentified
SITE                    1..21
                        note = P at position 8 and 17 are hydroxyproline.
SEQUENCE: 93
GSPGAPGPDG KAGPAGPAGQ D                                              21

SEQ ID NO: 94           moltype = AA  length = 21
FEATURE                 Location/Qualifiers
source                  1..21
                        mol_type = protein
                        organism = unidentified
SITE                    1..21
                        note = P at position 9 is hydroxyproline.
SEQUENCE: 94
GFTGPAGEPG EPGPSGPMGP R                                              21

SEQ ID NO: 95           moltype = AA  length = 21
FEATURE                 Location/Qualifiers
source                  1..21
                        mol_type = protein
                        organism = unidentified
SITE                    1..21
                        note = P at position 3 and 17 are hydroxyproline.
SEQUENCE: 95
GAPGPPGAAG EKGEPGPVGP A                                              21

SEQ ID NO: 96           moltype = AA  length = 21
FEATURE                 Location/Qualifiers
source                  1..21
                        mol_type = protein
                        organism = unidentified
SITE                    1..21
                        note = P at position 8 is hydroxyproline.
SEQUENCE: 96
GAVGPAGPAG ARGAPGPAGP R                                              21

SEQ ID NO: 97           moltype = AA  length = 21
FEATURE                 Location/Qualifiers
source                  1..21
                        mol_type = protein
                        organism = unidentified
SITE                    1..21
                        note = P at position 11 and 18 are hydroxyproline.
SEQUENCE: 97
GISGPSGLIG PPGITGLPGA R                                              21

SEQ ID NO: 98           moltype = AA  length = 21
FEATURE                 Location/Qualifiers
source                  1..21
                        mol_type = protein
                        organism = unidentified
SEQUENCE: 98
GLMGPRGPSG PPGAPGPQGL Q                                              21

SEQ ID NO: 99           moltype = AA  length = 21
FEATURE                 Location/Qualifiers
source                  1..21
                        mol_type = protein
                        organism = unidentified
SITE                    1..21
                        note = P at position 8 is hydroxyproline.
SEQUENCE: 99
```

-continued

```
GLMGPRGPSG PPGAPGPQGL Q                                               21

SEQ ID NO: 100          moltype = AA   length = 21
FEATURE                 Location/Qualifiers
source                  1..21
                        mol_type = protein
                        organism = unidentified
SITE                    1..21
                        note = P at position 8 and 17 are hydroxyproline.
SEQUENCE: 100
GSPGAPGPDG KAGPAGPAGD K                                               21

SEQ ID NO: 101          moltype = AA   length = 21
FEATURE                 Location/Qualifiers
source                  1..21
                        mol_type = protein
                        organism = unidentified
SITE                    1..21
                        note = P at position 8, 17 and 18 are hydroxyproline.
SEQUENCE: 101
GSPGSPGPDG KTGSAGPPGQ D                                               21

SEQ ID NO: 102          moltype = AA   length = 21
FEATURE                 Location/Qualifiers
source                  1..21
                        mol_type = protein
                        organism = unidentified
SITE                    1..21
                        note = P at position 9 is hydroxyproline.
SEQUENCE: 102
GFTGPPGEPG EAGASGPMGP R                                               21

SEQ ID NO: 103          moltype = AA   length = 21
FEATURE                 Location/Qualifiers
source                  1..21
                        mol_type = protein
                        organism = unidentified
SEQUENCE: 103
PSGEPGPAGA SGPAGPRGPV G                                               21

SEQ ID NO: 104          moltype = AA   length = 21
FEATURE                 Location/Qualifiers
source                  1..21
                        mol_type = protein
                        organism = unidentified
SITE                    1..21
                        note = P at position 3 and 18 are hydroxyproline.
SEQUENCE: 104
GEPGMPGSKG MTGSPGSPGP D                                               21

SEQ ID NO: 105          moltype = AA   length = 21
FEATURE                 Location/Qualifiers
source                  1..21
                        mol_type = protein
                        organism = unidentified
SITE                    1..21
                        note = P at position 4 is hydroxyproline.
SEQUENCE: 105
IGLPGMTGPQ GEAGREGSPG N                                               21

SEQ ID NO: 106          moltype = AA   length = 22
FEATURE                 Location/Qualifiers
source                  1..22
                        mol_type = protein
                        organism = unidentified
SITE                    1..22
                        note = P at position 13 is hydroxyproline.
SEQUENCE: 106
DGARGDAGAA GVPGGVGSAG PQ                                              22

SEQ ID NO: 107          moltype = AA   length = 22
FEATURE                 Location/Qualifiers
source                  1..22
                        mol_type = protein
                        organism = unidentified
SITE                    1..22
                        note = P at position 3, 6, 20 and 21 are hydroxyproline.
SEQUENCE: 107
GAPGLPGPPG PPGPAGIGEP FP                                              22
```

-continued

```
SEQ ID NO: 108          moltype = AA  length = 22
FEATURE                 Location/Qualifiers
source                  1..22
                        mol_type = protein
                        organism = unidentified
SITE                    1..22
                        note = P at position 16 is hydroxyproline.
SEQUENCE: 108
SGMAGLPGPA GPPGEPGPAG PT                                         22

SEQ ID NO: 109          moltype = AA  length = 22
FEATURE                 Location/Qualifiers
source                  1..22
                        mol_type = protein
                        organism = unidentified
SEQUENCE: 109
SGPAGPAGPS GPRGPAGPSG PA                                         22

SEQ ID NO: 110          moltype = AA  length = 22
FEATURE                 Location/Qualifiers
source                  1..22
                        mol_type = protein
                        organism = unidentified
SEQUENCE: 110
SGPAGPAGAA GPAGPRGPAG PA                                         22

SEQ ID NO: 111          moltype = AA  length = 22
FEATURE                 Location/Qualifiers
source                  1..22
                        mol_type = protein
                        organism = unidentified
SITE                    1..22
                        note = P at position 4, 13 and 19 are hydroxyproline.
SEQUENCE: 111
SGGPGEAGRE GSPGHDGAPG RD                                         22

SEQ ID NO: 112          moltype = AA  length = 22
FEATURE                 Location/Qualifiers
source                  1..22
                        mol_type = protein
                        organism = unidentified
SITE                    1..22
                        note = P at position 4 is hydroxyproline.
SEQUENCE: 112
IGLPGMTGPQ GEAGREGSPG ND                                         22

SEQ ID NO: 113          moltype = AA  length = 22
FEATURE                 Location/Qualifiers
source                  1..22
                        mol_type = protein
                        organism = unidentified
SITE                    1..22
                        note = P at position 16 is hydroxyproline.
SEQUENCE: 113
PRGGPGPQGP AGASGPRGLT GD                                         22

SEQ ID NO: 114          moltype = AA  length = 23
FEATURE                 Location/Qualifiers
source                  1..23
                        mol_type = protein
                        organism = unidentified
SITE                    1..23
                        note = P at position 5 is hydroxyproline.
SEQUENCE: 114
GETGPAGGRG SEGPQGARGE PGN                                        23

SEQ ID NO: 115          moltype = AA  length = 23
FEATURE                 Location/Qualifiers
source                  1..23
                        mol_type = protein
                        organism = unidentified
SITE                    1..23
                        note = P at position 14 is hydroxyproline.
SEQUENCE: 115
NDGARGDAGA AGVPGGVGSA GPQ                                        23

SEQ ID NO: 116          moltype = AA  length = 23
FEATURE                 Location/Qualifiers
```

-continued

```
source                  1..23
                        mol_type = protein
                        organism = unidentified
SITE                    1..23
                        note = P at position 9 is hydroxyproline.
SEQUENCE: 116
GFTGPPGEPG EAGASGPMGP RGA                                    23

SEQ ID NO: 117          moltype = AA  length = 23
FEATURE                 Location/Qualifiers
source                  1..23
                        mol_type = protein
                        organism = unidentified
SITE                    1..23
                        note = P at position 11 and 18 are hydroxyproline.
SEQUENCE: 117
GISGPSGLIG PPGITGLPGA RGE                                    23

SEQ ID NO: 118          moltype = AA  length = 23
FEATURE                 Location/Qualifiers
source                  1..23
                        mol_type = protein
                        organism = unidentified
SITE                    1..23
                        note = P at position 8, 9 and 17 are hydroxyproline.
SEQUENCE: 118
GKTGSAGPPG QDGRPGPPGP VGA                                    23

SEQ ID NO: 119          moltype = AA  length = 23
FEATURE                 Location/Qualifiers
source                  1..23
                        mol_type = protein
                        organism = unidentified
SITE                    1..23
                        note = P at position 2, 3, 5 and 6 are hydroxyproline.
SEQUENCE: 119
GPPGPPGPPG PPGPSGGGFD IGF                                    23

SEQ ID NO: 120          moltype = AA  length = 23
FEATURE                 Location/Qualifiers
source                  1..23
                        mol_type = protein
                        organism = unidentified
SITE                    1..23
                        note = P at position 17 is hydroxyproline.
SEQUENCE: 120
GPSGQDGRGG PPGPTGPRGQ PGN                                    23

SEQ ID NO: 121          moltype = AA  length = 24
FEATURE                 Location/Qualifiers
source                  1..24
                        mol_type = protein
                        organism = unidentified
SITE                    1..24
                        note = P at position 3, 6, 17 and 18 are hydroxyproline.
SEQUENCE: 121
GAPGRPGEVG AAGPPGPPGE RGST                                   24

SEQ ID NO: 122          moltype = AA  length = 24
FEATURE                 Location/Qualifiers
source                  1..24
                        mol_type = protein
                        organism = unidentified
SITE                    1..24
                        note = P at position 17, 18 and 20 are hydroxyproline.
SEQUENCE: 122
GARGEPGNPG PGGAAGPPGP PGSD                                   24

SEQ ID NO: 123          moltype = AA  length = 24
FEATURE                 Location/Qualifiers
source                  1..24
                        mol_type = protein
                        organism = unidentified
SITE                    1..24
                        note = P at position 15 is hydroxyproline.
SEQUENCE: 123
GNDGARGDAG AAGVPGGVGS AGPQ                                   24

SEQ ID NO: 124          moltype = AA  length = 24
```

-continued

```
FEATURE                  Location/Qualifiers
source                   1..24
                         mol_type = protein
                         organism = unidentified
SITE                     1..24
                         note = P at position 2 is hydroxyproline.
SEQUENCE: 124
GPAGQDGAAG PPGPAGSRGL PGVM                                          24

SEQ ID NO: 125           moltype = AA  length = 24
FEATURE                  Location/Qualifiers
source                   1..24
                         mol_type = protein
                         organism = unidentified
SEQUENCE: 125
AVPGPMGPMG PRGPPGPPGL SGPQ                                          24

SEQ ID NO: 126           moltype = AA  length = 24
FEATURE                  Location/Qualifiers
source                   1..24
                         mol_type = protein
                         organism = unidentified
SITE                     1..24
                         note = P at position 8 is hydroxyproline.
SEQUENCE: 126
GKEGPAGPSG QDGRGGPPGP TGPR                                          24

SEQ ID NO: 127           moltype = AA  length = 24
FEATURE                  Location/Qualifiers
source                   1..24
                         mol_type = protein
                         organism = unidentified
SEQUENCE: 127
GMPGPSGPSG DSGPAGPAGP SGPR                                          24

SEQ ID NO: 128           moltype = AA  length = 24
FEATURE                  Location/Qualifiers
source                   1..24
                         mol_type = protein
                         organism = unidentified
SITE                     1..24
                         note = P at position 8 is hydroxyproline.
SEQUENCE: 128
GEIGPAGPSG PAGPQGQRGE PGTN                                          24

SEQ ID NO: 129           moltype = AA  length = 24
FEATURE                  Location/Qualifiers
source                   1..24
                         mol_type = protein
                         organism = unidentified
SITE                     1..24
                         note = P at position 3 and 17 are hydroxyproline.
SEQUENCE: 129
GLPGSPGSAG PQGKEGPAGP SGQD                                          24

SEQ ID NO: 130           moltype = AA  length = 25
FEATURE                  Location/Qualifiers
source                   1..25
                         mol_type = protein
                         organism = unidentified
SITE                     1..25
                         note = P at position 3, 16 and 19 are hydroxyproline.
SEQUENCE: 130
TGPAGPAGPL GSAGPPGFPG APGPK                                         25

SEQ ID NO: 131           moltype = AA  length = 25
FEATURE                  Location/Qualifiers
source                   1..25
                         mol_type = protein
                         organism = unidentified
SITE                     1..25
                         note = P at position 1 is hydroxyproline.
SEQUENCE: 131
PGPAGAVGAQ GPIGPRGPSG PPGPD                                         25

SEQ ID NO: 132           moltype = AA  length = 25
FEATURE                  Location/Qualifiers
source                   1..25
                         mol_type = protein
```

```
                                organism = unidentified
SITE                            1..25
                                note = P at position 1 and 18 are hydroxyproline.
SEQUENCE: 132
PGPAGAVGAQ GPIGPRGPSG PPGPD                                      25

SEQ ID NO: 133                  moltype = AA  length = 26
FEATURE                         Location/Qualifiers
source                          1..26
                                mol_type = protein
                                organism = unidentified
SITE                            1..26
                                note = P at position 3, 6, 20 and 22 are hydroxyproline.
SEQUENCE: 133
GAPGLPGPPG PPGPAGIGEP FPIIPQ                                     26

SEQ ID NO: 134                  moltype = AA  length = 26
FEATURE                         Location/Qualifiers
source                          1..26
                                mol_type = protein
                                organism = unidentified
SEQUENCE: 134
ALAVPGPMGP MGPRGPPGPP GLSGPQ                                     26

SEQ ID NO: 135                  moltype = AA  length = 26
FEATURE                         Location/Qualifiers
source                          1..26
                                mol_type = protein
                                organism = unidentified
SITE                            1..26
                                note = P at position 8 is hydroxyproline.
SEQUENCE: 135
GIRGLTGPIG PPGPAGPQGD KGEPGA                                     26

SEQ ID NO: 136                  moltype = AA  length = 26
FEATURE                         Location/Qualifiers
source                          1..26
                                mol_type = protein
                                organism = unidentified
SITE                            1..26
                                note = P at position 17 is hydroxyproline.
SEQUENCE: 136
GPPGAAGEKG EPGPVGPAGS TGPRGG                                     26

SEQ ID NO: 137                  moltype = AA  length = 26
FEATURE                         Location/Qualifiers
source                          1..26
                                mol_type = protein
                                organism = unidentified
SITE                            1..26
                                note = P at position 3 and 9 are hydroxyproline.
SEQUENCE: 137
GFPGPRGGPG PQGPAGASGP RGLTGD                                     26

SEQ ID NO: 138                  moltype = AA  length = 27
FEATURE                         Location/Qualifiers
source                          1..27
                                mol_type = protein
                                organism = unidentified
SITE                            1..27
                                note = P at position 3, 6, 20 and 22 are hydroxyproline.
SEQUENCE: 138
GAPGLPGPPG PPGPAGIGEP FPIIPQP                                    27

SEQ ID NO: 139                  moltype = AA  length = 27
FEATURE                         Location/Qualifiers
source                          1..27
                                mol_type = protein
                                organism = unidentified
SITE                            1..27
                                note = P at position 3, 6, 17 and 18 are hydroxyproline.
SEQUENCE: 139
GAPGRPGEVG AAGPPGPPGE RGSTGSD                                    27

SEQ ID NO: 140                  moltype = AA  length = 27
FEATURE                         Location/Qualifiers
source                          1..27
                                mol_type = protein
                                organism = unidentified
```

-continued

```
SITE                       1..27
                           note = P at position 3, 20 and 21 are hydroxyproline.
SEQUENCE: 140
GFPGAAGRVG PPGPAGAAGP PGPVGPG                                        27

SEQ ID NO: 141             moltype = AA  length = 27
FEATURE                    Location/Qualifiers
source                     1..27
                           mol_type = protein
                           organism = unidentified
SITE                       1..27
                           note = P at position 3 and 17 are hydroxyproline.
SEQUENCE: 141
GLPGPAGPPG EPGPAGPTGP AGPRGPS                                        27

SEQ ID NO: 142             moltype = AA  length = 27
FEATURE                    Location/Qualifiers
source                     1..27
                           mol_type = protein
                           organism = unidentified
SITE                       1..27
                           note = P at position 5 is hydroxyproline.
SEQUENCE: 142
GLTGPIGPPG PAGPQGDKGE PGAAGPL                                        27

SEQ ID NO: 143             moltype = AA  length = 27
FEATURE                    Location/Qualifiers
source                     1..27
                           mol_type = protein
                           organism = unidentified
SEQUENCE: 143
GMPGPSGPSG DSGPAGPAGP SGPRGPA                                        27

SEQ ID NO: 144             moltype = AA  length = 27
FEATURE                    Location/Qualifiers
source                     1..27
                           mol_type = protein
                           organism = unidentified
SITE                       1..27
                           note = P at position 5, 17 and 18 are hydroxyproline.
SEQUENCE: 144
GNTGPAGPAG PLGSAGPPGF PGAPGPK                                        27

SEQ ID NO: 145             moltype = AA  length = 27
FEATURE                    Location/Qualifiers
source                     1..27
                           mol_type = protein
                           organism = unidentified
SITE                       1..27
                           note = P at position 3, 17 and 18 are hydroxyproline.
SEQUENCE: 145
GAPGRPGEVG AAGPPGPPGE RGSTGSD                                        27

SEQ ID NO: 146             moltype = AA  length = 28
FEATURE                    Location/Qualifiers
source                     1..28
                           mol_type = protein
                           organism = unidentified
SITE                       1..28
                           note = P at position 18 is hydroxyproline.
SEQUENCE: 146
AGLPGPAGPP GEPGPAGPTG PAGPRGPS                                       28

SEQ ID NO: 147             moltype = AA  length = 28
FEATURE                    Location/Qualifiers
source                     1..28
                           mol_type = protein
                           organism = unidentified
SITE                       1..28
                           note = P at position 4, 18 and 21 are hydroxyproline.
SEQUENCE: 147
AGLPGPAGPP GEPGPAGPTG PAGPRGPS                                       28

SEQ ID NO: 148             moltype = AA  length = 28
FEATURE                    Location/Qualifiers
source                     1..28
                           mol_type = protein
                           organism = unidentified
SITE                       1..28
```

-continued

```
                              note = P at position 4 and 18 are hydroxyproline.
SEQUENCE: 148
AGLPGPAGPP GEPGPAGPTG PAGPRGPS                           28

SEQ ID NO: 149          moltype = AA  length = 28
FEATURE                 Location/Qualifiers
source                  1..28
                        mol_type = protein
                        organism = unidentified
SITE                    1..28
                        note = P at position 3, 6, 8, 20 and 22 are hydroxyproline.
SEQUENCE: 149
GAPGLPGPPG PPGPAGIGEP FPIIPQPE                           28

SEQ ID NO: 150          moltype = AA  length = 28
FEATURE                 Location/Qualifiers
source                  1..28
                        mol_type = protein
                        organism = unidentified
SITE                    1..28
                        note = P at position 3, 6 and 20 are hydroxyproline.
SEQUENCE: 150
GAPGLPGPPG PPGPAGIGEP FPIIPQPE                           28

SEQ ID NO: 151          moltype = AA  length = 28
FEATURE                 Location/Qualifiers
source                  1..28
                        mol_type = protein
                        organism = unidentified
SITE                    1..28
                        note = P at position 3, 6, 20 and 22 are hydroxyproline.
SEQUENCE: 151
GAPGLPGPPG PPGPAGIGEP FPIIPQPE                           28

SEQ ID NO: 152          moltype = AA  length = 28
FEATURE                 Location/Qualifiers
source                  1..28
                        mol_type = protein
                        organism = unidentified
SITE                    1..28
                        note = P at position 9, 18, 19 and 22 are hydroxyproline.
SEQUENCE: 152
DGAAGAAGPP GPTGPAGPPG FPGGPGAK                           28

SEQ ID NO: 153          moltype = AA  length = 28
FEATURE                 Location/Qualifiers
source                  1..28
                        mol_type = protein
                        organism = unidentified
SITE                    1..28
                        note = P at position 2, 5 and 18 are hydroxyproline.
SEQUENCE: 153
GPAGPQGATG ESGRPGEPGL PGSRGVSG                           28

SEQ ID NO: 154          moltype = AA  length = 29
FEATURE                 Location/Qualifiers
source                  1..29
                        mol_type = protein
                        organism = unidentified
SITE                    1..29
                        note = P at position 3, 6, 20 and 22 are hydroxyproline.
SEQUENCE: 154
GAPGLPGPPG PPGPAGIGEP FPIIPQPEK                          29

SEQ ID NO: 155          moltype = AA  length = 29
FEATURE                 Location/Qualifiers
source                  1..29
                        mol_type = protein
                        organism = unidentified
SITE                    1..29
                        note = P at position 3, 9, 11 and 27 are hydroxyproline.
SEQUENCE: 155
GAPGFQGLPG PAGPVGETGK PGDRGIPGD                          29

SEQ ID NO: 156          moltype = AA  length = 29
FEATURE                 Location/Qualifiers
source                  1..29
                        mol_type = protein
                        organism = unidentified
```

-continued

```
SITE                     1..29
                         note = P at position 5, 17, 18 and 20 are hydroxyproline.
SEQUENCE: 156
GEIGPAGPPG PPGPPGPPGP SGGGFDIGF                                        29

SEQ ID NO: 157           moltype = AA  length = 29
FEATURE                  Location/Qualifiers
source                   1..29
                         mol_type = protein
                         organism = unidentified
SEQUENCE: 157
GGAALAVPGP MGPMGPRGPP GPPGLSGPQ                                        29

SEQ ID NO: 158           moltype = AA  length = 29
FEATURE                  Location/Qualifiers
source                   1..29
                         mol_type = protein
                         organism = unidentified
SITE                     1..29
                         note = P at position 17 and 18 are hydroxyproline.
SEQUENCE: 158
GKEGPAGPSG QDGRGGPPGP TGPRGQPGN                                        29

SEQ ID NO: 159           moltype = AA  length = 29
FEATURE                  Location/Qualifiers
source                   1..29
                         mol_type = protein
                         organism = unidentified
SITE                     1..29
                         note = P at position 4 is hydroxyproline.
SEQUENCE: 159
LTGPIGPPGP AGPQGDKGEP GAAGPLGPT                                        29

SEQ ID NO: 160           moltype = AA  length = 29
FEATURE                  Location/Qualifiers
source                   1..29
                         mol_type = protein
                         organism = unidentified
SITE                     1..29
                         note = P at position 4, 5 and 19 are hydroxyproline.
SEQUENCE: 160
SAGPPGFPGA PGPKGEIGPA GPSGPAGPQ                                        29

SEQ ID NO: 161           moltype = AA  length = 30
FEATURE                  Location/Qualifiers
source                   1..30
                         mol_type = protein
                         organism = unidentified
SITE                     1..30
                         note = P at position 3, 6, 20 and 22 are hydroxyproline.
SEQUENCE: 161
GAPGLPGPPG PPGPAGIGEP FPIIPQPEKA                                       30

SEQ ID NO: 162           moltype = AA  length = 30
FEATURE                  Location/Qualifiers
source                   1..30
                         mol_type = protein
                         organism = unidentified
SITE                     1..30
                         note = P at position 3, 20 and 21 are hydroxyproline.
SEQUENCE: 162
GFPGAAGRVG PPGPAGAAGP PGPVGPGGKE                                       30

SEQ ID NO: 163           moltype = AA  length = 30
FEATURE                  Location/Qualifiers
source                   1..30
                         mol_type = protein
                         organism = unidentified
SITE                     1..30
                         note = P at position 17 and 20 are hydroxyproline.
SEQUENCE: 163
GFTGPAGEPG EPGPSGPMGP RGPIGPPGRN                                       30

SEQ ID NO: 164           moltype = AA  length = 30
FEATURE                  Location/Qualifiers
source                   1..30
                         mol_type = protein
                         organism = unidentified
SITE                     1..30
```

-continued

```
                           note = P at position 8 is hydroxyproline.
SEQUENCE: 164
GKAGPAGPAG QDGAAGPPGP AGSRGLPGVM                                         30

SEQ ID NO: 165              moltype = AA  length = 30
FEATURE                     Location/Qualifiers
source                      1..30
                            mol_type = protein
                            organism = unidentified
SITE                        1..30
                            note = P at position 17 is hydroxyproline.
SEQUENCE: 165
GMAGLPGPAG PPGEPGPAGP TGPAGPRGPS                                         30

SEQ ID NO: 166              moltype = AA  length = 30
FEATURE                     Location/Qualifiers
source                      1..30
                            mol_type = protein
                            organism = unidentified
SITE                        1..30
                            note = P at position 5, 18 and 21 are hydroxyproline.
SEQUENCE: 166
GAAGPPGKNG EDGESGKPGR PGERGPPGPQ                                         30

SEQ ID NO: 167              moltype = AA  length = 30
FEATURE                     Location/Qualifiers
source                      1..30
                            mol_type = protein
                            organism = unidentified
SITE                        1..30
                            note = P at position 8 and 9 are hydroxyproline.
SEQUENCE: 167
GAPGLRGPPG PDGNNGPAGP VGVVGGAGEK                                         30

SEQ ID NO: 168              moltype = AA  length = 30
FEATURE                     Location/Qualifiers
source                      1..30
                            mol_type = protein
                            organism = unidentified
SITE                        1..30
                            note = P at position 8 is hydroxyproline.
SEQUENCE: 168
GAPGLRGPPG PDGNNGPAGP VGVVGGAGEK                                         30

SEQ ID NO: 169              moltype = AA  length = 30
FEATURE                     Location/Qualifiers
source                      1..30
                            mol_type = protein
                            organism = unidentified
SITE                        1..30
                            note = P at position 3, 20 and 21 are hydroxyproline.
SEQUENCE: 169
GFPGAAGRVG PPGPAGIAGP PGSTGPAGKD                                         30

SEQ ID NO: 170              moltype = AA  length = 30
FEATURE                     Location/Qualifiers
source                      1..30
                            mol_type = protein
                            organism = unidentified
SITE                        1..30
                            note = P at position 17 is hydroxyproline.
SEQUENCE: 170
GIRGLTGPIG PPGPAGPQGD KGEPGAAGPL                                         30

SEQ ID NO: 171              moltype = AA  length = 30
FEATURE                     Location/Qualifiers
source                      1..30
                            mol_type = protein
                            organism = unidentified
SITE                        1..30
                            note = P at position 6, 17 and 23 are hydroxyproline.
SEQUENCE: 171
GLTGFPGAAG RVGPPGPAGI AGPPGSTGPA                                         30

SEQ ID NO: 172              moltype = AA  length = 30
FEATURE                     Location/Qualifiers
source                      1..30
                            mol_type = protein
                            organism = unidentified
```

-continued

```
SITE                    1..30
                        note = P at position 5 is hydroxyproline.
SEQUENCE: 172
GLTGPIGPPG PAGPQGDKGE PGAAGPLGPT                              30

SEQ ID NO: 173          moltype = AA  length = 30
FEATURE                 Location/Qualifiers
source                  1..30
                        mol_type = protein
                        organism = unidentified
SEQUENCE: 173
GMPGPSGPSG DSGPAGPAGP SGPRGPAGPS                              30

SEQ ID NO: 174          moltype = AA  length = 30
FEATURE                 Location/Qualifiers
source                  1..30
                        mol_type = protein
                        organism = unidentified
SITE                    1..30
                        note = P at position 4, 9 and 18 are hydroxyproline.
SEQUENCE: 174
RGEPGAPGPL GIAGASGPLG PAGAAGRPGN                              30
```